United States Patent
Alexandrov et al.

(10) Patent No.: US 9,791,436 B2
(45) Date of Patent: *Oct. 17, 2017

(54) PROTEASE-BASED BIOSENSOR

(71) Applicant: THE UNIVERSITY OF QUEENSLAND, St Lucia (AU)

(72) Inventors: Kirill Alexandrov, St Lucia (AU); Viktor Stein, St Lucia (AU); Matt Trau, St Lucia (AU)

(73) Assignee: THE UNIVERSITY OF QUEENSLAND, St Lucia (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/427,982

(22) PCT Filed: Sep. 12, 2013

(86) PCT No.: PCT/AU2013/001039
§ 371 (c)(1),
(2) Date: Mar. 12, 2015

(87) PCT Pub. No.: WO2014/040129
PCT Pub. Date: Mar. 20, 2014

(65) Prior Publication Data
US 2015/0226731 A1    Aug. 13, 2015

(30) Foreign Application Priority Data
Sep. 12, 2012 (AU) ................. 2012903979

(51) Int. Cl.
*G01N 33/542* (2006.01)
*C12Q 1/37* (2006.01)
(Continued)

(52) U.S. Cl.
CPC ....... *G01N 33/542* (2013.01); *C07K 16/3069* (2013.01); *C07K 16/36* (2013.01);
(Continued)

(58) Field of Classification Search
None
See application file for complete search history.

(56) References Cited

U.S. PATENT DOCUMENTS

| 4,463,090 A | 7/1984 | Harris |
| 2002/0102577 A1 | 8/2002 | Raillard et al. |

(Continued)

FOREIGN PATENT DOCUMENTS

| WO | 02/10750 | 2/2002 |
| WO | 2005/010198 | 2/2005 |

(Continued)

OTHER PUBLICATIONS

Int'l Search Report for PCT/AU2013/001039, six pages (Nov. 2013).

(Continued)

*Primary Examiner* — Jacob Cheu
(74) *Attorney, Agent, or Firm* — Nixon & Vanderhye PC

(57) ABSTRACT

A biosensor molecule comprises: a protease amino acid sequence; at least one sensor comprising at least one sensor amino acid sequence which is responsive to at least one target molecule; and an inhibitor of the protease activity of said protease amino acid sequence; wherein the biosensor is switchable from a protease active to a protease inactive state, or from a protease inactive to a protease active state when said sensor responds to said target molecule. The biosensor protease may be a protease of a virus such as a Potyvirus or a Flavivirus wherein the inhibitor is an autoinhibitory peptide derived from the virus. The biosensor may respond to the target molecule allosterically or may be cleaved by a target protease molecule.

32 Claims, 13 Drawing Sheets

(51) Int. Cl.
| | |
|---|---|
| G01N 33/543 | (2006.01) |
| C12N 9/50 | (2006.01) |
| C12N 15/62 | (2006.01) |
| C07K 16/30 | (2006.01) |
| C07K 16/36 | (2006.01) |
| G01N 33/573 | (2006.01) |
| G01N 33/532 | (2006.01) |

(52) U.S. Cl.
CPC ............ *C12N 9/503* (2013.01); *C12N 9/506* (2013.01); *C12N 15/62* (2013.01); *C12Q 1/37* (2013.01); *G01N 33/532* (2013.01); *G01N 33/54366* (2013.01); *G01N 33/573* (2013.01); *C07K 2317/22* (2013.01); *C07K 2317/569* (2013.01); *C07K 2319/21* (2013.01); *C07K 2319/50* (2013.01); *C07K 2319/70* (2013.01); *C12N 2770/24022* (2013.01); *C12N 2770/34022* (2013.01); *G01N 2333/005* (2013.01); *G01N 2333/18* (2013.01); *G01N 2333/96463* (2013.01)

(56) References Cited

U.S. PATENT DOCUMENTS

| | | | |
|---|---|---|---|
| 2002/0127623 | A1 | 9/2002 | Minshull et al. |
| 2008/0107660 | A1 | 5/2008 | Self |
| 2010/0221212 | A1 | 9/2010 | Stagliano et al. |
| 2011/0003312 | A1* | 1/2011 | Berget ............... C12Q 1/37 435/7.4 |
| 2011/0143963 | A1 | 6/2011 | Koide et al. |
| 2015/0226731 | A1 | 8/2015 | Alexandrov et al. |
| 2016/0223529 | A1 | 8/2016 | Stein |

FOREIGN PATENT DOCUMENTS

| | | |
|---|---|---|
| WO | 2005/083431 | 9/2005 |
| WO | 2009/026338 | 2/2009 |
| WO | 2009/062170 | 5/2009 |
| WO | 2012/038950 | 3/2012 |
| WO | 2014/040129 | 3/2014 |

OTHER PUBLICATIONS

Written Opinion for PCT/AU2013/001039, eight pages (Nov. 2013).
Carrington et al. "Autocatalytic processing of the potyvirus helper component proteinase in *Escherichia coli* and in vitro" *Journal of Virology*, vol. 63, No. 10, pp. 4459-4463 (Oct. 1989).
Guntas et al. "A molecular switch created by in vitro recombination of nonhomologous genes" *Chemistry & Biology*, vol. 11, No. 11, pp. 1483-1487 (Nov. 2004).
Huang & Koide "Rational conversion of affinity reagents into label-free sensors for peptide motifs by designed allostery" *ACS Chemistry & Biology*, vol. 5, No. 3, pp. 273-277 (Mar. 2010).
Ingallinella et al. "Potent peptide inhibitors of human hepatitis C virus NS3 protease are obtained by optimizing the cleavage products" *Biochemistry*, vol. 37, No. 25, pp. 8906-8914 (Jun. 1998).
O'Loughlin & Matsumura "HIV protease-activated molecular switches based on beta-glucuronidase and alkaline phosphatase" *Comb. Chem. & High Throughput Screening*, vol. 9, No. 4, pp. 313-320 (May 2006).
Pallister & Watson Chapters 18.3-18.6 of *Haematology* $2^{nd}$ *Ed.*, Scion, pp. 336-347 (Oct. 2010).
Saghatelian et al. "DNA detection and signal amplification via an engineered allosteric enzyme" *Journal of the American Chemical Society*, vol. 125, pp. 344-345 (Jan. 2003).
Shlyahovsky et al. "Biocatalytic evolution of a biocatalyst marker: Towards the ultrasensitive detection of immunocomplexes and DNA analysis" *Angew. Chem. Int'l Ed.* vol. 45, No. 29, pp. 4815-4819 (Jul. 2006).
Stein & Alexandrov "Synthetic signal sensing and transduction systems based on autoinhibited proteases" abstract at *Sixth International Meeting on Synthetic Biology*, London (Jul. 2013).
Steinkühler et al. "Product inhibition of the hepatitis C virus NS3 protease" *Biochemistry*, vol. 37, No. 25, pp. 8899-8905 (Jun. 1998).
Virel et al. "Quantification of prothrombin in human plasma amplified by autocatalytic reaction" *Analytical Chemistry*, vol. 84, No. 5, pp. 2380-2387 (Mar. 2012).
Wehr et al. "Monitoring regulated protein-protein interactions using split TEV" *Nature Methods*, vol. 3, No. 12, pp. 985-993 (Dec. 2006).
Zhuang & Liu "Investigation of the binding specify of Erbin-PDZ affinity clamp by molecular dynamics simulations" *Computational and Theoretical Chemistry*, vol. 963, Nos. 2-3, pp. 448-452 (Feb. 2011).
U.S. Appl. No. 60/986,475, Koide et al, filed Nov. 8, 2007.
Binz et al. "Engineering novel binding proteins from nonimmunoglobulin domains" *Nature Biotechnology*, vol. 23, No. 10, pp. 1257-1268 (Oct. 2005).
Huang et al. "Design of protein function leaps by directed domain interface evolution" *Proceedings of the National Academy of Sciences USA*, vol. 105, No. 18, pp. 6578-6583 (May 2008).
Huang et al. "Structural basis for exquisite specificity of affinity clamps, synthetic binding proteins generated through directed domain-interface evolution" *Journal of Molecular Biology*, vol. 392, No. 5, pp. 1221-1231 (Oct. 2009).
Shekhawat & Ghosh "Split-protein systems: beyond binary protein-protein interactions" *Current Opinion in Chemical Biology*, vol. 15, No. 6, pp. 789-797 (Dec. 2011).
Stein & Alexandrov "Protease-based synthetic sensing and signal amplification" *Proceedings of the National Academy of Sciences USA*, vol. 111, No. 45, pp. 15934-15939 (Nov. 2014).
Stein & Alexandrov "Synthetic protein switches: Design principles and applications" *Trends in Biotechnology*, vol. 33, No. 2, pp. 101-110 (Feb. 2015).
Stratton & Loh "Converting a protein into a switch for biosensing and functional regulation" *Protein Science*, vol. 20, No. 1, pp. 19-29 (Jan. 2011).
EPO supplementary search report & search opinion for corresponding European Application 13837496.2, 10 pages, dated Feb. 25, 2016.
U.S. Appl. No. 60/986,475 of Koide et al., 47 pages, filed Nov. 8, 2007.
First Office Action for related U.S. Appl. No. 15/021,494, 10 pages, dated Oct. 20, 2016.
Int'l Preliminary Report on Patentability for Int'l Application PCT/AU2015/050669, ten pages, dated May 2, 2017.
Final Office Action for related U.S. Appl. No. 15/021,494, six pages, dated Mar. 31, 2017.

\* cited by examiner

Basic Design – Intramolecular Autoinhibition

Extended Design – Intermolecular Autoinhibition

Integrated Signal Sensing and Amplification Networks

Figure Legend

- Autoinhibition Domain
- Target or Amplifier Protease
- Biosensor Protease
- Protease Labile Linkers
- Linker
- Dimerization Motif
- Ligand
- Receptor Scaffold

SEQUENCE LISTING

<160> NUMBER OF SEQ ID NOS: 84

<210> SEQ ID NO 1
<211> LENGTH: 253
<212> TYPE: PRT
<213> ORGANISM: Artificial Sequence
<220> FEATURE:
<223> OTHER INFORMATION: protease construct

<400> SEQUENCE: 1

```
Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
                100                 105                 110
```

Cys Met Val Ser Thr Asn Phe Gln Gln Lys Ser Val Ser Ser Leu Val
            115                 120                 125

Ser Glu Ser Ser His Ile Val His Lys Glu Asp Thr Ser Phe Trp Gln
130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Thr Leu Val Glu Asp Ala Pro Glu
    210                 215                 220

Asp Phe Met Ser Gly Leu Val Pro Arg Gly Val Gly Arg Glu Thr Val
225                 230                 235                 240

Arg Phe Ala Pro Gly Ser Thr His His His His His
                245                 250

<210> SEQ ID NO 2
<211> LENGTH: 251
<212> TYPE: PRT
<213> ORGANISM: Artificial Sequence
<220> FEATURE:
<223> OTHER INFORMATION: protease construct

<400> SEQUENCE: 2

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
            100                 105                 110

Cys Met Val Ser Thr Asn Phe Gln Gln Lys Ser Val Ser Ser Leu Val
            115                 120                 125

Ser Glu Ser Ser His Ile Val His Met Arg Asp Thr Ser Phe Trp Gln
130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Thr Leu Val Glu Asp Ala Pro Ser
    210                 215                 220

```
Gly Leu Val Pro Arg Gly Val Ser Gly Glu Gly Thr Val Arg Phe
225                 230                 235                 240

Gly Pro Gly Ser Thr His His His His His
                245                 250

<210> SEQ ID NO 3
<211> LENGTH: 251
<212> TYPE: PRT
<213> ORGANISM: Artificial Sequence
<220> FEATURE:
<223> OTHER INFORMATION: protease construct

<400> SEQUENCE: 3

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
                20                  25                  30

Glu Arg Leu Phe Gly Ile Gly Phe Gly Pro Tyr Ile Ile Ala Asn Gln
            35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
            100                 105                 110

Cys Met Val Ser Thr Asn Phe Gln Gln Lys Ser Val Ser Ser Leu Val
        115                 120                 125

Ser Glu Ser Ser His Ile Val His Met Arg Asp Thr Ser Phe Trp Gln
    130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Thr Leu Val Glu Asp Ala Pro Ser
    210                 215                 220

Gly Leu Val Pro Arg Gly Val Ser Gly Glu Gly Thr Val Arg Phe
225                 230                 235                 240

Ala Pro Gly Ser Thr His His His His His
                245                 250

<210> SEQ ID NO 4
<211> LENGTH: 249
<212> TYPE: PRT
<213> ORGANISM: Artificial Sequence
<220> FEATURE:
<223> OTHER INFORMATION: protease construct

<400> SEQUENCE: 4

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
```

```
                    20                  25                  30

Glu Arg Leu Phe Gly Ile Gly Phe Gly Pro Tyr Ile Ile Ala Asn Gln
                35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
                100                 105                 110

Cys Met Val Ser Thr Asn Phe Gln Gln Lys Ser Val Ser Ser Leu Val
                115                 120                 125

Ser Glu Ser Ser His Ile Val His Met Arg Asp Thr Ser Phe Trp Gln
                130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
                180                 185                 190

Tyr Leu Asp Ala Ala Asp Gly Trp Cys Lys Asn Trp Lys Phe Asn Ala
                195                 200                 205

Asp Lys Ile Ser Trp Gly Ser Phe Ile Leu Trp Glu Asp Ser Gly Leu
                210                 215                 220

Val Pro Arg Gly Val Ser Gly Glu Gly Glu Tyr Val Arg Phe Gly Pro
225                 230                 235                 240

Gly Ser Thr His His His His His His
                245

<210> SEQ ID NO 5
<211> LENGTH: 249
<212> TYPE: PRT
<213> ORGANISM: Artificial Sequence
<220> FEATURE:
<223> OTHER INFORMATION: protease construct

<400> SEQUENCE: 5

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
                20                  25                  30

Glu Arg Leu Phe Gly Ile Gly Phe Gly Pro Tyr Ile Ile Ala Asn Gln
                35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
                100                 105                 110

Cys Met Val Ser Thr Asn Phe Gln Gln Lys Ser Val Ser Ser Leu Val
                115                 120                 125

Ser Glu Ser Ser His Ile Val His Met Arg Asp Thr Ser Phe Trp Gln
```

```
              130                 135                 140
His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Asp Ser Gly Leu
    210                 215                 220

Val Pro Arg Gly Val Ser Gly Glu Gly Glu Tyr Val Arg Phe Ala Pro
225                 230                 235                 240

Gly Ser Thr His His His His His His
                245

<210> SEQ ID NO 6
<211> LENGTH: 253
<212> TYPE: PRT
<213> ORGANISM: Artificial Sequence
<220> FEATURE:
<223> OTHER INFORMATION: protease construct

<400> SEQUENCE: 6

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
            100                 105                 110

Cys Met Val Ser Thr Asn Phe Gln Gln Lys Ser Val Ser Ser Leu Val
        115                 120                 125

Ser Glu Ser Ser His Ile Val His Lys Glu Asp Thr Ser Phe Trp Gln
    130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Tyr Leu Tyr Glu Asp Ala Pro Glu
    210                 215                 220

Asp Phe Met Ser Gly Leu Val Pro Arg Gly Val Gly Arg Glu Tyr Val
225                 230                 235                 240

Arg Phe Ala Pro Gly Ser Thr His His His His His His
```

245         250

<210> SEQ ID NO 7
<211> LENGTH: 253
<212> TYPE: PRT
<213> ORGANISM: Artificial Sequence
<220> FEATURE:
<223> OTHER INFORMATION: protease construct

<400> SEQUENCE: 7

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
            100                 105                 110

Cys Met Val Ser Thr Asn Phe Gln Gln Lys Ser Val Ser Ser Leu Val
        115                 120                 125

Ser Glu Ser Ser His Ile Val His Lys Glu Asp Thr Ser Phe Trp Gln
    130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Asp Ala Pro Glu
    210                 215                 220

Asp Phe Met Ser Gly Leu Val Pro Arg Gly Val Gly Arg Glu Tyr Val
225                 230                 235                 240

Arg Phe Ala Pro Gly Ser Thr His His His His His His
                245                 250

<210> SEQ ID NO 8
<211> LENGTH: 253
<212> TYPE: PRT
<213> ORGANISM: Artificial Sequence
<220> FEATURE:
<223> OTHER INFORMATION: protease construct

<400> SEQUENCE: 8

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
            50                  55                  60

Gly Glu Phe Lys Val Lys Asn Ser Thr Gln Leu Gln Met Lys Pro Val
 65                  70                  75                  80

Glu Gly Arg Asp Ile Ile Val Ile Lys Met Ala Lys Asp Phe Pro Pro
                 85                  90                  95

Phe Pro Gln Lys Leu Lys Phe Arg Gln Pro Thr Ile Lys Asp Arg Val
                100                 105                 110

Cys Met Val Ser Thr Asn Phe Gln Gln Lys Ser Val Ser Ser Leu Val
                115                 120                 125

Ser Glu Ser Ser His Ile Val His Lys Glu Asp Thr Ser Phe Trp Gln
        130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                    165                 170                 175

Asn Gly Ser Asn Tyr Phe Val Glu Phe Pro Glu Lys Phe Val Ala Thr
                180                 185                 190

Tyr Leu Asp Ala Ala Asp Gly Trp Cys Lys Asn Trp Lys Phe Asn Ala
            195                 200                 205

Asp Lys Ile Ser Trp Gly Ser Phe Ile Leu Trp Glu Asp Ala Pro Glu
        210                 215                 220

Asp Phe Met Gly Gly Ile Glu Gly Arg Ser Gly Arg Glu Tyr Val
225                 230                 235                 240

Arg Phe Ala Pro Gly Ser Thr His His His His His His
                245                 250

<210> SEQ ID NO 9
<211> LENGTH: 253
<212> TYPE: PRT
<213> ORGANISM: Artificial Sequence
<220> FEATURE:
<223> OTHER INFORMATION: protease construct

<400> SEQUENCE: 9

Ser Ser Gly Ser Lys Ala Leu Leu Lys Gly Val Arg Asp Phe Asn Pro
 1               5                  10                  15

Ile Ser Ala Cys Val Cys Leu Leu Glu Asn Ser Ser Asp Gly His Ser
                20                  25                  30

Glu Arg Leu Phe Gly Ile Gly Phe Gly Pro Tyr Ile Ile Ala Asn Gln
            35                  40                  45

His Leu Phe Arg Arg Asn Asn Gly Glu Leu Thr Ile Lys Thr Met His
        50                  55                  60

Gly Glu Phe Lys Val Lys Asn Ser Thr Gln Leu Gln Met Lys Pro Val
 65                  70                  75                  80

Glu Gly Arg Asp Ile Ile Val Ile Lys Met Ala Lys Asp Phe Pro Pro
                 85                  90                  95

Phe Pro Gln Lys Leu Lys Phe Arg Gln Pro Thr Ile Lys Asp Arg Val
                100                 105                 110

Cys Met Val Ser Thr Asn Phe Gln Gln Lys Ser Val Ser Ser Leu Val
                115                 120                 125

Ser Glu Ser Ser His Ile Val His Lys Glu Asp Thr Ser Phe Trp Gln
        130                 135                 140

His Trp Ile Thr Thr Lys Asp Gly Gln Cys Gly Ser Pro Leu Val Ser
145                 150                 155                 160

```
Ile Ile Asp Gly Asn Ile Leu Gly Ile His Ser Leu Thr His Thr Thr
            165                 170                 175
Asn Gly Ser Asn Tyr Phe Val Glu Phe Pro Glu Lys Phe Val Ala Thr
        180                 185                 190
Tyr Leu Asp Ala Ala Asp Gly Trp Cys Lys Asn Trp Lys Phe Asn Ala
            195                 200                 205
Asp Lys Ile Ser Trp Gly Ser Phe Ile Leu Trp Glu Asp Ala Pro Glu
        210                 215                 220
Asp Gly Gly Arg Pro Leu Ala Leu Trp Arg Ser Gly Arg Glu Tyr Val
225                 230                 235                 240
Arg Phe Ala Pro Gly Ser Thr His His His His His His
            245                 250
```

<210> SEQ ID NO 10
<211> LENGTH: 253
<212> TYPE: PRT
<213> ORGANISM: Artificial Sequence
<220> FEATURE:
<223> OTHER INFORMATION: protease construct

<400> SEQUENCE: 10

```
Ser Ser Gly Ser Lys Ala Leu Leu Lys Gly Val Arg Asp Phe Asn Pro
1               5                   10                  15
Ile Ser Ala Cys Val Cys Leu Leu Glu Asn Ser Ser Asp Gly His Ser
            20                  25                  30
Glu Arg Leu Phe Gly Ile Gly Phe Gly Pro Tyr Ile Ile Ala Asn Gln
        35                  40                  45
His Leu Phe Arg Arg Asn Asn Gly Glu Leu Thr Ile Lys Thr Met His
    50                  55                  60
Gly Glu Phe Lys Val Lys Asn Ser Thr Gln Leu Gln Met Lys Pro Val
65                  70                  75                  80
Glu Gly Arg Asp Ile Ile Val Ile Lys Met Ala Lys Asp Phe Pro Pro
                85                  90                  95
Phe Pro Gln Lys Leu Lys Phe Arg Gln Pro Thr Ile Lys Asp Arg Val
            100                 105                 110
Cys Met Val Ser Thr Asn Phe Gln Gln Lys Ser Val Ser Ser Leu Val
        115                 120                 125
Ser Glu Ser Ser His Ile Val His Lys Glu Asp Thr Ser Phe Trp Gln
    130                 135                 140
His Trp Ile Thr Thr Lys Asp Gly Gln Cys Gly Ser Pro Leu Val Ser
145                 150                 155                 160
Ile Ile Asp Gly Asn Ile Leu Gly Ile His Ser Leu Thr His Thr Thr
                165                 170                 175
Asn Gly Ser Asn Tyr Phe Val Glu Phe Pro Glu Lys Phe Val Ala Thr
            180                 185                 190
Tyr Leu Asp Ala Ala Asp Gly Trp Cys Lys Asn Trp Lys Phe Asn Ala
        195                 200                 205
Asp Lys Ile Ser Trp Gly Ser Phe Ile Leu Trp Glu Asp Ala Pro Gly
    210                 215                 220
Gly Leu Arg Leu Ser Ser Tyr Tyr Ser Gly Ala Gly Arg Glu Tyr Val
225                 230                 235                 240
Arg Phe Ala Pro Gly Ser Thr His His His His His His
                245                 250
```

<210> SEQ ID NO 11
<211> LENGTH: 253

```
<212> TYPE: PRT
<213> ORGANISM: Artificial Sequence
<220> FEATURE:
<223> OTHER INFORMATION: protease construct

<400> SEQUENCE: 11

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
            100                 105                 110

Cys Met Val Ser Thr Asn Phe Gln Gln Lys Ser Val Ser Ser Leu Val
        115                 120                 125

Ser Glu Ser Ser His Ile Val His Lys Glu Asp Thr Ser Phe Trp Gln
130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Asp Ala Pro Gly
    210                 215                 220

Gly Glu His Ser Ser Lys Leu Gln Ser Gly Ala Gly Arg Glu Tyr Val
225                 230                 235                 240

Arg Phe Ala Pro Gly Ser Thr His His His His His His
                245                 250

<210> SEQ ID NO 12
<211> LENGTH: 253
<212> TYPE: PRT
<213> ORGANISM: Artificial Sequence
<220> FEATURE:
<223> OTHER INFORMATION: protease construct

<400> SEQUENCE: 12

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80
```

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
            100                 105                 110

Cys Met Val Ser Thr Asn Phe Gln Gln Lys Ser Val Ser Ser Leu Val
        115                 120                 125

Ser Glu Ser Ser His Ile Val His Lys Glu Asp Thr Ser Phe Trp Gln
130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Asp Ala Pro Gly
    210                 215                 220

Gly Leu Arg Leu Ser Ser Tyr Tyr Ser Gly Ala Gly Arg Glu Tyr Val
225                 230                 235                 240

Arg Phe Ala Pro Gly Ser Thr His His His His His His
                245                 250

<210> SEQ ID NO 13
<211> LENGTH: 246
<212> TYPE: PRT
<213> ORGANISM: Artificial Sequence
<220> FEATURE:
<223> OTHER INFORMATION: protease construct

<400> SEQUENCE: 13

Ser Met Ser Thr Ser Gly Ser Gly Ser Gly Ser Ala Lys Gly Ser Val
1               5                   10                  15

Val Ile Val Gly Arg Ile Asn Leu Ser Gly Asp Thr Ala Tyr Ser Gln
            20                  25                  30

Gln Thr Arg Gly Ala Ala Gly Ile Ala Ala Thr Ser Ala Thr Gly Arg
        35                  40                  45

Asp Lys Asn Gln Val Asp Gly Glu Val Gln Val Leu Ser Thr Ala Thr
    50                  55                  60

Gln Ser Phe Leu Ala Thr Cys Val Asn Gly Val Cys Trp Thr Val Tyr
65                  70                  75                  80

His Gly Ala Gly Ser Lys Thr Leu Ala Gly Pro Lys Gly Pro Ile Thr
                85                  90                  95

Gln Met Tyr Thr Asn Val Asp Gln Asp Leu Val Gly Trp Pro Ala Pro
            100                 105                 110

Pro Gly Ala Arg Ser Met Thr Pro Cys Thr Cys Gly Ser Ser Asp Leu
        115                 120                 125

Tyr Leu Val Thr Arg His Ala Asp Val Ile Pro Val Arg Arg Arg Gly
    130                 135                 140

Asp Ser Arg Gly Ser Leu Leu Ser Pro Arg Pro Val Ser Tyr Leu Lys
145                 150                 155                 160

Gly Ser Ser Gly Gly Pro Leu Leu Cys Pro Ser Gly His Val Val Gly
                165                 170                 175

Ile Phe Arg Ala Ala Val Cys Thr Arg Gly Val Ala Lys Ala Val Asp
            180                 185                 190

```
Phe Ile Pro Val Glu Ser Met Glu Thr Thr Met Arg Gly Gly Gly
            195                 200                 205

Ser Gly Gly Glu Thr Val Arg Phe Gln Ser Gly Ser Gly Gly Asp
    210                 215                 220

Glu Leu Ile Leu Cys Pro Leu Asp Leu Gly Gly Ser Gly Gly Thr Gly
225                 230                 235                 240

His His His His His His
                245

<210> SEQ ID NO 14
<211> LENGTH: 390
<212> TYPE: PRT
<213> ORGANISM: Artificial Sequence
<220> FEATURE:
<223> OTHER INFORMATION: protease construct

<400> SEQUENCE: 14

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
            100                 105                 110

Cys Met Val Ser Thr Asn Phe Gln Gln Lys Ser Val Ser Ser Leu Val
        115                 120                 125

Ser Glu Ser Ser His Ile Val His Lys Glu Asp Thr Ser Phe Trp Gln
    130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Asp Ala Pro Gly
    210                 215                 220

Gly Glu His Ser Ser Lys Leu Gln Ser Gly Ala Gly Arg Glu Tyr Val
225                 230                 235                 240

Arg Phe Ala Pro Gly Gly Ser Gly Gly Ser Gly Gly Ser Gly Gly Ser
                245                 250                 255

Gly Gly Ser Gly Gly Asp Val Leu Gln Glu Ser Gly Gly Gly Ser
            260                 265                 270

Val Gln Ala Gly Gly Ser Leu Arg Leu Ser Cys Val Ala Ser Gly Trp
        275                 280                 285

Ile Tyr Ile Pro Pro Cys Met Ala Trp Phe Arg Gln Ala Pro Gly Lys
    290                 295                 300
```

```
Glu Arg Glu Arg Val Ala Thr Ile Asn Pro Ser Gly Arg Thr Tyr Tyr
305                 310                 315                 320

Ala Asp Ser Thr Lys Gly Arg Phe Arg Ile Ser Gln Asp Asn Val Lys
            325                 330                 335

Arg Thr Leu Tyr Leu Tyr Met Asn Ser Leu Lys Pro Glu Asp Thr Ala
            340                 345                 350

Thr Tyr Tyr Cys Ala Ala Asp Asp Gly Thr Cys Pro Arg Met Glu Phe
            355                 360                 365

Asp Asp Trp Gly Gln Gly Thr Gln Val Thr Val Ser Ser Gly Gly Ser
    370                 375                 380

His His His His His His
385                 390

<210> SEQ ID NO 15
<211> LENGTH: 390
<212> TYPE: PRT
<213> ORGANISM: Artificial Sequence
<220> FEATURE:
<223> OTHER INFORMATION: protease construct

<400> SEQUENCE: 15

Ser Gly Gly Asp Val Gln Leu Gln Glu Ser Gly Gly Ser Val Gln
1               5                   10                  15

Ala Gly Gly Ser Leu Arg Leu Ser Cys Val Ala Ser Gly Trp Ile Tyr
            20                  25                  30

Ile Pro Pro Cys Met Ala Trp Phe Arg Gln Ala Pro Gly Lys Glu Arg
            35                  40                  45

Glu Arg Val Ala Thr Ile Asn Pro Ser Gly Arg Thr Tyr Tyr Ala Asp
    50                  55                  60

Ser Thr Lys Gly Arg Phe Arg Ile Ser Gln Asp Asn Val Lys Arg Thr
65                  70                  75                  80

Leu Tyr Leu Tyr Met Asn Ser Leu Lys Pro Glu Asp Thr Ala Thr Tyr
                85                  90                  95

Tyr Cys Ala Ala Asp Asp Gly Thr Cys Pro Arg Met Glu Phe Asp Asp
            100                 105                 110

Trp Gly Gln Gly Thr Gln Val Thr Val Ser Ser Gly Gly Ser Gly Gly
            115                 120                 125

Ser Gly Gly Ser Gly Gly Ser Gly Gly Ser Gly Gly Ser Lys Ala Leu
    130                 135                 140

Leu Lys Gly Val Arg Asp Phe Asn Pro Ile Ser Ala Cys Val Cys Leu
145                 150                 155                 160

Leu Glu Asn Ser Ser Asp Gly His Ser Glu Arg Leu Phe Gly Ile Gly
                165                 170                 175

Phe Gly Pro Tyr Ile Ile Ala Asn Gln His Leu Phe Arg Arg Asn Asn
            180                 185                 190

Gly Glu Leu Thr Ile Lys Thr Met His Gly Glu Phe Lys Val Lys Asn
            195                 200                 205

Ser Thr Gln Leu Gln Met Lys Pro Val Glu Gly Arg Asp Ile Ile Val
    210                 215                 220

Ile Lys Met Ala Lys Asp Phe Pro Pro Phe Pro Gln Lys Leu Lys Phe
225                 230                 235                 240

Arg Gln Pro Thr Ile Lys Asp Arg Val Cys Met Val Ser Thr Asn Phe
                245                 250                 255

Gln Gln Lys Ser Val Ser Ser Leu Val Ser Glu Ser Ser His Ile Val
            260                 265                 270
```

```
His Lys Glu Asp Thr Ser Phe Trp Gln His Trp Ile Thr Thr Lys Asp
            275                 280                 285

Gly Gln Cys Gly Ser Pro Leu Val Ser Ile Ile Asp Gly Asn Ile Leu
            290                 295                 300

Gly Ile His Ser Leu Thr His Thr Thr Asn Gly Ser Asn Tyr Phe Val
305                 310                 315                 320

Glu Phe Pro Glu Lys Phe Val Ala Thr Tyr Leu Asp Ala Ala Asp Gly
                325                 330                 335

Trp Cys Lys Asn Trp Lys Phe Asn Ala Asp Lys Ile Ser Trp Gly Ser
            340                 345                 350

Phe Ile Leu Trp Glu Asp Ala Pro Gly Gly His Ser Ser Lys Leu
            355                 360                 365

Gln Ser Gly Ala Gly Arg Glu Tyr Val Arg Phe Ala Pro Gly Ser Thr
370                 375                 380

His His His His His His
385                 390

<210> SEQ ID NO 16
<211> LENGTH: 344
<212> TYPE: PRT
<213> ORGANISM: Artificial Sequence
<220> FEATURE:
<223> OTHER INFORMATION: protease construct

<400> SEQUENCE: 16

Ser Gly Gly Ser Gly Ala Glu Tyr Val Arg Ala Leu Phe Asp Phe Asn
1               5                   10                  15

Gly Asn Asp Glu Glu Asp Leu Pro Phe Lys Lys Gly Asp Ile Leu Arg
                20                  25                  30

Ile Arg Asp Lys Pro Glu Glu Gln Trp Trp Asn Ala Gly Asp Ser Glu
            35                  40                  45

Gly Lys Arg Gly Met Ile Pro Val Pro Tyr Val Glu Lys Tyr Arg Pro
50                  55                  60

Ala Ser Ala Ser Val Ser Ala Leu Ile Gly Gly Arg Gly Gly Ser Gly
65                  70                  75                  80

Gly Ser Gly Gly Ser Gly Gly Ser Gly Gly Ser Gly Gly Ser Ser Lys
                85                  90                  95

Ala Leu Leu Lys Gly Val Arg Asp Phe Asn Pro Ile Ser Ala Cys Val
                100                 105                 110

Cys Leu Leu Glu Asn Ser Ser Asp Gly His Ser Glu Arg Leu Phe Gly
            115                 120                 125

Ile Gly Phe Gly Pro Tyr Ile Ile Ala Asn Gln His Leu Phe Arg Arg
130                 135                 140

Asn Asn Gly Glu Leu Thr Ile Lys Thr Met His Gly Glu Phe Lys Val
145                 150                 155                 160

Lys Asn Ser Thr Gln Leu Gln Met Lys Pro Val Glu Gly Arg Asp Ile
                165                 170                 175

Ile Val Ile Lys Met Ala Lys Asp Phe Pro Pro Phe Pro Gln Lys Leu
            180                 185                 190

Lys Phe Arg Gln Pro Thr Ile Lys Asp Arg Val Cys Met Val Ser Thr
        195                 200                 205

Asn Phe Gln Gln Lys Ser Val Ser Ser Leu Val Ser Glu Ser Ser His
    210                 215                 220

Ile Val His Lys Glu Asp Thr Ser Phe Trp Gln His Trp Ile Thr Thr
225                 230                 235                 240
```

```
Lys Asp Gly Gln Cys Gly Ser Pro Leu Val Ser Ile Ile Asp Gly Asn
            245                 250                 255

Ile Leu Gly Ile His Ser Leu Thr His Thr Thr Asn Gly Ser Asn Tyr
            260                 265                 270

Phe Val Glu Phe Pro Glu Lys Phe Val Ala Thr Tyr Leu Asp Ala Ala
            275                 280                 285

Asp Gly Trp Cys Lys Asn Trp Lys Phe Asn Ala Asp Lys Ile Ser Trp
            290                 295                 300

Gly Ser Phe Ile Leu Trp Glu Asp Ala Pro Glu Asp Phe Met Ser Gly
305                 310                 315                 320

Leu Val Pro Arg Gly Val Gly Arg Glu Tyr Val Arg Phe Ala Pro Gly
            325                 330                 335

Ser Thr His His His His His His
            340

<210> SEQ ID NO 17
<211> LENGTH: 261
<212> TYPE: PRT
<213> ORGANISM: Artificial Sequence
<220> FEATURE:
<223> OTHER INFORMATION: protease construct

<400> SEQUENCE: 17

Ser Met Ser Thr Ser Gly Pro Pro Pro Leu Pro Pro Lys Arg Arg
1               5                   10                  15

Arg Gly Gly Ser Gly Gly Ser Gly Gly Ser Ala Lys Gly Ser Val Val
                20                  25                  30

Ile Val Gly Arg Ile Asn Leu Ser Gly Asp Thr Ala Tyr Ser Gln Gln
            35                  40                  45

Thr Arg Gly Ala Ala Gly Ile Ala Ala Thr Ser Ala Thr Gly Arg Asp
        50                  55                  60

Lys Asn Gln Val Asp Gly Glu Val Gln Val Leu Ser Thr Ala Thr Gln
65                  70                  75                  80

Ser Phe Leu Ala Thr Cys Val Asn Gly Val Cys Trp Thr Val Tyr His
                85                  90                  95

Gly Ala Gly Ser Lys Thr Leu Ala Gly Pro Lys Gly Pro Ile Thr Gln
            100                 105                 110

Met Tyr Thr Asn Val Asp Gln Asp Leu Val Gly Trp Pro Ala Pro Pro
        115                 120                 125

Gly Ala Arg Ser Met Thr Pro Cys Thr Cys Gly Ser Ser Asp Leu Tyr
130                 135                 140

Leu Val Thr Arg His Ala Asp Val Ile Pro Val Arg Arg Arg Gly Asp
145                 150                 155                 160

Ser Arg Gly Ser Leu Leu Ser Pro Arg Pro Val Ser Tyr Leu Lys Gly
                165                 170                 175

Ser Ser Gly Gly Pro Leu Leu Cys Pro Ser Gly His Val Val Gly Ile
            180                 185                 190

Phe Arg Ala Ala Val Cys Thr Arg Gly Val Ala Lys Ala Val Asp Phe
        195                 200                 205

Ile Pro Val Glu Ser Met Glu Thr Thr Met Arg Gly Gly Gly Ser
    210                 215                 220

Gly Gly Glu Thr Val Arg Phe Gln Ser Gly Gly Ser Gly Gly Asp Glu
225                 230                 235                 240

Leu Ile Leu Cys Pro Leu Asp Leu Gly Gly Ser Gly Thr Gly His
                245                 250                 255
```

His His His His His
            260

<210> SEQ ID NO 18
<211> LENGTH: 263
<212> TYPE: PRT
<213> ORGANISM: Artificial Sequence
<220> FEATURE:
<223> OTHER INFORMATION: protease construct

<400> SEQUENCE: 18

Ser Met Ser Thr Ser Gly Ser Gly Ser Ala Lys Gly Ser Val
1               5                   10                  15

Val Ile Val Gly Arg Ile Asn Leu Ser Gly Asp Thr Ala Tyr Ser Gln
            20                  25                  30

Gln Thr Arg Gly Ala Ala Gly Ile Ala Ala Thr Ser Ala Thr Gly Arg
        35                  40                  45

Asp Lys Asn Gln Val Asp Gly Glu Val Gln Val Leu Ser Thr Ala Thr
50                  55                  60

Gln Ser Phe Leu Ala Thr Cys Val Asn Gly Val Cys Trp Thr Val Tyr
65                  70                  75                  80

His Gly Ala Gly Ser Lys Thr Leu Ala Gly Pro Lys Gly Pro Ile Thr
                85                  90                  95

Gln Met Tyr Thr Asn Val Asp Gln Asp Leu Val Gly Trp Pro Ala Pro
            100                 105                 110

Pro Gly Ala Arg Ser Met Thr Pro Cys Thr Cys Gly Ser Ser Asp Leu
        115                 120                 125

Tyr Leu Val Thr Arg His Ala Asp Val Ile Pro Val Arg Arg Arg Gly
130                 135                 140

Asp Ser Arg Gly Ser Leu Leu Ser Pro Arg Pro Val Ser Tyr Leu Lys
145                 150                 155                 160

Gly Ser Ser Gly Gly Pro Leu Leu Cys Pro Ser Gly His Val Val Gly
                165                 170                 175

Ile Phe Arg Ala Ala Val Cys Thr Arg Gly Val Ala Lys Ala Val Asp
            180                 185                 190

Phe Ile Pro Val Glu Ser Met Glu Thr Thr Met Arg Gly Gly Ser Gly
        195                 200                 205

Gly Ser Gly Gly Glu Thr Val Arg Phe Gln Ser Gly Gly Ser Gly Gly
    210                 215                 220

Asp Glu Leu Ile Leu Cys Pro Leu Asp Leu Gly Gly Ser Gly Gly Ser
225                 230                 235                 240

Gly Gly Pro Pro Pro Pro Leu Pro Pro Lys Arg Arg Arg Gly Gly Thr
                245                 250                 255

Gly His His His His His His
            260

<210> SEQ ID NO 19
<211> LENGTH: 382
<212> TYPE: PRT
<213> ORGANISM: Artificial Sequence
<220> FEATURE:
<223> OTHER INFORMATION: protease construct

<400> SEQUENCE: 19

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser

```
            20                  25                  30
Glu Arg Leu Phe Gly Ile Gly Phe Gly Pro Tyr Ile Ile Ala Asn Gln
            35                  40                  45

His Leu Phe Arg Arg Asn Asn Gly Glu Leu Thr Ile Lys Thr Met His
        50                  55                  60

Gly Glu Phe Lys Val Lys Asn Ser Thr Gln Leu Gln Met Lys Pro Val
 65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
                100                 105                 110

Cys Met Val Ser Thr Asn Phe Gln Gln Lys Ser Val Ser Ser Leu Val
            115                 120                 125

Ser Glu Ser Ser His Ile Val His Lys Glu Asp Thr Ser Phe Trp Gln
        130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Asp Ala Pro Glu
    210                 215                 220

Asp Phe Met Ser Gly Leu Val Pro Arg Gly Val Gly Arg Glu Tyr Val
225                 230                 235                 240

Arg Phe Ala Pro Ala Ser Ser Ser Gly Thr Ala Gln His Asp Glu
                245                 250                 255

Ala Val Asp Asn Lys Phe Asn Lys Glu Gln Gln Asn Ala Phe Tyr Glu
            260                 265                 270

Ile Leu His Leu Pro Asn Leu Asn Glu Glu Gln Arg Asn Ala Phe Ile
        275                 280                 285

Gln Ser Leu Lys Asp Asp Pro Ser Gln Ser Ala Asn Leu Leu Ala Glu
    290                 295                 300

Ala Lys Lys Leu Asn Asp Ala Gln Ala Pro Lys Val Asp Asn Lys Phe
305                 310                 315                 320

Asn Lys Glu Gln Gln Asn Ala Phe Tyr Glu Ile Leu His Leu Pro Asn
                325                 330                 335

Leu Asn Glu Glu Gln Arg Asn Ala Phe Ile Gln Ser Leu Lys Asp Asp
            340                 345                 350

Pro Ser Gln Ser Ala Asn Leu Leu Ala Glu Ala Lys Lys Leu Asn Asp
        355                 360                 365

Ala Gln Ala Pro Lys Gly Ser Thr His His His His His His
    370                 375                 380

<210> SEQ ID NO 20
<211> LENGTH: 379
<212> TYPE: PRT
<213> ORGANISM: Artificial Sequence
<220> FEATURE:
<223> OTHER INFORMATION: protease construct

<400> SEQUENCE: 20

Ala Gln His Asp Glu Ala Val Asp Asn Lys Phe Asn Lys Glu Gln Gln
```

```
  1               5                   10                  15
Asn Ala Phe Tyr Glu Ile Leu His Leu Pro Asn Leu Asn Glu Glu Gln
                 20                  25                  30
Arg Asn Ala Phe Ile Gln Ser Leu Lys Asp Asp Pro Ser Gln Ser Ala
                 35                  40                  45
Asn Leu Leu Ala Glu Ala Lys Lys Leu Asn Asp Ala Gln Ala Pro Lys
 50                  55                  60
Val Asp Asn Lys Phe Asn Lys Glu Gln Gln Asn Ala Phe Tyr Glu Ile
 65                  70                  75                  80
Leu His Leu Pro Asn Leu Asn Glu Glu Gln Arg Asn Ala Phe Ile Gln
                 85                  90                  95
Ser Leu Lys Asp Asp Pro Ser Gln Ser Ala Asn Leu Leu Ala Glu Ala
                100                 105                 110
Lys Lys Leu Asn Asp Ala Gln Ala Pro Lys Ala Ser Ser Ser Ser Gly
                115                 120                 125
Thr Ser Lys Ala Leu Leu Lys Gly Val Arg Asp Phe Asn Pro Ile Ser
130                 135                 140
Ala Cys Val Cys Leu Leu Glu Asn Ser Ser Asp Gly His Ser Glu Arg
145                 150                 155                 160
Leu Phe Gly Ile Gly Phe Gly Pro Tyr Ile Ile Ala Asn Gln His Leu
                165                 170                 175
Phe Arg Arg Asn Asn Gly Glu Leu Thr Ile Lys Thr Met His Gly Glu
                180                 185                 190
Phe Lys Val Lys Asn Ser Thr Gln Leu Gln Met Lys Pro Val Glu Gly
                195                 200                 205
Arg Asp Ile Ile Val Ile Lys Met Ala Lys Asp Phe Pro Pro Phe Pro
210                 215                 220
Gln Lys Leu Lys Phe Arg Gln Pro Thr Ile Lys Asp Arg Val Cys Met
225                 230                 235                 240
Val Ser Thr Asn Phe Gln Gln Lys Ser Val Ser Ser Leu Val Ser Glu
                245                 250                 255
Ser Ser His Ile Val His Lys Glu Asp Thr Ser Phe Trp Gln His Trp
                260                 265                 270
Ile Thr Thr Lys Asp Gly Gln Cys Gly Ser Pro Leu Val Ser Ile Ile
                275                 280                 285
Asp Gly Asn Ile Leu Gly Ile His Ser Leu Thr His Thr Thr Asn Gly
                290                 295                 300
Ser Asn Tyr Phe Val Glu Phe Pro Glu Lys Phe Val Ala Thr Tyr Leu
305                 310                 315                 320
Asp Ala Ala Asp Gly Trp Cys Lys Asn Trp Lys Phe Asn Ala Asp Lys
                325                 330                 335
Ile Ser Trp Gly Ser Phe Ile Leu Trp Glu Asp Ala Pro Glu Asp Phe
                340                 345                 350
Met Ser Gly Leu Val Pro Arg Gly Val Gly Arg Glu Tyr Val Arg Phe
                355                 360                 365
Ala Pro Gly Ser Thr His His His His His His
370                 375
```

<210> SEQ ID NO 21
<211> LENGTH: 440
<212> TYPE: PRT
<213> ORGANISM: Artificial Sequence
<220> FEATURE:
<223> OTHER INFORMATION: protease construct

```
<400> SEQUENCE: 21

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
            100                 105                 110

Cys Met Val Ser Thr Asn Phe Gln Gln Lys Ser Val Ser Ser Leu Val
            115                 120                 125

Ser Glu Ser Ser His Ile Val His Lys Glu Asp Thr Ser Phe Trp Gln
130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Asp Ala Pro Glu
210                 215                 220

Asp Ser Gly Ser Pro Glu Leu Gly Phe Ser Ile Ser Gly Gly Val Gly
225                 230                 235                 240

Gly Arg Gly Asn Pro Phe Arg Pro Asp Asp Asp Gly Ile Phe Val Thr
                245                 250                 255

Arg Val Gln Pro Glu Gly Pro Ala Ser Lys Leu Leu Gln Pro Gly Asp
            260                 265                 270

Lys Ile Ile Gln Ala Asn Gly Tyr Ser Phe Ile Asn Ile Glu His Gly
        275                 280                 285

Gln Ala Val Ser Leu Leu Lys Thr Phe Gln Asn Thr Val Glu Leu Ile
    290                 295                 300

Ile Val Arg Glu Val Gly Asn Gly Ala Lys Gln Glu Ile Arg Val Arg
305                 310                 315                 320

Val Glu Lys Asp Gly Gly Ser Gly Gly Val Ser Ser Val Pro Thr Asn
                325                 330                 335

Leu Glu Val Val Ala Ala Thr Pro Thr Ser Leu Leu Ile Ser Trp Asp
            340                 345                 350

Ala Tyr Arg Glu Leu Pro Val Ser Tyr Tyr Arg Ile Thr Tyr Gly Glu
        355                 360                 365

Thr Gly Gly Asn Ser Pro Val Gln Glu Phe Thr Val Pro Gly Ser Lys
    370                 375                 380

Ser Thr Ala Thr Ile Ser Gly Leu Lys Pro Gly Val Asp Tyr Thr Ile
385                 390                 395                 400

Thr Val Tyr Ala His Tyr Asn Tyr His Tyr Tyr Ser Ser Pro Ile Ser
                405                 410                 415
```

```
Ile Asn Tyr Arg Gly Pro Gly Arg Glu Tyr Val Arg Phe Ala Pro Gly
                420                 425                 430

Ser Thr His His His His His
            435                 440
```

<210> SEQ ID NO 22
<211> LENGTH: 436
<212> TYPE: PRT
<213> ORGANISM: Artificial Sequence
<220> FEATURE:
<223> OTHER INFORMATION: protease construct

<400> SEQUENCE: 22

```
Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
            100                 105                 110

Cys Met Val Ser Thr Asn Phe Gln Gln Lys Ser Val Ser Ser Leu Val
        115                 120                 125

Ser Glu Ser Ser His Ile Val His Lys Glu Asp Thr Ser Phe Trp Gln
    130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Ser Gly Ser Pro
    210                 215                 220

Glu Leu Gly Phe Ser Ile Ser Gly Val Gly Gly Arg Gly Asn Pro
225                 230                 235                 240

Phe Arg Pro Asp Asp Asp Gly Ile Phe Val Thr Arg Val Gln Pro Glu
                245                 250                 255

Gly Pro Ala Ser Lys Leu Leu Gln Pro Gly Asp Lys Ile Ile Gln Ala
            260                 265                 270

Asn Gly Tyr Ser Phe Ile Asn Ile Glu His Gly Gln Ala Val Ser Leu
        275                 280                 285

Leu Lys Thr Phe Gln Asn Thr Val Glu Leu Ile Ile Val Arg Glu Val
    290                 295                 300

Gly Asn Gly Ala Lys Gln Glu Ile Arg Val Arg Val Glu Lys Asp Gly
305                 310                 315                 320

Gly Ser Gly Gly Gly Val Ser Ser Val Pro Thr Asn Leu Glu Val Val
                325                 330                 335
```

```
Ala Ala Thr Pro Thr Ser Leu Leu Ile Ser Trp Asp Ala Tyr Arg Glu
            340                 345                 350

Leu Pro Val Ser Tyr Tyr Arg Ile Thr Tyr Gly Glu Thr Gly Gly Asn
        355                 360                 365

Ser Pro Val Gln Glu Phe Thr Val Pro Gly Ser Lys Ser Thr Ala Thr
    370                 375                 380

Ile Ser Gly Leu Lys Pro Gly Val Asp Tyr Thr Ile Thr Val Tyr Ala
385                 390                 395                 400

His Tyr Asn Tyr His Tyr Tyr Ser Ser Pro Ile Ser Ile Asn Tyr Arg
                405                 410                 415

Gly Pro Gly Arg Glu Tyr Val Arg Phe Ala Pro Gly Ser Thr His His
            420                 425                 430

His His His His
        435

<210> SEQ ID NO 23
<211> LENGTH: 441
<212> TYPE: PRT
<213> ORGANISM: Artificial Sequence
<220> FEATURE:
<223> OTHER INFORMATION: protease construct

<400> SEQUENCE: 23

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
            100                 105                 110

Cys Met Val Ser Thr Asn Phe Gln Gln Lys Ser Val Ser Ser Leu Val
        115                 120                 125

Ser Glu Ser Ser His Ile Val His Lys Glu Asp Thr Ser Phe Trp Gln
    130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Ser Gly Ser Pro
    210                 215                 220

Glu Leu Gly Phe Ser Ile Ser Gly Gly Val Gly Gly Arg Gly Asn Pro
225                 230                 235                 240

Phe Arg Pro Asp Asp Asp Gly Ile Phe Val Thr Arg Val Gln Pro Glu
                245                 250                 255
```

```
Gly Pro Ala Ser Lys Leu Leu Gln Pro Gly Asp Lys Ile Ile Gln Ala
            260                 265                 270

Asn Gly Tyr Ser Phe Ile Asn Ile Glu His Gly Gln Ala Val Ser Leu
        275                 280                 285

Leu Lys Thr Phe Gln Asn Thr Val Glu Leu Ile Ile Val Arg Glu Val
    290                 295                 300

Gly Asn Gly Ala Lys Gln Glu Ile Arg Val Arg Val Glu Lys Asp Gly
305                 310                 315                 320

Gly Ser Gly Gly Gly Ser Gly Gly Ser Val Ser Val Pro Thr
                325                 330                 335

Asn Leu Glu Val Val Ala Ala Thr Pro Thr Ser Leu Leu Ile Ser Trp
            340                 345                 350

Asp Ala Tyr Arg Glu Leu Pro Val Ser Tyr Tyr Arg Ile Thr Tyr Gly
        355                 360                 365

Glu Thr Gly Gly Asn Ser Pro Val Gln Glu Phe Thr Val Pro Gly Ser
    370                 375                 380

Lys Ser Thr Ala Thr Ile Ser Gly Leu Lys Pro Gly Val Asp Tyr Thr
385                 390                 395                 400

Ile Thr Val Tyr Ala His Tyr Asn Tyr His Tyr Tyr Ser Ser Pro Ile
            405                 410                 415

Ser Ile Asn Tyr Arg Gly Pro Gly Arg Glu Tyr Val Arg Phe Ala Pro
        420                 425                 430

Gly Ser Thr His His His His His His
            435                 440

<210> SEQ ID NO 24
<211> LENGTH: 442
<212> TYPE: PRT
<213> ORGANISM: Artificial Sequence
<220> FEATURE:
<223> OTHER INFORMATION: protease construct

<400> SEQUENCE: 24

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
            85                  90                  95

Phe Pro Gln Lys Leu Lys Phe Arg Gln Pro Thr Ile Lys Asp Arg Val
        100                 105                 110

Cys Met Val Ser Thr Asn Phe Gln Gln Lys Ser Val Ser Ser Leu Val
    115                 120                 125

Ser Glu Ser Ser His Ile Val His Lys Glu Asp Thr Ser Phe Trp Gln
130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
            165                 170                 175
```

```
Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Gly Ser Gly Ser
    210                 215                 220

Pro Glu Leu Gly Phe Ser Ile Ser Gly Val Gly Gly Arg Gly Asn
225                 230                 235                 240

Pro Phe Arg Pro Asp Asp Gly Ile Phe Val Thr Arg Val Gln Pro
                245                 250                 255

Glu Gly Pro Ala Ser Lys Leu Leu Gln Pro Gly Asp Lys Ile Ile Gln
            260                 265                 270

Ala Asn Gly Tyr Ser Phe Ile Asn Ile Glu His Gly Gln Ala Val Ser
        275                 280                 285

Leu Leu Lys Thr Phe Gln Asn Thr Val Glu Leu Ile Ile Val Arg Glu
    290                 295                 300

Val Gly Asn Gly Ala Lys Gln Glu Ile Arg Val Arg Val Glu Lys Asp
305                 310                 315                 320

Gly Gly Ser Gly Gly Gly Ser Gly Gly Ser Val Ser Ser Val Pro
                325                 330                 335

Thr Asn Leu Glu Val Val Ala Ala Thr Pro Thr Ser Leu Leu Ile Ser
            340                 345                 350

Trp Asp Ala Tyr Arg Glu Leu Pro Val Ser Tyr Tyr Arg Ile Thr Tyr
        355                 360                 365

Gly Glu Thr Gly Gly Asn Ser Pro Val Gln Glu Phe Thr Val Pro Gly
    370                 375                 380

Ser Lys Ser Thr Ala Thr Ile Ser Gly Leu Lys Pro Gly Val Asp Tyr
385                 390                 395                 400

Thr Ile Thr Val Tyr Ala His Tyr Asn Tyr His Tyr Tyr Ser Ser Pro
                405                 410                 415

Ile Ser Ile Asn Tyr Arg Gly Pro Gly Arg Glu Tyr Val Arg Phe Ala
            420                 425                 430

Pro Gly Ser Thr His His His His His His
        435                 440

<210> SEQ ID NO 25
<211> LENGTH: 443
<212> TYPE: PRT
<213> ORGANISM: Artificial Sequence
<220> FEATURE:
<223> OTHER INFORMATION: protease construct

<400> SEQUENCE: 25

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95
```

Phe Pro Gln Lys Leu Lys Phe Arg Gln Pro Thr Ile Lys Asp Arg Val
              100                 105                 110

Cys Met Val Ser Thr Asn Phe Gln Gln Lys Ser Val Ser Ser Leu Val
              115                 120                 125

Ser Glu Ser Ser His Ile Val His Lys Glu Asp Thr Ser Phe Trp Gln
    130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Gly Gly Ser Gly
    210                 215                 220

Ser Pro Glu Leu Gly Phe Ser Ile Ser Gly Val Gly Gly Arg Gly
225                 230                 235                 240

Asn Pro Phe Arg Pro Asp Asp Gly Ile Phe Val Thr Arg Val Gln
                245                 250                 255

Pro Glu Gly Pro Ala Ser Lys Leu Leu Gln Pro Gly Asp Lys Ile Ile
            260                 265                 270

Gln Ala Asn Gly Tyr Ser Phe Ile Asn Ile Glu His Gly Gln Ala Val
        275                 280                 285

Ser Leu Leu Lys Thr Phe Gln Asn Thr Val Glu Leu Ile Ile Val Arg
    290                 295                 300

Glu Val Gly Asn Gly Ala Lys Gln Glu Ile Arg Val Arg Val Glu Lys
305                 310                 315                 320

Asp Gly Gly Ser Gly Gly Gly Ser Gly Gly Ser Val Ser Ser Val
                325                 330                 335

Pro Thr Asn Leu Glu Val Val Ala Ala Thr Pro Thr Ser Leu Leu Ile
            340                 345                 350

Ser Trp Asp Ala Tyr Arg Glu Leu Pro Val Ser Tyr Tyr Arg Ile Thr
        355                 360                 365

Tyr Gly Glu Thr Gly Gly Asn Ser Pro Val Gln Glu Phe Thr Val Pro
    370                 375                 380

Gly Ser Lys Ser Thr Ala Thr Ile Ser Gly Leu Lys Pro Gly Val Asp
385                 390                 395                 400

Tyr Thr Ile Thr Val Tyr Ala His Tyr Asn Tyr His Tyr Tyr Ser Ser
                405                 410                 415

Pro Ile Ser Ile Asn Tyr Arg Gly Pro Gly Arg Glu Tyr Val Arg Phe
            420                 425                 430

Ala Pro Gly Ser Thr His His His His His His
        435                 440

<210> SEQ ID NO 26
<211> LENGTH: 444
<212> TYPE: PRT
<213> ORGANISM: Artificial Sequence
<220> FEATURE:
<223> OTHER INFORMATION: protease construct

<400> SEQUENCE: 26

Ser Ser Gly Ser Lys Ala Leu Leu Lys Gly Val Arg Asp Phe Asn Pro
1               5                   10                  15

```
Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
            100                 105                 110

Cys Met Val Ser Thr Asn Phe Gln Gln Lys Ser Val Ser Ser Leu Val
            115                 120                 125

Ser Glu Ser Ser His Ile Val His Lys Glu Asp Thr Ser Phe Trp Gln
130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Gly Gly Gly Ser
    210                 215                 220

Gly Ser Pro Glu Leu Gly Phe Ser Ile Ser Gly Gly Val Gly Gly Arg
225                 230                 235                 240

Gly Asn Pro Phe Arg Pro Asp Asp Gly Ile Phe Val Thr Arg Val
                245                 250                 255

Gln Pro Glu Gly Pro Ala Ser Lys Leu Leu Gln Pro Gly Asp Lys Ile
            260                 265                 270

Ile Gln Ala Asn Gly Tyr Ser Phe Ile Asn Ile Glu His Gly Gln Ala
        275                 280                 285

Val Ser Leu Leu Lys Thr Phe Gln Asn Thr Val Glu Leu Ile Ile Val
    290                 295                 300

Arg Glu Val Gly Asn Gly Ala Lys Gln Glu Ile Arg Val Arg Val Glu
305                 310                 315                 320

Lys Asp Gly Gly Ser Gly Gly Gly Ser Gly Gly Ser Val Ser Ser
                325                 330                 335

Val Pro Thr Asn Leu Glu Val Val Ala Ala Thr Pro Thr Ser Leu Leu
            340                 345                 350

Ile Ser Trp Asp Ala Tyr Arg Glu Leu Pro Val Ser Tyr Tyr Arg Ile
        355                 360                 365

Thr Tyr Gly Glu Thr Gly Gly Asn Ser Pro Val Gln Glu Phe Thr Val
    370                 375                 380

Pro Gly Ser Lys Ser Thr Ala Thr Ile Ser Gly Leu Lys Pro Gly Val
385                 390                 395                 400

Asp Tyr Thr Ile Thr Val Tyr Ala His Tyr Asn Tyr His Tyr Tyr Ser
                405                 410                 415

Ser Pro Ile Ser Ile Asn Tyr Arg Gly Pro Gly Arg Gly Tyr Val Arg
            420                 425                 430
```

Phe Ala Pro Gly Ser Thr His His His His His
            435                 440

<210> SEQ ID NO 27
<211> LENGTH: 445
<212> TYPE: PRT
<213> ORGANISM: Artificial Sequence
<220> FEATURE:
<223> OTHER INFORMATION: protease construct

<400> SEQUENCE: 27

Ser Ser Gly Ser Lys Ala Leu Leu Lys Gly Val Arg Asp Phe Asn Pro
1               5                   10                  15

Ile Ser Ala Cys Val Cys Leu Leu Glu Asn Ser Ser Asp Gly His Ser
            20                  25                  30

Glu Arg Leu Phe Gly Ile Gly Phe Gly Pro Tyr Ile Ile Ala Asn Gln
        35                  40                  45

His Leu Phe Arg Arg Asn Asn Gly Glu Leu Thr Ile Lys Thr Met His
    50                  55                  60

Gly Glu Phe Lys Val Lys Asn Ser Thr Gln Leu Gln Met Lys Pro Val
65                  70                  75                  80

Glu Gly Arg Asp Ile Ile Val Ile Lys Met Ala Lys Asp Phe Pro Pro
                85                  90                  95

Phe Pro Gln Lys Leu Lys Phe Arg Gln Pro Thr Ile Lys Asp Arg Val
            100                 105                 110

Cys Met Val Ser Thr Asn Phe Gln Gln Lys Ser Val Ser Ser Leu Val
            115                 120                 125

Ser Glu Ser Ser His Ile Val His Lys Glu Asp Thr Ser Phe Trp Gln
        130                 135                 140

His Trp Ile Thr Thr Lys Asp Gly Gln Cys Gly Ser Pro Leu Val Ser
145                 150                 155                 160

Ile Ile Asp Gly Asn Ile Leu Gly Ile His Ser Leu Thr His Thr Thr
                165                 170                 175

Asn Gly Ser Asn Tyr Phe Val Glu Phe Pro Glu Lys Phe Val Ala Thr
            180                 185                 190

Tyr Leu Asp Ala Ala Asp Gly Trp Cys Lys Asn Trp Lys Phe Asn Ala
        195                 200                 205

Asp Lys Ile Ser Trp Gly Ser Phe Ile Leu Trp Glu Gly Gly Ser Gly
    210                 215                 220

Ser Gly Ser Pro Glu Leu Gly Phe Ser Ile Ser Gly Val Gly Gly
225                 230                 235                 240

Arg Gly Asn Pro Phe Arg Pro Asp Asp Asp Gly Ile Phe Val Thr Arg
                245                 250                 255

Val Gln Pro Glu Gly Pro Ala Ser Lys Leu Leu Gln Pro Gly Asp Lys
            260                 265                 270

Ile Ile Gln Ala Asn Gly Tyr Ser Phe Ile Asn Ile Glu His Gly Gln
        275                 280                 285

Ala Val Ser Leu Leu Lys Thr Phe Gln Asn Thr Val Glu Leu Ile Ile
    290                 295                 300

Val Arg Glu Val Gly Asn Gly Ala Lys Gln Glu Ile Arg Val Arg Val
305                 310                 315                 320

Glu Lys Asp Gly Gly Ser Gly Gly Gly Ser Gly Gly Ser Val Ser
                325                 330                 335

Ser Val Pro Thr Asn Leu Glu Val Val Ala Ala Thr Pro Thr Ser Leu
            340                 345                 350

```
Leu Ile Ser Trp Asp Ala Tyr Arg Glu Leu Pro Val Ser Tyr Tyr Arg
            355                 360                 365

Ile Thr Tyr Gly Glu Thr Gly Gly Asn Ser Pro Val Gln Glu Phe Thr
        370                 375                 380

Val Pro Gly Ser Lys Ser Thr Ala Thr Ile Ser Gly Leu Lys Pro Gly
385                 390                 395                 400

Val Asp Tyr Thr Ile Thr Val Tyr Ala His Tyr Asn Tyr His Tyr Tyr
                405                 410                 415

Ser Ser Pro Ile Ser Ile Asn Tyr Arg Gly Pro Gly Arg Glu Tyr Val
                420                 425                 430

Arg Phe Ala Pro Gly Ser Thr His His His His His
        435                 440                 445

<210> SEQ ID NO 28
<211> LENGTH: 528
<212> TYPE: PRT
<213> ORGANISM: Artificial Sequence
<220> FEATURE:
<223> OTHER INFORMATION: protease construct

<400> SEQUENCE: 28

Ser Gly Gly Ser Gly Ala Glu Tyr Val Arg Ala Leu Phe Asp Phe Asn
1               5                   10                  15

Gly Asn Asp Glu Glu Asp Leu Pro Phe Lys Lys Gly Asp Ile Leu Arg
            20                  25                  30

Ile Arg Asp Lys Pro Glu Glu Gln Trp Trp Asn Ala Glu Asp Ser Glu
        35                  40                  45

Gly Lys Arg Gly Met Ile Pro Val Pro Tyr Val Glu Lys Tyr Arg Pro
50                  55                  60

Ala Ser Ala Ser Val Ser Ala Leu Ile Gly Gly Arg Gly Gly Ser Gly
65                  70                  75                  80

Gly Ser Gly Gly Ser Gly Gly Ser Gly Gly Ser Gly Gly Ser Ser Lys
                85                  90                  95

Ala Leu Leu Lys Gly Val Arg Asp Phe Asn Pro Ile Ser Ala Cys Val
            100                 105                 110

Cys Leu Leu Glu Asn Ser Ser Asp Gly His Ser Glu Arg Leu Phe Gly
        115                 120                 125

Ile Gly Phe Gly Pro Tyr Ile Ile Ala Asn Gln His Leu Phe Arg Arg
130                 135                 140

Asn Asn Gly Glu Leu Thr Ile Lys Thr Met His Gly Glu Phe Lys Val
145                 150                 155                 160

Lys Asn Ser Thr Gln Leu Gln Met Lys Pro Val Glu Gly Arg Asp Ile
                165                 170                 175

Ile Val Ile Lys Met Ala Lys Asp Phe Pro Pro Phe Pro Gln Lys Leu
            180                 185                 190

Lys Phe Arg Gln Pro Thr Ile Lys Asp Arg Val Cys Met Val Ser Thr
        195                 200                 205

Asn Phe Gln Gln Lys Ser Val Ser Ser Leu Val Ser Glu Ser Ser His
210                 215                 220

Ile Val His Lys Glu Asp Thr Ser Phe Trp Gln His Trp Ile Thr Thr
225                 230                 235                 240

Lys Asp Gly Gln Cys Gly Ser Pro Leu Val Ser Ile Ile Asp Gly Asn
                245                 250                 255

Ile Leu Gly Ile His Ser Leu Thr His Thr Thr Asn Gly Ser Asn Tyr
            260                 265                 270
```

Phe Val Glu Phe Pro Glu Lys Phe Val Ala Thr Tyr Leu Asp Ala Ala
                275                 280                 285

Asp Gly Trp Cys Lys Asn Trp Lys Phe Asn Ala Asp Lys Ile Ser Trp
            290                 295                 300

Gly Ser Phe Ile Leu Trp Glu Ser Gly Ser Pro Glu Leu Gly Phe Ser
305                 310                 315                 320

Ile Ser Gly Gly Val Gly Gly Arg Gly Asn Pro Phe Arg Pro Asp Asp
                325                 330                 335

Asp Gly Ile Phe Val Thr Arg Val Gln Pro Glu Pro Ala Ser Lys
            340                 345                 350

Leu Leu Gln Pro Gly Asp Lys Ile Ile Gln Ala Asn Gly Tyr Ser Phe
        355                 360                 365

Ile Asn Ile Glu His Gly Gln Ala Val Ser Leu Leu Lys Thr Phe Gln
        370                 375                 380

Asn Thr Val Glu Leu Ile Ile Val Arg Glu Val Gly Asn Gly Ala Lys
385                 390                 395                 400

Gln Glu Ile Arg Val Arg Val Glu Lys Asp Gly Gly Ser Gly Gly Gly
                405                 410                 415

Gly Val Ser Ser Val Pro Thr Asn Leu Glu Val Ala Ala Thr Pro
            420                 425                 430

Thr Ser Leu Leu Ile Ser Trp Asp Ala Tyr Arg Glu Leu Pro Val Ser
    435                 440                 445

Tyr Tyr Arg Ile Thr Tyr Gly Glu Thr Gly Gly Asn Ser Pro Val Gln
            450                 455                 460

Glu Phe Thr Val Pro Gly Ser Lys Ser Thr Ala Thr Ile Ser Gly Leu
465                 470                 475                 480

Lys Pro Gly Val Asp Tyr Thr Ile Thr Val Tyr Ala His Tyr Asn Tyr
                485                 490                 495

His Tyr Tyr Ser Ser Pro Ile Ser Ile Asn Tyr Arg Gly Pro Gly Arg
            500                 505                 510

Glu Tyr Val Arg Phe Ala Pro Gly Ser Thr His His His His His
        515                 520                 525

<210> SEQ ID NO 29
<211> LENGTH: 759
<212> TYPE: DNA
<213> ORGANISM: Artificial Sequence
<220> FEATURE:
<223> OTHER INFORMATION: protease construct

<400> SEQUENCE: 29
tctagtggtt ctaaagcttt gctgaagggc gtgcgcgatt taatccgat ctctgcttgc      60 gtatgcctgc tggaaaactc ctcggatggt catagtgaac gtctgtttgg cattggtttt     120
ggcccgtata tcattgccaa ccagcatctg tttcgtcgta caatggcga actgaccatc     180 aaaaccatgc atggtgaatt caaagtcaaa aactctaccc agctgcagat gaaaccggtt     240
gaaggccgtg acattatcgt tatcaaaatg gctaaagact cccgccgtt cccgcagaaa      300 ctgaaattcc gtcagccgac catcaaagat cgtgtgtgca tggtgtccac caactttcag     360
cagaaaagcg tctcgagcct ggtgtctgaa tcctctcaca ttgtgcataa agaagacact     420
tctttctggc agcactggat caccactaaa gatggccagt gtggcagccc actagtttcc     480
atcattgatg caacattct gggcatccac agcctgactc ataccaccaa cggtagcaac      540
tacttcgtgg aatttccgga aaaattcgtg gcgacttatc tagatgccgc ggatggttgg     600
tgcaaaaact ggaaattcaa cgcggataaa atcagctggg gttccttac cctggttgaa     660

```
gatgcgccgg aagacttcat gagtggtctg gtgccgcgcg gtgtaggtcg cgaaaccgtg    720
cgctttgccc cgggaagcac ccaccaccat catcatcac                           759
```

<210> SEQ ID NO 30
<211> LENGTH: 753
<212> TYPE: DNA
<213> ORGANISM: Artificial Sequence
<220> FEATURE:
<223> OTHER INFORMATION: protease construct

<400> SEQUENCE: 30

```
tctagtggtt ctaaagcttt gctgaagggc gtgcgcgatt ttaatccgat ctctgcttgc    60
gtatgcctgc tggaaaactc ctcggatggt catagtgaac gtctgtttgg cattggtttt   120
ggcccgtata tcattgccaa ccagcatctg tttcgtcgta acaatggcga actgaccatc   180
aaaaccatgc atggtgaatt caaagtcaaa aactctaccc agctgcagat gaaaccggtt   240
gaaggccgtg acattatcgt tatcaaaatg gctaaagact cccgccgtt cccgcagaaa    300 ctgaaattcc gtcagccgac catcaaagat cgtgtgtgca tggtgtccac caactttcag   360
cagaaaagcg tctcgagcct ggtgtctgaa tcctctcaca ttgtgcatat gagagatact   420
tctttctggc agcactggat caccactaaa gatggccagt gtggcagccc actagtttcc   480
atcattgatg caacattct gggcatccac agcctgactc ataccaccaa cggtagcaac    540
tacttcgtgg aatttccgga aaaattcgtg gcgacttatc tagatgccgc ggatggttgg   600
tgcaaaaact ggaaattcaa cgcggataaa atcagctggg gttcctttac cctggttgaa   660
gatgcgccga gtggtctggt gccgcgcggt gtaagtggtg aaggtgaaac cgtgcgcttt   720
ggcccgggaa gcacccacca ccatcatcat cac                                753
```

<210> SEQ ID NO 31
<211> LENGTH: 753
<212> TYPE: DNA
<213> ORGANISM: Artificial Sequence
<220> FEATURE:
<223> OTHER INFORMATION: protease construct

<400> SEQUENCE: 31

```
tctagtggtt ctaaagcttt gctgaagggc gtgcgcgatt ttaatccgat ctctgcttgc    60
gtatgcctgc tggaaaactc ctcggatggt catagtgaac gtctgtttgg cattggtttt   120
ggcccgtata tcattgccaa ccagcatctg tttcgtcgta acaatggcga actgaccatc   180
aaaaccatgc atggtgaatt caaagtcaaa aactctaccc agctgcagat gaaaccggtt   240
gaaggccgtg acattatcgt tatcaaaatg gctaaagact cccgccgtt cccgcagaaa    300 ctgaaattcc gtcagccgac catcaaagat cgtgtgtgca tggtgtccac caactttcag   360
cagaaaagcg tctcgagcct ggtgtctgaa tcctctcaca ttgtgcatat gagagatact   420
tctttctggc agcactggat caccactaaa gatggccagt gtggcagccc actagtttcc   480
atcattgatg caacattct gggcatccac agcctgactc ataccaccaa cggtagcaac    540
tacttcgtgg aatttccgga aaaattcgtg gcgacttatc tagatgccgc ggatggttgg   600
tgcaaaaact ggaaattcaa cgcggataaa atcagctggg gttcctttac cctggttgaa   660
gatgcgccga gtggtctggt gccgcgcggt gtaagtggtg aaggtgaaac cgtgcgcttt   720
gccccgggaa gcacccacca ccatcatcat cac                                753
```

<210> SEQ ID NO 32

<211> LENGTH: 747
<212> TYPE: DNA
<213> ORGANISM: Artificial Sequence
<220> FEATURE:
<223> OTHER INFORMATION: protease construct

<400> SEQUENCE: 32

```
tctagtggtt ctaaagcttt gctgaagggc gtgcgcgatt ttaatccgat ctctgcttgc    60
gtatgcctgc tggaaaactc ctcggatggt catagtgaac gtctgtttgg cattggtttt   120
ggcccgtata tcattgccaa ccagcatctg tttcgtcgta acaatggcga actgaccatc   180
aaaaccatgc atggtgaatt caaagtcaaa aactctaccc agctgcagat gaaaccggtt   240
gaaggccgtg acattatcgt tatcaaaatg gctaaagact cccgccgtt cccgcagaaa    300
ctgaaattcc gtcagccgac catcaaagat cgtgtgtgca tggtgtccac caactttcag   360
cagaaaagcg tctcgagcct ggtgtctgaa tcctctcaca ttgtgcatat gagagatact   420
tctttctggc agcactggat caccactaaa gatggccagt gtggcagccc actagtttcc   480
atcattgatg caacattct gggcatccac agcctgactc ataccaccaa cggtagcaac    540
tacttcgtgg aatttccgga aaaattcgtg gcgacttatc tagatgccgc ggatggttgg   600
tgcaaaaact ggaaattcaa cgcggataaa atcagctggg gatcgtttat cctgtgggaa   660
gatagtggtc tggtgccgcg cggtgtaagt ggtgaaggtg aatatgtgcg ctttggcccg   720
ggaagcaccc accaccatca tcatcac                                       747
```

<210> SEQ ID NO 33
<211> LENGTH: 747
<212> TYPE: DNA
<213> ORGANISM: Artificial Sequence
<220> FEATURE:
<223> OTHER INFORMATION: protease construct

<400> SEQUENCE: 33

```
tctagtggtt ctaaagcttt gctgaagggc gtgcgcgatt ttaatccgat ctctgcttgc    60
gtatgcctgc tggaaaactc ctcggatggt catagtgaac gtctgtttgg cattggtttt   120
ggcccgtata tcattgccaa ccagcatctg tttcgtcgta acaatggcga actgaccatc   180
aaaaccatgc atggtgaatt caaagtcaaa aactctaccc agctgcagat gaaaccggtt   240
gaaggccgtg acattatcgt tatcaaaatg gctaaagact cccgccgtt cccgcagaaa    300
ctgaaattcc gtcagccgac catcaaagat cgtgtgtgca tggtgtccac caactttcag   360
cagaaaagcg tctcgagcct ggtgtctgaa tcctctcaca ttgtgcatat gagagatact   420
tctttctggc agcactggat caccactaaa gatggccagt gtggcagccc actagtttcc   480
atcattgatg caacattct gggcatccac agcctgactc ataccaccaa cggtagcaac    540
tacttcgtgg aatttccgga aaaattcgtg gcgacttatc tagatgccgc ggatggttgg   600
tgcaaaaact ggaaattcaa cgcggataaa atcagctggg gatcgtttat cctgtgggaa   660
gatagtggtc tggtgccgcg cggtgtaagt ggtgaaggtg aatatgtgcg ctttgccccg   720
ggaagcaccc accaccatca tcatcac                                       747
```

<210> SEQ ID NO 34
<211> LENGTH: 759
<212> TYPE: DNA
<213> ORGANISM: Artificial Sequence
<220> FEATURE:
<223> OTHER INFORMATION: protease construct

<400> SEQUENCE: 34

```
tctagtggtt ctaaagcttt gctgaagggc gtgcgcgatt ttaatccgat ctctgcttgc      60
gtatgcctgc tggaaaactc ctcggatggt catagtgaac gtctgtttgg cattggtttt     120
ggcccgtata tcattgccaa ccagcatctg tttcgtcgta acaatggcga actgaccatc     180
aaaaccatgc atggtgaatt caaagtcaaa aactctaccc agctgcagat gaaaccggtt     240
gaaggccgtg acattatcgt tatcaaaatg gctaaagact tcccgccgtt cccgcagaaa     300
ctgaaattcc gtcagccgac catcaaagat cgtgtgtgca tggtgtccac caactttcag     360
cagaaaagcg tctcgagcct ggtgtctgaa tcctctcaca ttgtgcataa agaagacact     420
tctttctggc agcactggat caccactaaa gatggccagt gtggcagccc actagtttcc     480
atcattgatg gcaacattct gggcatccac agcctgactc ataccaccaa cggtagcaac     540
tacttcgtgg aatttccgga aaaattcgtg gcgacttatc tagatgccgc ggatggttgg     600
tgcaaaaact ggaaattcaa cgcggataaa atcagctggg gttcctttta tctgtatgaa     660
gatgcgccgg aagacttcat gagtggtctg gtgccgcgcg tgtaggtcg cgaatatgtg      720 cgctttgccc cgggaagcac ccaccaccat catcatcac                            759
```

<210> SEQ ID NO 35
<211> LENGTH: 759
<212> TYPE: DNA
<213> ORGANISM: Artificial Sequence
<220> FEATURE:
<223> OTHER INFORMATION: protease construct

<400> SEQUENCE: 35

```
tctagtggtt ctaaagcttt gctgaagggc gtgcgcgatt ttaatccgat ctctgcttgc      60
gtatgcctgc tggaaaactc ctcggatggt catagtgaac gtctgtttgg cattggtttt     120
ggcccgtata tcattgccaa ccagcatctg tttcgtcgta acaatggcga actgaccatc     180
aaaaccatgc atggtgaatt caaagtcaaa aactctaccc agctgcagat gaaaccggtt     240
gaaggccgtg acattatcgt tatcaaaatg gctaaagact tcccgccgtt cccgcagaaa     300
ctgaaattcc gtcagccgac catcaaagat cgtgtgtgca tggtgtccac caactttcag     360
cagaaaagcg tctcgagcct ggtgtctgaa tcctctcaca ttgtgcataa agaagacact     420
tctttctggc agcactggat caccactaaa gatggccagt gtggcagccc actagtttcc     480
atcattgatg gcaacattct gggcatccac agcctgactc ataccaccaa cggtagcaac     540
tacttcgtgg aatttccgga aaaattcgtg gcgacttatc tagatgccgc ggatggttgg     600
tgcaaaaact ggaaattcaa cgcggataaa atcagctggg gttcctttat cctgtgggaa     660
gatgcgccgg aagacttcat gagtggtctg gtgccgcgcg tgtaggtcg cgaatatgtg      720 cgctttgccc cgggaagcac ccaccaccat catcatcac                            759
```

<210> SEQ ID NO 36
<211> LENGTH: 759
<212> TYPE: DNA
<213> ORGANISM: Artificial Sequence
<220> FEATURE:
<223> OTHER INFORMATION: protease construct

<400> SEQUENCE: 36

```
tctagtggtt ctaaagcttt gctgaagggc gtgcgcgatt ttaatccgat ctctgcttgc      60
gtatgcctgc tggaaaactc ctcggatggt catagtgaac gtctgtttgg cattggtttt     120
ggcccgtata tcattgccaa ccagcatctg tttcgtcgta acaatggcga actgaccatc     180
```

```
aaaaccatgc atggtgaatt caaagtcaaa aactctaccc agctgcagat gaaaccggtt    240
gaaggccgtg acattatcgt tatcaaaatg gctaaagact tcccgccgtt cccgcagaaa    300
ctgaaattcc gtcagccgac catcaaagat cgtgtgtgca tggtgtccac caactttcag    360
cagaaaagcg tctcgagcct ggtgtctgaa tcctctcaca ttgtgcataa agaagacact    420
tctttctggc agcactggat caccactaaa gatggccagt gtggcagccc actagtttcc    480
atcattgatg caacattct gggcatccac agcctgactc ataccaccaa cggtagcaac     540
tacttcgtgg aatttccgga aaaattcgtg gcgacttatc tagatgccgc ggatggttgg    600
tgcaaaaact ggaaattcaa cgcggataaa atcagctggg gttcctttat cctgtgggaa    660
gatgctccgg aagacttcat gggtggtatt gaaggtcgca gcggtggtcg cgaatatgtg    720
cgctttgccc cgggaagcac ccaccaccat catcatcac                           759

<210> SEQ ID NO 37
<211> LENGTH: 759
<212> TYPE: DNA
<213> ORGANISM: Artificial Sequence
<220> FEATURE:
<223> OTHER INFORMATION: protease construct

<400> SEQUENCE: 37
tctagtggtt ctaaagcttt gctgaagggc gtgcgcgatt ttaatccgat ctctgcttgc     60
gtatgcctgc tggaaaactc ctcggatggt catagtgaac gtctgtttgg cattggtttt    120
ggcccgtata tcattgccaa ccagcatctg tttcgtcgta acaatggcga actgaccatc    180
aaaaccatgc atggtgaatt caaagtcaaa aactctaccc agctgcagat gaaaccggtt    240
gaaggccgtg acattatcgt tatcaaaatg gctaaagact tcccgccgtt cccgcagaaa    300
ctgaaattcc gtcagccgac catcaaagat cgtgtgtgca tggtgtccac caactttcag    360
cagaaaagcg tctcgagcct ggtgtctgaa tcctctcaca ttgtgcataa agaagacact    420
tctttctggc agcactggat caccactaaa gatggccagt gtggcagccc actagtttcc    480
atcattgatg caacattct gggcatccac agcctgactc ataccaccaa cggtagcaac     540
tacttcgtgg aatttccgga aaaattcgtg gcgacttatc tagatgccgc ggatggttgg    600
tgcaaaaact ggaaattcaa cgcggataaa atcagctggg gttcctttat cctgtgggaa    660
gatgctcctg aaggtggtcg cccactggct ctgtggcgca gcggtggtcg cgaatatgtg    720
cgctttgccc cgggaagcac ccaccaccat catcatcac                           759

<210> SEQ ID NO 38
<211> LENGTH: 759
<212> TYPE: DNA
<213> ORGANISM: Artificial Sequence
<220> FEATURE:
<223> OTHER INFORMATION: protease construct

<400> SEQUENCE: 38
tctagtggtt ctaaagcttt gctgaagggc gtgcgcgatt ttaatccgat ctctgcttgc     60
gtatgcctgc tggaaaactc ctcggatggt catagtgaac gtctgtttgg cattggtttt    120
ggcccgtata tcattgccaa ccagcatctg tttcgtcgta acaatggcga actgaccatc    180
aaaaccatgc atggtgaatt caaagtcaaa aactctaccc agctgcagat gaaaccggtt    240
gaaggccgtg acattatcgt tatcaaaatg gctaaagact tcccgccgtt cccgcagaaa    300
ctgaaattcc gtcagccgac catcaaagat cgtgtgtgca tggtgtccac caactttcag    360
cagaaaagcg tctcgagcct ggtgtctgaa tcctctcaca ttgtgcataa agaagacact    420
```

| | |
|---|---|
| tctttctggc agcactggat caccactaaa gatggccagt gtggcagccc actagtttcc | 480 |
| atcattgatg gcaacattct gggcatccac agcctgactc ataccaccaa cggtagcaac | 540 |
| tacttcgtgg aatttccgga aaaattcgtg gcgacttatc tagatgccgc ggatggttgg | 600 |
| tgcaaaaact ggaaattcaa cgcggataaa atcagctggg gttcctttat cctgtgggaa | 660 |
| gatgctcctg gtggtagcgg caaaggtcct cgccagatta ccgcgggtcg cgaatatgtg | 720 |
| cgctttgccc cgggaagcac ccaccaccat catcatcac | 759 |

<210> SEQ ID NO 39
<211> LENGTH: 759
<212> TYPE: DNA
<213> ORGANISM: Artificial Sequence
<220> FEATURE:
<223> OTHER INFORMATION: protease construct

<400> SEQUENCE: 39

| | |
|---|---|
| tctagtggtt ctaaagcttt gctgaagggc gtgcgcgatt ttaatccgat ctctgcttgc | 60 |
| gtatgcctgc tggaaaactc ctcggatggt catagtgaac gtctgtttgg cattggtttt | 120 |
| ggcccgtata tcattgccaa ccagcatctg tttcgtcgta acaatggcga actgaccatc | 180 |
| aaaaccatgc atggtgaatt caaagtcaaa aactctaccc agctgcagat gaaaccggtt | 240 |
| gaaggccgtg acattatcgt tatcaaaatg gctaaagact tcccgccgtt cccgcagaaa | 300 |
| ctgaaattcc gtcagccgac catcaaagat cgtgtgtgca tggtgtccac caactttcag | 360 |
| cagaaaagcg tctcgagcct ggtgtctgaa tcctctcaca ttgtgcataa agaagacact | 420 |
| tctttctggc agcactggat caccactaaa gatggccagt gtggcagccc actagtttcc | 480 |
| atcattgatg gcaacattct gggcatccac agcctgactc ataccaccaa cggtagcaac | 540 |
| tacttcgtgg aatttccgga aaaattcgtg gcgacttatc tagatgccgc ggatggttgg | 600 |
| tgcaaaaact ggaaattcaa cgcggataaa atcagctggg gttcctttat cctgtgggaa | 660 |
| gatgctccgg gtggtgaaca tagcagcaaa ctgcagagcg gtgcgggtcg cgaatatgtg | 720 |
| cgctttgccc cgggaagcac ccaccaccat catcatcac | 759 |

<210> SEQ ID NO 40
<211> LENGTH: 759
<212> TYPE: DNA
<213> ORGANISM: Artificial Sequence
<220> FEATURE:
<223> OTHER INFORMATION: protease construct

<400> SEQUENCE: 40

| | |
|---|---|
| tctagtggtt ctaaagcttt gctgaagggc gtgcgcgatt ttaatccgat ctctgcttgc | 60 |
| gtatgcctgc tggaaaactc ctcggatggt catagtgaac gtctgtttgg cattggtttt | 120 |
| ggcccgtata tcattgccaa ccagcatctg tttcgtcgta acaatggcga actgaccatc | 180 |
| aaaaccatgc atggtgaatt caaagtcaaa aactctaccc agctgcagat gaaaccggtt | 240 |
| gaaggccgtg acattatcgt tatcaaaatg gctaaagact tcccgccgtt cccgcagaaa | 300 |
| ctgaaattcc gtcagccgac catcaaagat cgtgtgtgca tggtgtccac caactttcag | 360 |
| cagaaaagcg tctcgagcct ggtgtctgaa tcctctcaca ttgtgcataa agaagacact | 420 |
| tctttctggc agcactggat caccactaaa gatggccagt gtggcagccc actagtttcc | 480 |
| atcattgatg gcaacattct gggcatccac agcctgactc ataccaccaa cggtagcaac | 540 |
| tacttcgtgg aatttccgga aaaattcgtg gcgacttatc tagatgccgc ggatggttgg | 600 |

| | |
|---|---|
| tgcaaaaact ggaaattcaa cgcggataaa atcagctggg gttcctttat cctgtgggaa | 660 |
| gatgctccgg gtggtctgcg cctgagcagc tattatagcg gtgcgggtcg cgaatatgtg | 720 |
| cgctttgccc cgggaagcac ccaccaccat catcatcac | 759 |

<210> SEQ ID NO 41
<211> LENGTH: 738
<212> TYPE: DNA
<213> ORGANISM: Artificial Sequence
<220> FEATURE:
<223> OTHER INFORMATION: protease construct

<400> SEQUENCE: 41

| | |
|---|---|
| agcatgagca ctagtggcag cggcagtggc agcgctaaag gcagcgtcgt catcgtgggg | 60 |
| cgtatcaacc tgtctgggga cactgcatat tctcagcaga cccgtggcgc agcgggtatc | 120 |
| gcggcaactt ccgctaccgg ccgggacaaa aaccaggtgg atggcgaggt gcaggtgctt | 180 |
| tcaaccgcaa cacagtcttt tctggctaca tgcgtcaatg gggtttgttg gaccgtctat | 240 |
| cacggggccg gatccaagac acttgcgggt ccaaaaggcc ctattaccca gatgtacaca | 300 |
| aacgtggatc aagacctggt tgggtggccg gcaccaccgg gagctcgtag tatgacacct | 360 |
| tgcacttgtg gtagctccga tctgtatctg gtgacccgtc acgcagacgt cattccagtg | 420 |
| cgccgtcggg gagattcacg tggaagcctg ctgtccccac gtccagtctc ttacctgaag | 480 |
| ggcagtagtg gcggtccact gctgtgtcca tcaggacatg ttgtcggtat cttccgtgca | 540 |
| gcagtgtgca cccgtggcgt tgccaaggcg gttgatttta tccccgtgga gtccatggaa | 600 |
| actacaatgc ggggtggtgg tgggtctggc ggtgaaactg tgcgctttca atctggcggt | 660 |
| tctggtgggg atgaactgat tctgtgcccg ctggatctgg gtgggtctgg tgggactggg | 720 |
| catcatcatc atcaccac | 738 |

<210> SEQ ID NO 42
<211> LENGTH: 1170
<212> TYPE: DNA
<213> ORGANISM: Artificial Sequence
<220> FEATURE:
<223> OTHER INFORMATION: protease construct

<400> SEQUENCE: 42

| | |
|---|---|
| tctagtggtt ctaaagcttt gctgaagggc gtgcgcgatt ttaatccgat ctctgcttgc | 60 |
| gtatgcctgc tggaaaactc ctcggatggt catagtgaac gtctgtttgg cattggtttt | 120 |
| ggcccgtata tcattgccaa ccagcatctg tttcgtcgta caatggcgaa actgaccatc | 180 |
| aaaaccatgc atggtgaatt caaagtcaaa aactctaccc agctgcagat gaaaccggtt | 240 |
| gaaggccgtg acattatcgt tatcaaaatg gctaaagact tcccgccgtt cccgcagaaa | 300 |
| ctgaaattcc gtcagccgac catcaaagat cgtgtgtgca tggtgtccac caactttcag | 360 |
| cagaaaagcg tctcgagcct ggtgtctgaa tcctctcaca ttgtgcataa agaagacact | 420 |
| tctttctggc agcactggat caccactaaa gatggccagt gtggcagccc actagtttcc | 480 |
| atcattgatg gcaacattct gggcatccac agcctgactc ataccaccaa cggtagcaac | 540 |
| tacttcgtgg aatttccgga aaaattcgtg gcgacttatc tagatgccgc ggatggttgg | 600 |
| tgcaaaaact ggaaattcaa cgcggataaa atcagctggg gttcctttat cctgtgggaa | 660 |
| gatgctccgg gtggtgaaca tagcagcaaa ctgcagagcg gtgcgggtcg cgaatatgtg | 720 |
| cgctttgccc cgggtggttc tggcggtagt ggggtctg gtggctcggg cggttctggg | 780 |
| ggtgatgttc aactgcaaga aagcggtggt ggtagcgttc aagcgggtgg ttccctgcgc | 840 |

```
ctgtcgtgcg tcgcgtctgg ctggatttat attccgccgt gcatggcatg gtttcgtcag      900
gctccgggca aggaacgtga acgcgtcgcg accattaacc cgagtggccg cacctattac      960
gccgattcca cgaaaggtcg tttccgcatc agccaagaca acgttaagcg taccctgtat     1020
ctgtacatga atagcctgaa accggaagat accgcgacgt attactgcgc agcagatgat     1080
ggtacgtgcc cgcgcatgga atttgatgac tggggccagg gcacccaagt gacggttagc     1140
tctggcggta gccatcatca tcatcatcat                                       1170
```

<210> SEQ ID NO 43
<211> LENGTH: 1170
<212> TYPE: DNA
<213> ORGANISM: Artificial Sequence
<220> FEATURE:
<223> OTHER INFORMATION: protease construct

<400> SEQUENCE: 43

```
agcggcggtg atgttcaact gcaagaaagc ggtggtggta cgttcaagc gggtggttcc        60 ctgcgcctgt cgtgcgtcgc gtctggctgg atttatattc cgccgtgcat ggcatggttt      120
cgtcaggctc cgggcaagga acgtgaacgc gtcgcgacca ttaacccgag tggccgcacc      180
tattacgccg attccacgaa aggtcgtttc gcatcagcc aagacaacgt taagcgtacc       240
ctgtatctgt acatgaatag cctgaaaccg gaagataccg cgacgtatta ctgcgcagca      300
gatgatggta cgtgcccgcg catggaattt gatgactggg gccagggcac ccaagtgacg      360
gttagctctg gtggtagcgg cggtagcggc ggtagcggtg gctcgggcgg ttcgggcggt      420
tctaaagctt tgctgaaggg cgtgcgcgat tttaatccga tctctgcttg cgtatgcctg      480
ctggaaaact cctcggatgg tcatagtgaa cgtctgtttg cattggttt tggcccgtat       540 atcattgcca accagcatct gtttcgtcgt aacaatggcg aactgaccat caaaaccatg      600
catggtgaat tcaaagtcaa aaactctacc cagctgcaga tgaaaccggt tgaaggccgt      660
gacattatcg ttatcaaaat ggctaaagac ttcccgccgt tcccgcagaa actgaaattc      720
cgtcagccga ccatcaaaga tcgtgtgtgc atggtgtcca ccaactttca gcagaaaagc      780
gtctcgagcc tggtgtctga atcctctcac attgtgcata agaagacac ttctttctgg       840 cagcactgga tcaccactaa agatggccag tgtggcagcc cactagtttc catcattgat      900
ggcaacattc tgggcatcca cagcctgact cataccacca acgtagcaa ctacttcgtg       960 gaatttccgg aaaaattcgt ggcgacttat ctagatgccg cggatggttg gtgcaaaaac     1020
tggaaattca cgcggataa atcagctgg ggttccttta tcctgtggga agatgctccg       1080
ggtggtgaac atagcagcaa actgcagagc ggtgcgggtc gcgaatatgt gcgctttgcc     1140
ccgggaagca cccaccacca tcatcatcac                                      1170
```

<210> SEQ ID NO 44
<211> LENGTH: 1032
<212> TYPE: DNA
<213> ORGANISM: Artificial Sequence
<220> FEATURE:
<223> OTHER INFORMATION: protease construct

<400> SEQUENCE: 44

```
tctggtggtt ctggggcaga gtatgtgcgg gccctctttg actttaatgg gaatgatgaa        60
gaagatcttc catttaagaa aggagacatc ctgcgtatcc gggataagcc tgaagagcag      120
tggtggaatg cagaggacag cgaaggaaag cgtgggatga ttcctgtccc ttacgtggag      180
```

```
aagtatcgcc ctgcctccgc ctcagtatcg gctctgattg gaggtcgggg cggtagcggt      240
ggtagcggcg gtagcggcgg tagcggtggc tcgggcggtt cgtctaaagc tttgctgaag      300
ggcgtgcgcg attttaatcc gatctctgct tgcgtatgcc tgctggaaaa ctcctcggat      360
ggtcatagta aacgtctgtt tggcattggt tttggcccgt atatcattgc caaccagcat      420
ctgtttcgtc gtaacaatgg cgaactgacc atcaaaacca tgcatggtga attcaaagtc      480
aaaaactcta cccagctgca gatgaaaccg gttgaaggcc gtgacattat cgttatcaaa      540
atggctaaag acttcccgcc gttcccgcag aaactgaaat ccgtcagcc gaccatcaaa       600
gatcgtgtgt gcatggtgtc caccaacttt cagcagaaaa cgtctcgag cctggtgtct       660
gaatcctctc acattgtgca taagaagac acttctttct ggcagcactg gatcaccact       720
aaagatggcc agtgtggcag cccactagtt tccatcattg atggcaacat tctgggcatc      780
cacagcctga ctcataccac caacggtagc aactacttcg tggaatttcc ggaaaaattc      840
gtggcgactt atctagatgc cgcggatggt tggtgcaaaa actggaaatt caacgcggat      900
aaaatcagct ggggttcctt tatcctgtgg gaagatgcgc cggaagactt catgagtggt      960
ctggtgccgc gcggtgtagg tcgcgaatat gtgcgctttg ccccgggaag cacccaccac     1020
catcatcatc ac                                                        1032
```

<210> SEQ ID NO 45
<211> LENGTH: 783
<212> TYPE: DNA
<213> ORGANISM: Artificial Sequence
<220> FEATURE:
<223> OTHER INFORMATION: protease construct

<400> SEQUENCE: 45

```
agcatgagca ctagtggtcc tccgcctcct cttccgccta gcgtcgccg tggcggtagc        60
ggtggtagcg gtggcagcgc taaaggcagc gtcgtcatcg tggggcgtat caacctgtct      120
ggggacactg catattctca gcagacccgt ggcgcagcgg gtatcgcggc aacttccgct      180
accggccggg acaaaaacca ggtggatggc gaggtgcagg tgctttcaac cgcaacacag      240
tcttttctgg ctacatgcgt caatgggtt tgttggaccg tctatcacgg ggccggatcc       300
aagacacttg cgggtccaaa aggccctatt acccagatgt acacaaacgt ggatcaagac      360
ctggttgggt ggccggcacc accgggagct cgtagtatga caccttgcac ttgtggtagc      420
tccgatctgt atctggtgac ccgtcacgca gacgtcattc cagtgcgccg tcggggagat      480
tcacgtggaa gcctgctgtc cccacgtcca gtctcttacc tgaagggcag tagtggcggt      540
ccactgctgt gtccatcagg acatgttgtc ggtatcttcc gtgcagcagt gtgcacccgt      600
ggcgttgcca aggcggttga ttttatcccc gtggagtcca tggaaactac aatgcggggt      660
ggtggtgggt ctggcggtga aactgtgcgc tttcaatctg gcggttctgg tggggatgaa      720
ctgattctgt gcccgctgga tctgggtggg tctggtggga ctgggcatca tcatcatcac      780
cac                                                                   783
```

<210> SEQ ID NO 46
<211> LENGTH: 789
<212> TYPE: DNA
<213> ORGANISM: Artificial Sequence
<220> FEATURE:
<223> OTHER INFORMATION: protease construct

<400> SEQUENCE: 46

```
agcatgagca ctagtggcag cggcagtggc agcgctaaag gcagcgtcgt catcgtgggg       60
```

```
cgtatcaacc tgtctgggga cactgcatat tctcagcaga cccgtggcgc agcgggtatc      120
gcggcaactt ccgctaccgg ccgggacaaa aaccaggtgg atggcgaggt gcaggtgctt      180
tcaaccgcaa cacagtcttt tctggctaca tgcgtcaatg gggtttgttg gaccgtctat      240
cacggggccg gatccaagac acttgcgggt ccaaaaggcc ctattaccca gatgtacaca      300
aacgtggatc aagacctggt tgggtggccg gcaccaccgg gagctcgtag tatgacacct      360
tgcacttgtg gtagctccga tctgtatctg gtgacccgtc acgcagacgt cattccagtg      420
cgccgtcggg gagattcacg tggaagcctg ctgtccccac gtccagtctc ttacctgaag      480
ggcagtagtg gcggtccact gctgtgtcca tcaggacatg ttgtcggtat cttccgtgca      540
gcagtgtgca cccgtggcgt tgccaaggcg gttgatttta tccccgtgga gtccatggaa      600
actacaatgc ggggtggttc tggtgggtct ggcggtgaaa ctgtgcgctt tcaatctggc      660
ggttctggtg gggatgaact gattctgtgc ccgctggatc tgggtgggtc tggtgggtct      720
ggtgggcctc cgcctcctct tccgcctaag cgtcgccgtg gtgggactgg gcatcatcat      780
catcaccac                                                             789

<210> SEQ ID NO 47
<211> LENGTH: 1146
<212> TYPE: DNA
<213> ORGANISM: Artificial Sequence
<220> FEATURE:
<223> OTHER INFORMATION: protease construct

<400> SEQUENCE: 47
tctagtggtt ctaaagcttt gctgaagggc gtgcgcgatt ttaatccgat ctctgcttgc       60
gtatgcctgc tggaaaactc ctcggatggt catagtgaac gtctgtttgg cattggtttt      120
ggcccgtata tcattgccaa ccagcatctg tttcgtcgta caatggcga actgaccatc       180 aaaaccatgc atggtgaatt caaagtcaaa aactctaccc agctgcagat gaaaccggtt      240
gaaggccgtg acattatcgt tatcaaaatg gctaaagact tcccgccgtt cccgcagaaa      300
ctgaaattcc gtcagccgac catcaaagat cgtgtgtgca tggtgtccac caactttcag      360
cagaaaagcg tctcgagcct ggtgtctgaa tcctctcaca ttgtgcataa agaagacact      420 tcttttctggc agcactggat caccactaaa gatggccagt gtggcagccc actagtttcc      480
atcattgatg gcaacattct gggcatccac agcctgactc ataccaccaa cggtagcaac      540
tacttcgtgg aatttccgga aaaattcgtg gcgacttatc tagatgccgc ggatggttgg      600
tgcaaaaact ggaaattcaa cgcggataaa atcagctggg gttcctttat cctgtgggaa      660
gatgcgccgg aagacttcat gagtggtctg gtgccgcgcg gtgtaggtcg gaatatgtg       720 cgctttgccc cggctagcag tagcagcggt accgcgcaac acgatgaagc cgtagacaac      780
aaattcaaca agaacaaca aaacgcgttc tatgagatct acatttacc taacttaaac       840 gaagaacaac gaaacgcctt catccaaagt ttaaaagatg acccaagcca aagcgctaac      900
cttttagcag aagctaaaaa gctaaatgac gcacaagctc gaaggtaga caacaaattc      960 aacaagaac aacaaaacgc gttctatgag atcttacatt tacctaactt aaacgaagaa     1020
caacgaaacg ccttcatcca aagtttaaaa gatgacccaa gccaaagcgc taacctttta     1080
gcagaagcta aaaagctaaa tgatgctcag gcgccgaaag aagcaccca ccaccatcat      1140 catcac                                                                1146

<210> SEQ ID NO 48
```

<211> LENGTH: 1137
<212> TYPE: DNA
<213> ORGANISM: Artificial Sequence
<220> FEATURE:
<223> OTHER INFORMATION: protease construct

<400> SEQUENCE: 48

```
gcgcaacacg atgaagccgt agacaacaaa ttcaacaaag aacaacaaaa cgcgttctat      60
gagatcttac atttacctaa cttaaacgaa gaacaacgaa acgccttcat ccaaagttta     120
aaagatgacc caagccaaag cgctaacctt ttagcagaag ctaaaaagct aaatgacgca     180
caagctccga aggtagacaa caaattcaac aaagaacaac aaaacgcgtt ctatgagatc     240
ttacatttac ctaacttaaa cgaagaacaa cgaaacgcct catccaaagt ttaaaagat     300
gacccaagcc aaagcgctaa ccttttagca gaagctaaaa agctaaatga tgctcaggcg     360
ccgaaagcta gcagtagcag cggtacctct aaagctttgc tgaagggcgt gcgcgatttt     420
aatccgatct ctgcttgcgt atgcctgctg gaaaactcct cggatggtca tagtgaacgt     480
ctgtttggca ttggttttgg cccgtatatc attgccaacc agcatctgtt tcgtcgtaac     540
aatggcgaac tgaccatcaa accatgcat ggtgaattca agtcaaaaa ctctacccag      600
ctgcagatga accggttga aggccgtgac attatcgtta tcaaaatggc taagacttc      660
ccgccgttcc gcagaaact gaaattccgt cagccgacca tcaaagatcg tgtgtgcatg      720
gtgtccacca ctttcagca gaaaagcgtc tcgagcctgg tgtctgaatc ctctcacatt     780
gtgcataaag aagacacttc tttctggcag cactggatca ccactaaaga tggccagtgt     840
ggcagcccac tagtttccat cattgatggc aacattctgg catccacag cctgactcat      900
accaccaacg gtagcaacta cttcgtggaa tttccggaaa aattcgtggc gacttatcta     960
gatgccgcgg atggttggtg caaaaactgg aaattcaacg cggataaaat cagctggggt    1020
tcctttatcc tgtgggaaga tgcgccggaa gacttcatga tggtctggt gccgcgcggt    1080
gtaggtcgcg aatatgtgcg ctttgccccg ggaagcaccc accaccatca tcatcac     1137
```

<210> SEQ ID NO 49
<211> LENGTH: 1320
<212> TYPE: DNA
<213> ORGANISM: Artificial Sequence
<220> FEATURE:
<223> OTHER INFORMATION: protease construct

<400> SEQUENCE: 49

```
tctagtggtt ctaaagcttt gctgaagggc gtgcgcgatt ttaatccgat ctctgcttgc      60
gtatgcctgc tggaaaactc ctcggatggt catagtgaac gtctgtttgg cattggtttt     120
ggcccgtata tcattgccaa ccagcatctg tttcgtcgta acaatggcga actgaccatc     180
aaaccatgc atggtgaatt caaagtcaaa aactctaccc agctgcagat gaaaccggtt     240
gaaggccgtg acattatcgt tatcaaaatg gctaagact tccgccgtt cccgcagaaa      300
ctgaaattcc gtcagccgac catcaaagat cgtgtgtgca tggtgtccac caactttcag     360
cagaaaagcg tctcgagcct ggtgtctgaa tcctctcaca ttgtgcataa agaagacact     420
tctttctggc agcactggat caccactaaa gatggccagt gtggcagccc actagtttcc     480
atcattgatg gcaacattct gggcatccac agcctgactc ataccaccaa cggtagcaac     540
tacttcgtgg aatttccgga aaaattcgtg gcgacttatc tagatgccgc ggatggttgg     600
tgcaaaaact ggaaattcaa cgcggataaa atcagctggg gttcctttat cctgtgggaa     660
gatgcgccgg aagatagtgg tagtccggag ttaggtttta gtatttcagg tggtgtcggt     720
```

```
ggtcgtggga atcctttcg tccagatgat gatggaattt tcgttacgcg tgtccagccg      780
gagggcccag ctagcaagct gctgcaacct ggggataaaa tcattcaagc taacggttat      840
agctttatca acattgaaca tggccaagct gtcagcttac tgaaaaccctt tcagaacaca     900 gtcgaactga ttatcgttcg cgaggtgggt aatggtgcca agcaggaaat ccgcgttcgc      960
gtggagaagg atggcggcag tggtgggtt tcttctgtgc cgactaacct ggaagttgtc      1020
gcggccactc ctacaagtct gctgattagc tgggatgcct atcgtgaact gccggttct      1080 tattaccgca tcacgtacgg tgagacaggc ggtaatagtc ctgttcaaga gtttactgta     1140
cctggtagca aaagcaccgc gactattagt gggctgaagc cggagtgga ttacaccatc     1200 accgtatatg ctcattataa ttatcactac tatagctcac cgatcagcat taactatcgt    1260
ggtcctggtc gcgaatatgt gcgctttgcc ccgggaagca cccaccacca tcatcatcac    1320
```

<210> SEQ ID NO 50
<211> LENGTH: 1308
<212> TYPE: DNA
<213> ORGANISM: Artificial Sequence
<220> FEATURE:
<223> OTHER INFORMATION: protease construct

<400> SEQUENCE: 50

```
tctagtggtt ctaaagcttt gctgaagggc gtgcgcgatt ttaatccgat ctctgcttgc       60
gtatgcctgc tggaaaactc ctcggatggt catagtgaac gtctgtttgg cattggtttt     120
ggcccgtata tcattgccaa ccagcatctg tttcgtcgta caatggcga actgaccatc      180 aaaaccatgc atggtgaatt caaagtcaaa aactctaccc agctgcagat gaaaccggtt     240
gaaggccgtg acattatcgt tatcaaaatg gctaaagact cccgccgtt cccgcagaaa     300 ctgaaattcc gtcagccgac catcaaagat cgtgtgtgca tggtgtccac caactttcag    360
cagaaaagcg tctcgagcct ggtgtctgaa tcctctcaca ttgtgcataa agaagacact    420
tctttctggc agcactggat caccactaaa gatggccagt gtggcagccc actagtttcc    480
atcattgatg caacattctg gcatccac agcctgactc ataccaccaa cggtagcaac      540
tacttcgtgg aatttccgga aaaattcgtg gcgacttatc tagatgccgc ggatggttgg   600
tgcaaaaact ggaaattcaa cgcggataaa atcagctggg gttcctttat cctgtgggaa    660
agtggtagtc cggagttagg ttttagtatt tcaggtggtg tcggtggtcg tgggaatcct    720
tttcgtccag atgatgatgg aattttcgtt acgcgtgtcc agccggaggg cccagctagc    780
aagctgctgc aacctgggga taaaatcatt caagctaacg ttatagctt tatcaacatt   840 gaacatggcc aagctgtcag cttactgaaa accctttcaga acacagtcga actgattatc  900
gttcgcgagg tgggtaatgg tgccaagcag gaaatccgcg ttcgcgtgga aaggatggc     960 ggcagtggtg gggtgtatc ttctgtgccg actaacctgg aagttgtcgc ggccactcct   1020
acaagtctgc tgattagctg ggatgcctat cgtgaactgc cggtttctta ttaccgcatc  1080
acgtacggtg agacaggcgg taatagtcct gttcaagagt ttactgtacc tggtagcaaa  1140
agcaccgcga ctattagtgg gctgaagccg gagtggatt acaccatcac cgtatatgct   1200
cattataatt atcactacta tagctcaccg atcagcatta actatcgtgg tcctggtcgc  1260
gaatatgtgc gctttgcccc gggaagcacc caccaccatc atcatcac              1308
```

<210> SEQ ID NO 51
<211> LENGTH: 1323
<212> TYPE: DNA

<213> ORGANISM: Artificial Sequence
<220> FEATURE:
<223> OTHER INFORMATION: protease construct

<400> SEQUENCE: 51

```
tctagtggtt ctaaagcttt gctgaagggc gtgcgcgatt ttaatccgat ctctgcttgc      60
gtatgcctgc tggaaaactc ctcggatggt catagtgaac gtctgtttgg cattggtttt     120
ggcccgtata tcattgccaa ccagcatctg tttcgtcgta acaatggcga actgaccatc     180
aaaaccatgc atggtgaatt caaagtcaaa aactctaccc agctgcagat gaaaccggtt     240
gaaggccgtg acattatcgt tatcaaaatg gctaaagact cccgccgtt cccgcagaaa      300
ctgaaattcc gtcagccgac catcaaagat cgtgtgtgca tggtgtccac caactttcag     360
cagaaaagcg tctcgagcct ggtgtctgaa tcctctcaca ttgtgcataa agaagacact     420
tctttctggc agcactggat caccactaaa gatggccagt gtggcagccc actagtttcc     480
atcattgatg gcaacattct gggcatccac agcctgactc ataccaccaa cggtagcaac     540
tacttcgtgg aatttccgga aaaattcgtg gcgacttatc tagatgccgc ggatggttgg     600
tgcaaaaact ggaaattcaa cgcggataaa atcagctggg gttcctttat cctgtgggaa     660
agtggtagtc cggagttagg ttttagtatt tcaggtggtg tcggtggtcg tgggaatcct     720
tttcgtccag atgatgatgg aattttcgtt acgcgtgtcc agccggaggg cccagctagc     780
aagctgctgc aacctgggga taaaatcatt caagctaacg ttatagctt tatcaacatt      840
gaacatggcc aagctgtcag cttactgaaa acctttcaga acacagtcga actgattatc     900
gttcgcgagg tgggtaatgg tgccaagcag gaaatccgcg ttcgcgtgga aaggatggc      960
ggcagtggtg ggggtgggtc tgggggttct gtatcttctg tgccgactaa cctggaagtt    1020
gtcgcggcca ctcctacaag tctgctgatt agctgggatg cctatcgtga actgccggtt    1080
tcttattacc gcatcacgta cggtgagaca ggcggtaata gtcctgttca agagtttact    1140
gtacctggta gcaaaagcac cgcgactatt agtgggctga agcccgggagt ggattacacc    1200
atcaccgtat atgctcatta taattatcac tactatagct caccgatcag cattaactat    1260
cgtggtcctg gtcgcgaata tgtgcgcttt gccccgggaa gcaccccacca ccatcatcat   1320
cac                                                                 1323
```

<210> SEQ ID NO 52
<211> LENGTH: 1326
<212> TYPE: DNA
<213> ORGANISM: Artificial Sequence
<220> FEATURE:
<223> OTHER INFORMATION: protease construct

<400> SEQUENCE: 52

```
tctagtggtt ctaaagcttt gctgaagggc gtgcgcgatt ttaatccgat ctctgcttgc      60
gtatgcctgc tggaaaactc ctcggatggt catagtgaac gtctgtttgg cattggtttt     120
ggcccgtata tcattgccaa ccagcatctg tttcgtcgta acaatggcga actgaccatc     180
aaaaccatgc atggtgaatt caaagtcaaa aactctaccc agctgcagat gaaaccggtt     240
gaaggccgtg acattatcgt tatcaaaatg gctaaagact cccgccgtt cccgcagaaa      300
ctgaaattcc gtcagccgac catcaaagat cgtgtgtgca tggtgtccac caactttcag     360
cagaaaagcg tctcgagcct ggtgtctgaa tcctctcaca ttgtgcataa agaagacact     420
tctttctggc agcactggat caccactaaa gatggccagt gtggcagccc actagtttcc     480
atcattgatg gcaacattct gggcatccac agcctgactc ataccaccaa cggtagcaac     540
```

```
tacttcgtgg aatttccgga aaaattcgtg gcgacttatc tagatgccgc ggatggttgg      600
tgcaaaaact ggaaattcaa cgcggataaa atcagctggg gttcctttat cctgtgggaa      660
ggtagtggta gtccggagtt aggttttagt atttcaggtg gtgtcggtgg tcgtgggaat      720
ccttttcgtc cagatgatga tggaattttc gttacgcgtg tccagccgga gggcccagct      780
agcaagctgc tgcaacctgg ggataaaatc attcaagcta acggttatag ctttatcaac      840
attgaacatg gccaagctgt cagcttactg aaaaccttte agaacacagt cgaactgatt      900
atcgttcgcg aggtgggtaa tggtgccaag caggaaatcc gcgttcgcgt ggagaaggat      960
ggcggcagtg gtgggggtgg gtctgggggt tctgtatctt ctgtgccgac taacctggaa     1020
gttgtcgcgg ccactcctac aagtctgctg attagctggg atgcctatcg tgaactgccg     1080
gtttcttatt accgcatcac gtacggtgag acaggcggta atagtcctgt tcaagagttt     1140
actgtacctg gtagcaaaag caccgcgact attagtgggc tgaagccggg agtggattac     1200
accatcaccg tatatgctca ttataattat cactactata gctcaccgat cagcattaac     1260
tatcgtggtc ctggtcgcga atatgtgcgc tttgccccgg gaagcaccca ccaccatcat     1320
catcac                                                                1326

<210> SEQ ID NO 53
<211> LENGTH: 1329
<212> TYPE: DNA
<213> ORGANISM: Artificial Sequence
<220> FEATURE:
<223> OTHER INFORMATION: protease construct

<400> SEQUENCE: 53
tctagtggtt ctaaagcttt gctgaagggc gtgcgcgatt ttaatccgat ctctgcttgc       60
gtatgcctgc tggaaaactc ctcggatggt catagtgaac gtctgtttgg cattggtttt      120
ggcccgtata tcattgccaa ccagcatctg tttcgtcgta caatggcga actgaccatc       180 aaaaccatgc atggtgaatt caaagtcaaa aactctaccc agctgcagat gaaaccggtt      240
gaaggccgtg acattatcgt tatcaaaatg gctaaagact cccgccgtt cccgcagaaa       300 ctgaaattcc gtcagccgac catcaaagat cgtgtgtgca tggtgtccac caactttcag      360
cagaaaagcg tctcgagcct ggtgtctgaa tcctctcaca ttgtgcataa agaagacact      420
tctttctggc agcactggat caccactaaa gatggccagt gtggcagccc actagttccc     480
atcattgatg caacattct gggcatccac agcctgactc ataccaccaa cggtagcaac       540
tacttcgtgg aatttccgga aaaattcgtg gcgacttatc tagatgccgc ggatggttgg      600
tgcaaaaact ggaaattcaa cgcggataaa atcagctggg gttcctttat cctgtgggaa      660
ggtggtagtg gtagtccgga gttaggtttt agtatttcag gtggtgtcgg tggtcgtggg      720
aatccttttc gtccagatga tgatggaatt ttcgttacgc gtgtccagcc ggagggccca      780
gctagcaagc tgctgcaacc tggggataaa atcattcaag ctaacggtta tagctttatc      840
aacattgaac atggccaagc tgtcagctta ctgaaaacct tcagaacac agtcgaactg       900 attatcgttc gcgaggtggg taatggtgcc aagcaggaaa tccgcgttcg cgtggagaag      960
gatggcggca gtggtggggg tgggtctggg ggttctgtat cttctgtgcc gactaacctg     1020
gaagttgtcg cggccactcc tacaagtctg ctgattagct gggatgccta tcgtgaactg     1080
ccggtttctt attaccgcat cacgtacggt gagacaggcg gtaatagtcc tgttcaagag     1140
tttactgtac ctggtagcaa aagcaccgcg actattagtg ggctgaagcc gggagtggat     1200
```

| | |
|---|---|
| tacaccatca ccgtatatgc tcattataat tatcactact atagctcacc gatcagcatt | 1260 |
| aactatcgtg gtcctggtcg cgaatatgtg cgctttgccc cgggaagcac ccaccaccat | 1320 |
| catcatcac | 1329 |

<210> SEQ ID NO 54
<211> LENGTH: 1332
<212> TYPE: DNA
<213> ORGANISM: Artificial Sequence
<220> FEATURE:
<223> OTHER INFORMATION: protease construct

<400> SEQUENCE: 54

| | |
|---|---|
| tctagtggtt ctaaagcttt gctgaagggc gtgcgcgatt ttaatccgat ctctgcttgc | 60 |
| gtatgcctgc tggaaaactc ctcggatggt catagtgaac gtctgtttgg cattggtttt | 120 |
| ggcccgtata tcattgccaa ccagcatctg tttcgtcgta caatggcga actgaccatc | 180 |
| aaaaccatgc atggtgaatt caaagtcaaa aactctaccc agctgcagat gaaaccggtt | 240 |
| gaaggccgtg acattatcgt tatcaaaatg gctaaagact tcccgccgtt cccgcagaaa | 300 |
| ctgaaattcc gtcagccgac catcaaagat cgtgtgtgca tggtgtccac caactttcag | 360 |
| cagaaaagcg tctcgagcct ggtgtctgaa tcctctcaca ttgtgcataa agaagacact | 420 |
| tctttctggc agcactggat caccactaaa gatggccagt gtggcagccc actagtttcc | 480 |
| atcattgatg caacattct gggcatccac agcctgactc ataccaccaa cggtagcaac | 540 |
| tacttcgtgg aatttccgga aaaattcgtg gcgacttatc tagatgccgc ggatggttgg | 600 |
| tgcaaaaact ggaaattcaa cgcggataaa atcagctggg gttcctttat cctgtgggaa | 660 |
| ggtggtggta gtggtagtcc ggagttaggt tttagtattt caggtggtgt cggtggtcgt | 720 |
| gggaatcctt ttcgtccaga tgatgatgga attttcgtta cgcgtgtcca gccggagggc | 780 |
| ccagctagca agctgctgca acctggggat aaaatcattc aagctaacgg ttatagcttt | 840 |
| atcaacattg aacatggcca agctgtcagc ttactgaaaa cctttcagaa cacagtcgaa | 900 |
| ctgattatcg ttcgcgaggt gggtaatggt gccaagcagg aaatccgcgt tcgcgtggag | 960 |
| aaggatggcg gcagtggtgg gggtgggtct gggggttctg tatcttctgt gccgactaac | 1020 |
| ctggaagttg tcgcggccac tcctacaagt ctgctgatta gctgggatgc ctatcgtgaa | 1080 |
| ctgccggttt cttattaccg catcacgtac ggtgagacag gcggtaatag tcctgttcaa | 1140 |
| gagtttactg tacctggtag caaaagcacc gcgactatta gtgggctgaa gccgggagtg | 1200 |
| gattaccacca tcaccgtata tgctcattat aattatcact actatagctc accgatcagc | 1260 |
| attaactatc gtggtcctgg tcgcgaatat gtgcgctttg ccccgggaag cacccaccac | 1320 |
| catcatcatc ac | 1332 |

<210> SEQ ID NO 55
<211> LENGTH: 1335
<212> TYPE: DNA
<213> ORGANISM: Artificial Sequence
<220> FEATURE:
<223> OTHER INFORMATION: protease construct

<400> SEQUENCE: 55

| | |
|---|---|
| tctagtggtt ctaaagcttt gctgaagggc gtgcgcgatt ttaatccgat ctctgcttgc | 60 |
| gtatgcctgc tggaaaactc ctcggatggt catagtgaac gtctgtttgg cattggtttt | 120 |
| ggcccgtata tcattgccaa ccagcatctg tttcgtcgta caatggcga actgaccatc | 180 |
| aaaaccatgc atggtgaatt caaagtcaaa aactctaccc agctgcagat gaaaccggtt | 240 |

```
gaaggccgtg acattatcgt tatcaaaatg gctaaagact tcccgccgtt cccgcagaaa    300
ctgaaattcc gtcagccgac catcaaagat cgtgtgtgca tggtgtccac caactttcag    360
cagaaaagcg tctcgagcct ggtgtctgaa tcctctcaca ttgtgcataa agaagacact    420
tctttctggc agcactggat caccactaaa gatggccagt gtggcagccc actagtttcc    480
atcattgatg gcaacattct gggcatccac agcctgactc ataccaccaa cggtagcaac    540
tacttcgtgg aatttccgga aaaattcgtg gcgacttatc tagatgccgc ggatggttgg    600
tgcaaaaact ggaaattcaa cgcggataaa atcagctggg gttcctttat cctgtgggaa    660
ggtggtagtg gtagtggtag tccggagtta ggttttagta tttcaggtgg tgtcggtggt    720
cgtgggaatc cttttcgtcc agatgatgat ggaattttcg ttacgcgtgt ccagccggag    780
ggcccagcta gcaagctgct gcaacctggg gataaaatca ttcaagctaa cggttatagc    840
tttatcaaca ttgaacatgg ccaagctgtc agcttactga aaacctttca gaacacagtc    900
gaactgatta tcgttcgcga ggtgggtaat ggtgccaagc aggaaatccg cgttcgcgtg    960
gagaaggatg gcggcagtgg tgggggtggg tctgggggtt ctgtatcttc tgtgccgact   1020
aacctggaag ttgtcgcggc cactcctaca agtctgctga ttagctggga tgcctatcgt   1080
gaactgccgg tttcttatta ccgcatcacg tacggtgaga caggcggtaa tagtcctgtt   1140
caagagttta ctgtacctgg tagcaaaagc accgcgacta ttagtgggct gaagccggga   1200
gtggattaca ccatcaccgt atatgctcat tataattatc actactatag ctcaccgatc   1260
agcattaact atcgtggtcc tggtcgcgaa tatgtgcgct ttgccccggg aagcacccac   1320
caccatcatc atcac                                                   1335

<210> SEQ ID NO 56
<211> LENGTH: 1584
<212> TYPE: DNA
<213> ORGANISM: Artificial Sequence
<220> FEATURE:
<223> OTHER INFORMATION: protease construct

<400> SEQUENCE: 56
tctggtggtt ctggggcaga gtatgtgcgg gccctctttg actttaatgg gaatgatgaa     60
gaagatcttc catttaagaa aggagacatc ctgcgtatcc gggataagcc tgaagagcag    120
tggtggaatg cagaggacag cgaaggaaag cgtgggatga ttcctgtccc ttacgtggag    180
aagtatcgcc ctgcctccgc ctcagtatcg gctctgattg aggtcggggc ggtagcggt    240 ggtagcggcg gtagcggcgg tagcggtggc tcgggcggtt cgtctaaagc tttgctgaag    300
ggcgtgcgcg atttaatcc gatctctgct tgcgtatgcc tgctggaaaa ctcctcggat    360
ggtcatagtg aacgtctgtt tggcattggt tttggcccgt atatcattgc caaccagcat    420
ctgtttcgtc gtaacaatgg cgaactgacc atcaaaacca tgcatggtga attcaaagtc    480
aaaaactcta cccagctgca gatgaaaccg gttgaaggcc gtgacattat cgttatcaaa    540
atggctaaag acttcccgcc gttcccgcag aaactgaaat ccgtcagcc gaccatcaaa    600 gatcgtgtgt gcatggtgtc caccaacttt cagcagaaaa gcgtctcgag cctggtgtct    660
gaatcctctc acattgtgca taagaagac acttctttct ggcagcactg gatcaccact    720
aaagatggcc agtgtggcag cccactagtt tccatcattg atggcaacat tctgggcatc    780
cacagcctga ctcataccac caacggtagc aactacttcg tggaatttcc ggaaaaattc    840
gtggcgactt atctagatgc cgcggatggt tggtgcaaaa actggaaatt caacgcggat    900
```

-continued

```
aaaatcagct ggggttccttt tatcctgtgg gaaagtggta gtccggagtt aggttttagt    960
atttcaggtg gtgtcggtgg tcgtgggaat ccttttcgtc cagatgatga tggaattttc   1020
gttacgcgtg tccagccgga gggcccagct agcaagctgc tgcaacctgg ggataaaatc   1080
attcaagcta acggttatag ctttatcaac attgaacatg gccaagctgt cagcttactg   1140
aaaacctttc agaacacagt cgaactgatt atcgttcgcg aggtgggtaa tggtgccaag   1200
caggaaatcc gcgttcgcgt ggagaaggat ggcggcagtg gtgggggtgg ggtatcttct   1260
gtgccgacta acctggaagt tgtcgcggcc actcctacaa gtctgctgat tagctgggat   1320
gcctatcgtg aactgccggt ttcttattac cgcatcacgt acggtgagac aggcggtaat   1380
agtcctgttc aagagtttac tgtacctggt agcaaaagca ccgcgactat tagtgggctg   1440
aagccgggag tggattacac catcaccgta tatgctcatt ataattatca ctactatagc   1500
tcaccgatca gcattaacta tcgtggtcct ggtcgcgaat atgtgcgctt tgccccggga   1560
agcacccacc accatcatca tcac                                          1584
```

```
<210> SEQ ID NO 57
<211> LENGTH: 10
<212> TYPE: PRT
<213> ORGANISM: Artificial Sequence
<220> FEATURE:
<223> OTHER INFORMATION: peptide

<400> SEQUENCE: 57

Arg Glu Thr Val Arg Phe Gln Ser Asp Thr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: peptide

<400> SEQUENCE: 58

Asp Glu Leu Ile Leu Cys Pro Leu Asp Leu
1               5                   10

<210> SEQ ID NO 59
<211> LENGTH: 9
<212> TYPE: PRT
<213> ORGANISM: Artificial Sequence
<220> FEATURE:
<223> OTHER INFORMATION: peptide

<400> SEQUENCE: 59

Glu Asn Leu Tyr Phe Gln Ser Asp Thr
1               5

<210> SEQ ID NO 60
<211> LENGTH: 9
<212> TYPE: PRT
<213> ORGANISM: Artificial Sequence
<220> FEATURE:
<223> OTHER INFORMATION: peptide

<400> SEQUENCE: 60

Glu Asn Leu Tyr Phe Gln Ser Asp Thr
1               5

<210> SEQ ID NO 61
<211> LENGTH: 10
```

```
<212> TYPE: PRT
<213> ORGANISM: Artificial Sequence
<220> FEATURE:
<223> OTHER INFORMATION: peptide

<400> SEQUENCE: 61

Gly Glu Thr Val Arg Phe Gln Ser Asp Thr
1               5                   10

<210> SEQ ID NO 62
<211> LENGTH: 10
<212> TYPE: PRT
<213> ORGANISM: Artificial Sequence
<220> FEATURE:
<223> OTHER INFORMATION: peptide

<400> SEQUENCE: 62

Gly Glu Thr Val Arg Phe Gln Ser Asp Thr
1               5                   10

<210> SEQ ID NO 63
<211> LENGTH: 10
<212> TYPE: PRT
<213> ORGANISM: Artificial Sequence
<220> FEATURE:
<223> OTHER INFORMATION: peptide

<400> SEQUENCE: 63

Gly Glu Asp Val Phe His Gln Ser Gly Ser
1               5                   10

<210> SEQ ID NO 64
<211> LENGTH: 10
<212> TYPE: PRT
<213> ORGANISM: Artificial Sequence
<220> FEATURE:
<223> OTHER INFORMATION: peptide

<400> SEQUENCE: 64

Gly Glu Asp Val Phe His Gln Ser Gly Ser
1               5                   10

<210> SEQ ID NO 65
<211> LENGTH: 9
<212> TYPE: PRT
<213> ORGANISM: Artificial Sequence
<220> FEATURE:
<223> OTHER INFORMATION: peptide

<400> SEQUENCE: 65

Asp Asp Val Thr Pro Cys Ser Met Ser
1               5

<210> SEQ ID NO 66
<211> LENGTH: 8
<212> TYPE: PRT
<213> ORGANISM: Artificial Sequence
<220> FEATURE:
<223> OTHER INFORMATION: peptide

<400> SEQUENCE: 66

Arg Gly Ser Ile Asp Thr Trp Val
1               5

<210> SEQ ID NO 67
<211> LENGTH: 8
<212> TYPE: PRT
```

```
<213> ORGANISM: Artificial Sequence
<220> FEATURE:
<223> OTHER INFORMATION: peptide

<400> SEQUENCE: 67

Pro Gln Pro Val Asp Ser Trp Val
1               5

<210> SEQ ID NO 68
<211> LENGTH: 10
<212> TYPE: PRT
<213> ORGANISM: Artificial Sequence
<220> FEATURE:
<223> OTHER INFORMATION: peptide

<400> SEQUENCE: 68

Arg Glu Thr Val Arg Phe Gln Ser Asp Thr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: peptide

<400> SEQUENCE: 69

Thr Glu Asn Leu Tyr Phe Gln Ser Gly Thr
1               5                   10

<210> SEQ ID NO 70
<211> LENGTH: 10
<212> TYPE: PRT
<213> ORGANISM: Artificial Sequence
<220> FEATURE:
<223> OTHER INFORMATION: peptide

<400> SEQUENCE: 70

Asn Glu Asp Val Phe His Gln Ser Gly Ser
1               5                   10

<210> SEQ ID NO 71
<211> LENGTH: 10
<212> TYPE: PRT
<213> ORGANISM: Artificial Sequence
<220> FEATURE:
<223> OTHER INFORMATION: peptide

<400> SEQUENCE: 71

Arg Glu Thr Val Arg Phe Gln Ser Asp Thr
1               5                   10

<210> SEQ ID NO 72
<211> LENGTH: 10
<212> TYPE: PRT
<213> ORGANISM: Artificial Sequence
<220> FEATURE:
<223> OTHER INFORMATION: peptide

<400> SEQUENCE: 72

Arg Glu Thr Val Arg Phe Ala Pro Gly Ser
1               5                   10

<210> SEQ ID NO 73
<211> LENGTH: 10
<212> TYPE: PRT
<213> ORGANISM: Artificial Sequence
```

```
<220> FEATURE:
<223> OTHER INFORMATION: peptide

<400> SEQUENCE: 73

Arg Glu Thr Val Arg Phe Gly Pro Gly Ser
1               5                   10

<210> SEQ ID NO 74
<211> LENGTH: 10
<212> TYPE: PRT
<213> ORGANISM: Artificial Sequence
<220> FEATURE:
<223> OTHER INFORMATION: peptide

<400> SEQUENCE: 74

Arg Glu Thr Val Arg Phe Pro Pro Gly Ser
1               5                   10

<210> SEQ ID NO 75
<211> LENGTH: 10
<212> TYPE: PRT
<213> ORGANISM: Artificial Sequence
<220> FEATURE:
<223> OTHER INFORMATION: peptide

<400> SEQUENCE: 75

Arg Glu Thr Val Arg Phe Gln Pro Gly Ser
1               5                   10

<210> SEQ ID NO 76
<211> LENGTH: 16
<212> TYPE: PRT
<213> ORGANISM: Artificial Sequence
<220> FEATURE:
<223> OTHER INFORMATION: peptide

<400> SEQUENCE: 76

Trp Gly Ser Phe Thr Leu Val Glu Asp Ala Pro Glu Asp Asp Phe Met
1               5                   10                  15

<210> SEQ ID NO 77
<211> LENGTH: 8
<212> TYPE: PRT
<213> ORGANISM: Artificial Sequence
<220> FEATURE:
<223> OTHER INFORMATION: peptide

<400> SEQUENCE: 77

Ser Gly Leu Val Pro Arg Gly Val
1               5

<210> SEQ ID NO 78
<211> LENGTH: 18
<212> TYPE: PRT
<213> ORGANISM: Artificial Sequence
<220> FEATURE:
<223> OTHER INFORMATION: peptide

<400> SEQUENCE: 78

Gly Arg Glu Thr Val Arg Phe Ala Pro Gly Ser Thr His His His His
1               5                   10                  15

His His

<210> SEQ ID NO 79
<211> LENGTH: 11
<212> TYPE: PRT
```

```
<213> ORGANISM: Artificial Sequence
<220> FEATURE:
<223> OTHER INFORMATION: peptide

<400> SEQUENCE: 79

Trp Gly Ser Phe Thr Leu Val Glu Asp Ala Pro
1               5                   10

<210> SEQ ID NO 80
<211> LENGTH: 10
<212> TYPE: PRT
<213> ORGANISM: Artificial Sequence
<220> FEATURE:
<223> OTHER INFORMATION: peptide

<400> SEQUENCE: 80

Ser Gly Leu Val Pro Arg Gly Val Ser Gly
1               5                   10

<210> SEQ ID NO 81
<211> LENGTH: 18
<212> TYPE: PRT
<213> ORGANISM: Artificial Sequence
<220> FEATURE:
<223> OTHER INFORMATION: peptide

<400> SEQUENCE: 81

Glu Gly Glu Thr Val Arg Phe Gly Pro Gly Ser Thr His His His His
1               5                   10                  15

His His

<210> SEQ ID NO 82
<211> LENGTH: 18
<212> TYPE: PRT
<213> ORGANISM: Artificial Sequence
<220> FEATURE:
<223> OTHER INFORMATION: peptide

<400> SEQUENCE: 82

Glu Gly Glu Thr Val Arg Phe Ala Pro Gly Ser Thr His His His His
1               5                   10                  15

His His

<210> SEQ ID NO 83
<211> LENGTH: 9
<212> TYPE: PRT
<213> ORGANISM: Artificial Sequence
<220> FEATURE:
<223> OTHER INFORMATION: peptide

<400> SEQUENCE: 83

Trp Gly Ser Phe Ile Leu Trp Glu Asp
1               5

<210> SEQ ID NO 84
<211> LENGTH: 18
<212> TYPE: PRT
<213> ORGANISM: Artificial Sequence
<220> FEATURE:
<223> OTHER INFORMATION: peptide
```

<400> SEQUENCE: 84

Glu Gly Glu Tyr Val Arg Phe Gly Pro Gly Ser Thr His His His His
1               5                   10                  15

His His

PROTEASE-BASED BIOSENSOR

This application is the U.S. national phase of International Application No. PCT/AU2013/001039, filed 12 Sep. 2013, which designated the U.S. and claims priority to Australian Application No. 2012903979, filed 12 Sep. 2012; the entire contents of each of which are hereby incorporated by reference.

TECHNICAL FIELD

THIS INVENTION relates to biosensors. More particularly, this invention relates to a biosensor molecule comprising protease activity that is suitable for detection of one or more target molecules in a sample. The biosensor molecule may also relate to the field of synthetic biology such as for constructing artificial cellular signalling networks.

BACKGROUND

Detection of target molecules or analytes in biological samples is central to diagnostic monitoring of health and disease. Key requirements of analyte detection are specificity and sensitivity, particularly when the target molecule or analyte is in a limiting amount or concentration in a biological sample.

Typically, specificity is provided by monoclonal antibodies which specifically bind the analyte. Sensitivity is typically provided by a label bound to the specific antibody, or to a secondary antibody which assists detection of relatively low levels of analyte. This type of diagnostic approach has become well known and widely used in the enzyme-linked immunosorbent sandwich assay (ELISA) format. In some cases, enzyme amplification can even further improve sensitivity such as by using a product of a proenzyme cleavage reaction catalyzing the same reaction. Some examples of such "autocatalytic" enzymes are trypsinogen, pepsinogen, or the blood coagulation factor XII. However, in relation to specificity antibodies are relatively expensive and can be difficult to produce with sufficient specificity for some analytes. Polyclonal antibodies also suffer from the same shortcomings and are even more difficult to produce and purify on a large scale.

Current methods to detect specific target molecules and analytes for either prognostic or diagnostic purposes suffer from a number of limitations which significantly restrict their widespread application in clinical, peri-operative and point-of-care settings. Most importantly, the vast majority of diagnostic assays require a significant level of technical expertise and a panel of expensive and specific reagents (most notably monoclonal antibodies) along with elaborate biomedical infrastructures which are rarely available outside specialized laboratory environments. For instance, ELISAs—the gold standard for detecting specific analytes in complex biological samples—rely on the selective capture of a target analyte on a solid surface which in turn is detected with a second affinity reagent that is specific for the target analyte. ELISAs also feature extensive incubation and washing steps which are generally time consuming and difficult to standardize as the number of successive steps frequently introduces significant variation across different procedures, operators and laboratories making quantitative comparisons difficult. In addition, it is often desirable to measure the active state of a target analyte, and not just detect its presence as is frequently only possible with ELISAs. This particularly applies to proteases whose activity is tightly regulated as they carry out critical functions in a range of important physiological processes, and are frequently de-regulated in different disease states including cancer (e.g. matrix metalloproteinases), infectious disease (e.g. pathogen specific proteases) and cardiac disorders (e.g. components of the blood coagulation cascade).

For instance, blood coagulation assays feature some of the most widely established protease assay platforms which are routinely applied in clinical laboratories to diagnose aberrant coagulation processes caused by drugs or underlying pathological processes. The majority of conventional blood screening tests that are used to characterise haemostatic phenotypes (including indirect assay methods used to quantify individual components of the blood coagulation cascade) generally measure the time to form a fibrin clot and almost exclusively relay their effect through multiple components of the blood coagulation cascade, in particular thrombin and the common pathway: e.g. prothrombin time, activated partial thromboplastin time, thrombin and reptilase time and various fibrinogen assays. These assays usually take advantage of the natural amplification power of the blood clotting system; this is however associated with a number of disadvantages: For example, the dependence on multiple clotting factors for a particular read-out limits their precision as variations in the genetic background of an individual generally make it hard to deconvolute the contribution of one particular component of the blood coagulation cascade to a given haemostatic phenotype observed in the clinic. Similarly, regulatory mechanisms in protease signalling networks and physiological variations in the components of the coagulation cascade (e.g. in the presence or absence of drugs etc.) make it difficult to translate assay data into targeted treatment regimes in the clinic as there is no clear-cut correlation between cause and effect at the molecular level.

Beyond blood coagulation, proteases are also increasingly recognized to carry out critical functions in a number of disease processes; these are expected to open new avenues for diagnostic and therapeutic regimes. Since most proteases are of relatively low abundance and do not readily form part of extended protease signalling networks with intrinsic amplification power (compared with blood coagulation system), the establishment of highly sensitive, specific and easily operable protease assays has remained a challenge to date. Two widely applied protease assays are based on zymography and FRET-based fluorescent assays based on short peptide substrates: Compared to ELISAs, zymography carries the advantage that only active proteases are assayed while inactive zymogens are not. However, zymographic techniques are generally laborious taking up to two days to develop (Kupai, et al., 2010, J Pharmacol Toxicol Methods, 61, 205-9.) and are thus not readily integratable into point-of-care devices. In addition, problems persist with standardisation, sensitivity and data interpretation. More recently, FRET-based fluorescent assays based on highly specific peptide substrates have been developed. Substrate peptides can either be derived from natural substrates or can be artificially engineered for greater specificity. Nevertheless, limited sensitivities remain especially if the target protease is present in limiting amounts: e.g. the best substrates for matrix metalloproteinases developed to date take about two hours to develop in cell culture and tolerate only limited amounts of plasma (Jabaiah & Daugherty, 2011, Chem Biol 18, 392-401) while screens do not readily select against promiscuous substrate specificities. From a biophysical point of view, the lack of specificity and selectivity of peptide based substrates can largely be attributed to the limited surface area which any given peptide can provide towards molecular recognition as well as the lack of biomolecular signal amplification which is a trademark of biological signalling systems.

SUMMARY

The present invention addresses a need to develop quantitative, relatively inexpensive and easily distributable molecular biosensors that readily detect the presence or the activity of target molecules (e.g analytes) on short time scales that are compatible with treatment regimes. Such biosensors can either be applied singly or in multiplex to validate and/or diagnose molecular phenotypes with high specificity and great statistical confidence irrespective of the genetic background and natural variations in unrelated physiological processes.

It is therefore an object of the invention to provide a biosensor molecule which has specificity for a target molecule and preferably which can produce an amplifiable response to detection of the target molecule.

In one broad form the invention relates to a biosensor molecule comprising a protease amino acid sequence which is switchable from a protease inactive to a protease active state, or from a protease active state to a protease inactive state, in response to a target molecule.

In a preferred broad form, the invention relates to a biosensor molecule comprising a viral protease amino acid sequence which is switchable from a protease inactive to a protease active state in response to a target molecule.

Suitably, in a protease active state the biosensor is capable of eliciting an amplifiable signal.

In a first aspect, the invention provides a biosensor molecule comprising at least one protease amino acid sequence; at least one sensor that comprises at least one sensor amino acid sequence, which at least one sensor is responsive to a target molecule; and an inhibitor of the protease activity of said protease(s); wherein the biosensor, is switchable between a protease active and a protease inactive state, or from a protease inactive to a protease active state when said at least one sensor responds to said target molecule.

In one embodiment, the protease is an endopeptidase. Preferably, the endopeptidase is a cysteine protease or a serine protease.

In another embodiment, the protease is derivable or obtainable from a virus.

In certain embodiments the virus is a Potyvirus such as, tobacco vein mottling virus (TVMV), tobacco etch virus (TEV) or sugarcane mosaic virus (SMV) or a Flavivirus such as Hepatitis C Virus (HCV).

Preferably, the protease is an NIa protease.

In some embodiments, the inhibitor is a peptide. A preferred inhibitor peptide is an autoinhibitory peptide.

In particular embodiments, the autoinhibitor peptide is an autoinhibitor of an NIa protease of a Potyvirus or the NS3 protease of HCV.

In one broad form, the biosensor comprises a single, contiguous amino acid sequence. In another broad form, the biosensor comprises separate protease and sensor amino acid sequences that associate to form the biosensor molecule. The single or separate amino acid sequences may respectively comprise one or more linkers that facilitate stabilization of the single amino acid sequence and/or association of the separate amino acid sequences.

In one general embodiment, the at least one sensor amino acid sequence comprises at least one protease cleavage site cleavable by at least one protease target molecule. Suitably, cleavage by the at least one protease target molecule releases the protease-inhibitory effect of the inhibitor to thereby switch the biosensor from a protease inactive to a protease active state.

In another general embodiment, the sensor further comprises an amino acid sequence can possess or adopt a conformation in which it facilitates protease inhibition by the inhibitor and can possess another conformation which releases the protease-inhibitory effect of the inhibitor. In one particular form of this embodiment, the sensor further comprises an amino acid sequence of an affinity clamp that can possess or adopt a conformation in which it facilitates protease inhibition by the inhibitor and can possess another conformation which releases the protease-inhibitory effect of the inhibitor.

In one embodiment, the sensor further comprises a binding partner. Suitably, the binding partner is a protein. Preferably, the binding partner is an antibody or antibody fragment.

In certain embodiments, the biosensor may comprise first and second sensors responsive to the same or different target molecules. In one form of this embodiment, the biosensor is a circularly permutated biosensor.

In one further embodiment, the biosensor may be capable of being linked or coupled to an amplifier molecule. For example, the biosensor and amplifier molecule may comprise respective interacting domains (i.e an amplifier interacting domain and a biosensor interacting domain) that facilitate releasable linking or coupling of the biosensor and amplifier molecules.

Accordingly, a related aspect of the invention provides an amplifier molecule operable with the biosensor molecule that comprises: (i) an amino acid sequence of a protease that is different to the protease(s) of the biosensor; (ii) an inhibitor of the protease of (i); and (iii) a linker amino acid sequence which comprises a cleavage site for the protease(s) of the biosensor.

Particular embodiments of the biosensor comprise amino acid sequences set forth in SEQ ID NOS:1-28.

Another aspect of the invention provides a composition or kit comprising the biosensor of the aforementioned aspect and a substrate.

In one embodiment, the substrate comprises an amino acid sequence cleavable by the biosensor protease of the biosensor.

In another embodiment, the composition or kit further comprises an amplifier molecule.

Suitably, the amplifier molecule is capable of amplifying a signal elicited by the biosensor in a protease active state.

Suitably, the amplifier molecule comprises: (i) an amino acid sequence of a protease that is different to the protease(s) of the biosensor; (ii) an inhibitor of the protease of (i); and (iii) a linker amino acid sequence which comprises a cleavage site for the protease(s) of the biosensor.

In one particular embodiment, the biosensor may be linked or coupled to the amplifier molecule. For example, the biosensor and amplifier molecule may comprise respective interacting domains (i.e an amplifier interacting domain and a biosensor interacting domain) that facilitate releasable linking or coupling of the biosensor and amplifier molecules.

Preferably, the composition or kit further comprises a deactivating molecule.

Suitably, the deactivating molecule comprises: (i) an amino acid sequence of a protease that is different to the protease of the biosensor and that is different to the protease of the amplification molecule; (ii) an inhibitor of the protease of (i); and (iii) a linker amino acid sequence which comprises a cleavage site for the protease of the amplification molecule.

Suitably, according to this embodiment, the substrate comprises an amino acid sequence cleavable by the protease of the amplification molecule.

The protease and the protease inhibitor may be any of the proteases and inhibitors disclosed herein in relation to the biosensor protease.

The composition or may kit comprise one or a plurality of different biosensors disclosed herein capable of detecting one or a plurality of different target molecules.

In some embodiments, the composition may be in form of a single, mixed reagent that comprises one or more of the biosensor, the amplifier molecule, the deactivating molecule and the substrate.

In some embodiments, the kit may separately provide or more of the biosensor, the amplifier molecule, the deactivating molecule and the substrate as individual components.

Yet another aspect of the invention provides a method of detecting a target molecule, said method including the step of contacting the composition of the aforementioned aspect with a sample to thereby determine the presence or absence of the target molecule in the sample.

Still yet another aspect of the invention provides a method of diagnosis of a disease or condition in a human, said method including the step of contacting the composition of the aforementioned aspect with a biological sample obtained from the human to thereby determine the presence or absence of a target molecule in the biological sample, determination of the presence or absence of the target molecule facilitating diagnosis of the disease or condition.

A further aspect of the invention provides a detection device that comprises a cell or chamber that comprises the biosensor of the first aspect.

Suitably, a sample may be introduced into the cell or chamber to thereby facilitate detection of a target molecule.

In certain embodiments, the detection device is capable of providing an electrochemical, acoustic and/or optical signal that indicates the presence of the target molecule.

A yet further aspect of the invention provides a device for providing a disease diagnosis from a diagnostic target result obtained according to the aforementioned method, the device comprising:
 a processor; and
 a memory coupled to the processor, the memory including computer readable program code components that, when executed by the processor, perform a set of functions including:
 analysing the diagnostic target result and providing a diagnosis of the disease or condition.

A still further aspect of the invention provides a device for communicating a diagnostic target result obtained according to the aforementioned method, the device comprising:
 a processor; and
 a memory coupled to the processor, the memory including computer readable program code components that, when executed by the processor, perform a set of functions including:
 transmitting a diagnostic target result to a receiving device; and
 optionally receiving a diagnosis of the disease or condition from the or another receiving device.

Another further aspect of the invention provides an isolated nucleic acid encoding the biosensor of the aforementioned aspect.

Yet another further aspect of the invention provides a genetic construct comprising the isolated nucleic acid of the aforementioned aspect.

Also provided is a host cell comprising the genetic construct of the aforementioned aspect.

BRIEF DESCRIPTION OF THE FIGURES

FIG. 7: Summary of HCV-based biosensors. To illustrate the general applicability of the concept beyond cysteine proteases, a TVMV-inducible biosensor based on HCV has been constructed by appending an AI-domain to the C-terminus of HCV which was connected via a TVMV-cleavable linker.

DETAILED DESCRIPTION

Figure 1:
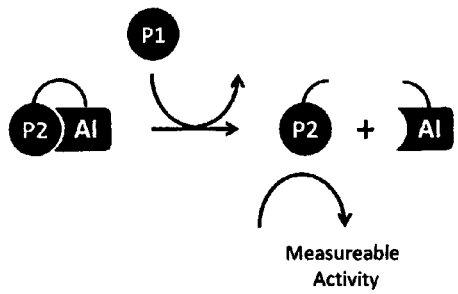
FIG. 1: Schematic representation of: embodiments of the biosensor based on intramolecular inhibition, an extended design based on intermolecular inhibition and positive signal amplification of an allosterically regulated protease biosensor using an amplifier molecule with an orthogonal recognition site relative to the allosterically regulated protease.
Figure 1:
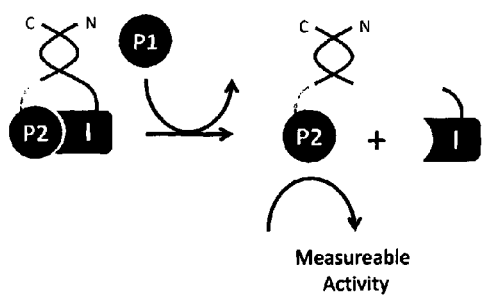
Figure 1:
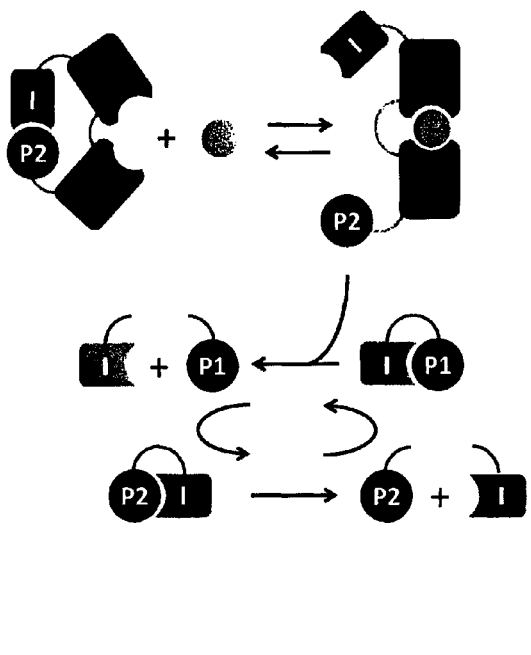

The present invention provides a biosensor molecule which is capable of displaying protease activity in response to a target molecule. Suitably, the biosensor molecule is switchable between protease "inactive" and protease "active" states. The biosensor molecule is initially in an "inactive" state due to the inhibitor suppressing or inhibiting the protease activity of the biosensor molecule. In this initial inactive state, the sensor amino acid sequence connects the protease amino acid sequence and the inhibitor in a manner which allows the inhibitor to bind and thereby suppress or inhibit the protease activity of the biosensor molecule. In embodiments where the target molecule is a protease and the sensor amino acid comprises a cleavage site for the target protease, the presence of the target protease is detected as proteolytic cleavage of the sensor amino acid sequence, which thereby releases the biosensor protease from suppression by the inhibitor, thereby "activating" the protease activity of the biosensor molecule. In embodiments where the target molecule is a molecule other than a protease, the sensor amino acid is capable of binding the target molecule in a manner which alters the conformation of the sensor amino acid sequence which thereby releases the biosensor protease from suppression by the inhibitor, thereby "activating" the protease activity of the biosensor molecule. A preferred form of the sensor amino acid sequence of this embodiment is an affinity clamp, as will be described hereinafter. The "activated" biosensor molecule of either embodiment may proteolytically cleave a labeled substrate to facilitate generation of a detectable signal. In further embodiments, the signal produced by the protease active biosensor molecule may be amplified by way of an amplifier molecule which will be described in more detail hereinafter.

The biosensor molecule disclosed herein may have efficacy in molecular diagnostics wherein the "target molecule" is an analyte or other molecule of diagnostic value or importance. However, another application of the biosensor disclosed herein may be in synthetic biology applications for constructing multi-component artificial cellular signalling networks.

It will be appreciated that the indefinite articles "a" and "an" are not to be read as singular indefinite articles or as otherwise excluding more than one or more than a single subject to which the indefinite article refers. For example, "a" molecule includes one molecule, one or more molecules or a plurality of molecules.

As used herein, unless the context requires otherwise, the words "comprise", "comprises" and "comprising" will be understood to mean the inclusion of a stated integer or group of integers but not the exclusion of any other integer or group of integers.

For the purposes of this invention, by "isolated" is meant material (such as a molecule) that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated proteins and nucleic acids may be in native, chemical synthetic or recombinant form.

By "protein" is meant an amino acid polymer. The amino acids may be natural or non-natural amino acids, D- or L-amino acids as are well understood in the art.

A "peptide" is a protein having less than fifty (50) amino acids.

A "polypeptide" is a protein having fifty (50) or more amino acids.

A "protease" is any protein which displays, or is capable of displaying, an ability to hydrolyse or otherwise cleave a peptide bond. Like terms include "proteinase" and "peptidase". Proteases include serine proteases, cysteine proteases, metalloproteases, threonine proteases, aspartate proteases, glutamic acid proteases, acid proteases, neutral proteases, alkaline proteases, exoproteases, aminopeptidases and endopeptidases although without limitation thereto. Proteases may be purified or synthetic (e.g. recombinant synthetic) forms of naturally-occurring proteases or may be engineered or modified proteases which comprise one or more fragments or domains of naturally-occurring proteases which, optionally, have been further modified to possess one or more desired characteristics, activities or properties.

Proteases are found throughout nature, including viruses, bacteria, yeasts, plants, invertebrate animals and vertebrates inclusive of mammals and humans, although without limitation thereto. Accordingly, proteases are involved in a variety of different physiological processes including digestion of food proteins, blood-clotting cascades, the complement system, apoptosis pathways, the invertebrate prophenoloxidase-activating cascade, bacterial exotoxins and processing of viral proteins, although without limitation thereto.

An aspect of the invention provides a biosensor comprising a protease amino acid sequence; at least one sensor comprising at least one sensor amino acid sequence which is responsive to at least one target molecule; and an inhibitor of the protease activity of said protease amino acid sequence; wherein the biosensor is switchable from a protease active to a protease inactive state, or from a protease inactive to a protease active state when said sensor responds to said target molecule.

The present invention therefore provides a biosensor comprising a protease amino acid sequence, wherein the protease amino acid sequence is capable of displaying protease activity. The protease amino acid sequence may be an entire amino acid sequence of a protease or may be an amino acid sequence of a proteolytically-active fragment or sub-sequence of a protease.

In one preferred embodiment, the protease is an endopeptidase.

Preferably, the endopeptidase is a cysteine protease or serine protease. A particular example of a cysteine protease is NIa protease of Potyviruses. A particular example of a serine protease is an NS3 protease of a Flavivirus such as HCV.

In another preferred embodiment, the protease is a naturally-occurring protease.

A preferred class of proteases are derived from, or encoded by, a viral genome. Typically, such proteases are dependent on expression and proteolytic processing of a polyprotein and/or other events required as part of the life cycle of viruses such as Picornavirales, Nidovirales, Herpesvirales, Retroviruses and Adenoviruses, although without limitation thereto. Particular examples of proteases include: Potyviridae proteases such as the NIa protease of tobacco etch virus (TEV), tobacco vein mottling virus (TVMV), sugarcane mosaic virus (SMV) etc; Flaviviridae proteases such as the NS3 protease of hepatitis C virus (HCV); Picornaviridae proteases such as the 3C protease of EV71, Norovirus etc, the 2A protease of human rhinovirus, coxsackievirus B4 etc and the leader protease of foot and mouth disease virus (FMDV) etc; Coronaviridae proteases such as the 3C-like protease of SARS-CoV, IBV-CoV and Herpesvirus proteases such as HSV-1, HSV-2, HCMV and MCMV proteases etc, although without limitation thereto.

Preferably, the viral genome is of a plant virus.

More preferably, the plant virus is a Potyvirus.

In a particularly preferred embodiment, the protease is an auto-inhibited Potyvirus protease such as the NIa protease of TEV, TVMV or SMV.

The native function of NIa proteases from Potyviridae is to process the viral polyprotein proteome. Auto-inhibition is mediated by peptides that bind the active site of NIa proteases and inhibit their activity. Such inhibitors are typically derived from Site F which separates the NIb RNA polymerase from the viral coat protein, and is considered the most efficient substrate for NIa proteases.

In an alternative embodiment the protease is an autoinhibited NS3 protease of a Flavivirus such as HCV.

It will be appreciated that the biosensor of the invention is capable of displaying protease activity which can be at least partly inhibited by an inhibitor of the protease activity.

Accordingly, in this context, "switchable from a protease inactive to a protease active state" may include an increase in protease activity from a relatively less active, substantially or completely inactive or inhibited state to a more active state. Similarly, "switchable from a protease active to a protease inactive state" may include a decrease in protease activity from a relatively more active to a less active, substantially or completely inactive or inhibited state.

The inhibitor may be any molecule which at least partly, or substantially or completely suppresses or inhibits the protease activity of the amino acid sequence of the protease. The inhibitor may be a non-specific inhibitor by virtue of having inhibitory activity towards a plurality of different proteases or types of protease, or may be a specific inhibitor by virtue of substantially inhibiting only a single protease.

The inhibitor may be a protein (inclusive of peptides) or a non-protein organic molecule such as a small organic molecule, a lipid, a carbohydrate or a nucleic acid, although without limitation thereto.

Non-limiting examples of protease inhibitors that are proteins include viral autoinhibitory peptides, aprotinin, leupeptin, metallocarboxypeptidase A inhibitor, $\alpha2$ macroglobulin, pepstatin and serpins such as alpha 1-antitrypsin, C1-inhibitor, antithrombin, alpha 1-antichymotrypsin, plasminogen activator inhibitor-1 and neuroserpin, although without limitation thereto. Inhibitors can comprise specific antibody or antibody fragments displaying inhibitory activity, protein domains or peptides displaying specific binding to the protease and exerting competitive, steric or allosteric inhibition, DNA, PNA or RNA aptamers capable of binding to the protease and exerting competitive, steric or allosteric inhibition.

Non-limiting examples of protease inhibitors that are organic molecules include phenylmethanesulfonyl fluoride, tosyl lysine chloromethylketone, tosyl phenylalanyl chloromethyl ketone, bestatin and nitrophenol-p-guanidino benzoate, phosphoramidite and protease inhibitors developed as antiviral agents, such as for treatment of HIV or hepatitis C infection. Non-limiting examples of antiviral protease inhibitors include ritonivir, saquinavir, indinavir, nelfinavir, tipranavir, amprenavir and daumavir, although without limitation thereto.

Preferably, the protease inhibitor is an autoinhibitory peptide. Suitably, the autoinhibitory peptide comprises an amino acid sequence which binds the active site of a protease without being cleaved by the protease. Preferably, the autoinhibitory peptide competitively at least partly inhibits binding and cleavage of one or more protease substrates by the protease. In one embodiment, the autoinhibitory peptide is a specific inhibitor of an endopeptidase such as a cysteine protease. In a preferred embodiment, the autoinhibitory peptide is a specific inhibitor of a protease, preferably a cysteine protease, encoded by a viral genome.

More preferably, the autoinhibitory peptide is an inhibitor of a protease encoded by a Potyviral genome.

One particular embodiment of an autoinhibitory peptide is a specific inhibitor of a Potyvirus NIa protease, preferably encoded by a TEV, TVMV or SMV genome. Peptides that bind the active site of NIa proteases and inhibit their activity are generally derived from Site F which refers to a peptide sequence which separates the Mb RNA polymerase from the viral coat protein, and is considered the most efficient substrate for NIa proteases.

The autoinhibitory peptide may comprise an amino acid sequence that corresponds to at least a fragment of a substrate of the protease, but not an amino acid sequence of a protease cleavage site. In this regard, the autoinhibitory peptide may comprise an amino acid sequence of a protease cleavage site modified or engineered to resist cleavage by the protease.

In some embodiments, to improve binding of the autoinhibitory peptide to the protease, and thus achieve improved autoinhibition, one or more amino acid sequence mutations may be introduced into the amino acid sequence of the protease and/or the autoinhibitor. As will be described in more detail hereinafter in the Examples in embodiments relating to NIa protease of TVMV, modification of residues in the RETVRFQSDT (SEQ ID NO: 57) of the site F autoinhibitory peptide may improve auto-inhibition while minimizing or eliminating cleavage by TVMV protease.

Binding of the autoinhibitory peptide can also be improved by improving the linker region connecting the autoinhibitory (AI) domain to the NIa protease, such as by truncating the C-terminus of TVMV and increasing the effective concentration of the AI domain near the active site.

In other embodiments, autoinhibition can be improved by introducing beneficial steric constraints either through specific dimerization modules located at the N- and C-terminus of the protease biosensor or by circular permutation. Circularly permutated protease biosensors may feature two linker sites which can incorporate recognition sites for two different target proteases (see for example FIG. 5).

Persons skilled in the art will appreciate that the modifications described above in relation to NIa proteases and autoinhibitory peptides may be applied in principle to other proteases and/or autoinhibitory peptides suitable for use in biosensors.

Figure 7:
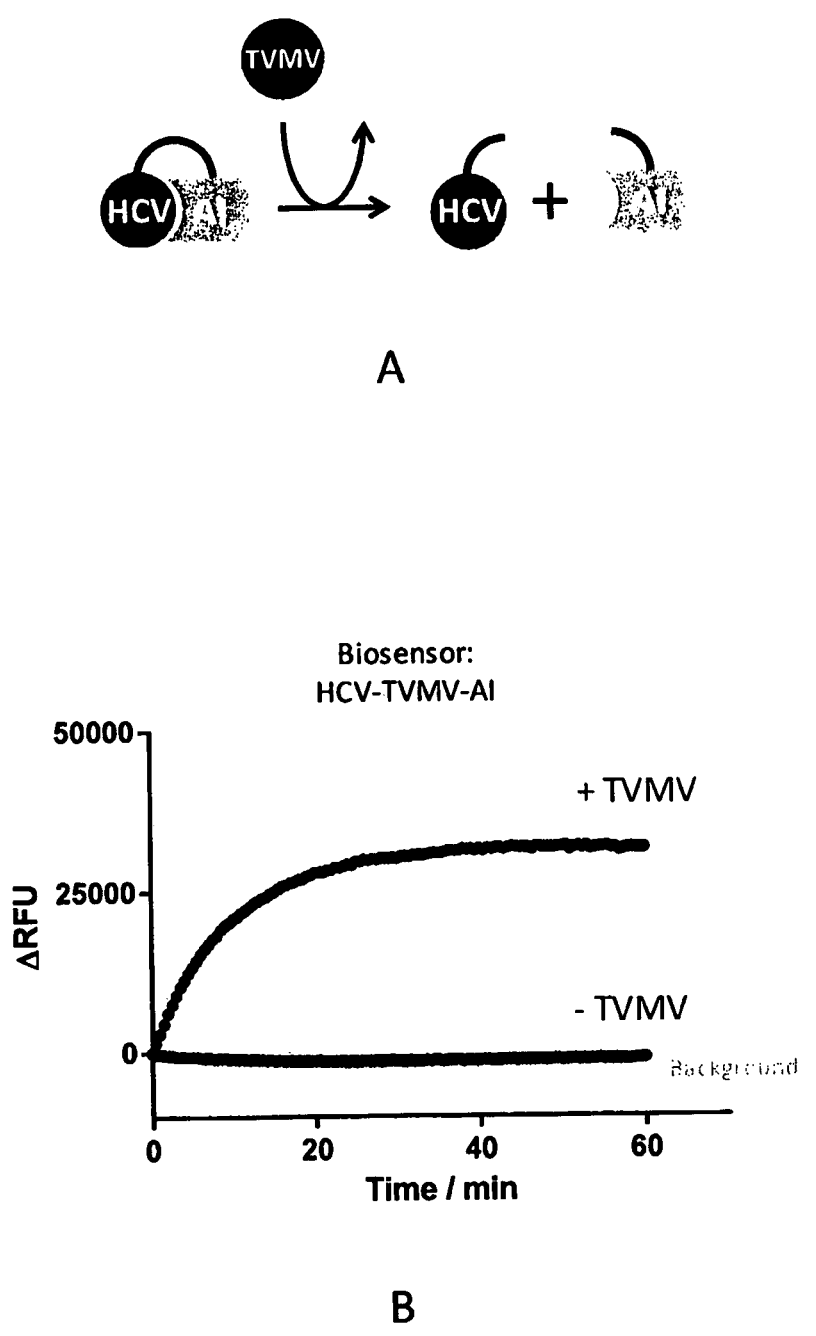

For example, in a manner analogous to NIa proteases, artificially autoinhibited signal transducers based on. HCV can be created by joining the peptide-based active site binder DELILCPLDL (SEQ ID NO:58) to its C-terminus via a linker comprising a TVMV cleavage site (FIG. 7A).

It will be appreciated from the foregoing that the biosensor molecule comprises at least one sensor comprising at least one sensor amino acid sequence responsive to at least one target molecule. In this context, a target molecule is a molecule whose presence or absence is to be detected by the sensor amino acid sequence of the biosensor.

As will be understood from the foregoing, in one form the biosensor molecule may be a single, unitary protein molecule comprising a single contiguous amino acid sequence. In an embodiment, the sensor amino acid sequence and the protease amino acid sequences may further comprise respective linker amino acid sequences, preferably contiguous with, or linked to, the N- or C-terminal amino acid of the protease amino acid sequence or the sensor amino acid sequence. The linker sequences may facilitate stabilization of the biosensor. In one particular embodiment, the respective linker amino acid sequences are capable of dimerization, such as the coiled-coil dimerization linkers schematically shown in FIG. 5.

In another form, the sensor amino acid sequence and the protease amino acid sequence are separate sequences. In one embodiment, the separate sensor amino acid sequence and the protease amino acid sequences comprise respective linker amino acid sequences. The linker sequences may facilitate association (e.g dimerization) of the separate amino acid sequences. The linker amino acid sequences may be contiguous with, or linked to, the N- and/or C-terminal amino acid of the protease amino acid sequence and/or the sensor amino acid sequence. In one particular embodiment, the respective linker amino acid sequences are capable of dimerization, such as the coiled-coil dimerization linkers schematically shown in FIG. 1.

In embodiments where the inhibitor of protease activity does not comprise an amino acid sequence (e.g. is a small organic molecule, nucleic acid etc), the inhibitor is suitably covalently coupled directly or indirectly to the sensor amino acid sequence responsive to the target molecule.

Covalent coupling may be achieved by standard chemical methods depending on the chemical structure of the inhibitor utilized.

The biosensor may comprise (i) a single sensor comprising a single amino acid sequence responsive to a single target molecule; (ii) two sensors comprising respective amino acid sequence responsive to the same target molecule; or (iii) two sensors comprising respective amino acid sequence responsive to different target molecules.

In some general embodiments, the sensor amino acid sequence is an amino acid sequence intermediate and contiguous with the protease amino acid sequence and the inhibitor amino acid sequence. A non-limiting example is schematically shown in FIG. 1.

In another embodiment, the sensor amino acid sequence is an amino acid sequence that is non-contiguous with a separate protease amino acid sequence and contiguous with, or containing, the inhibitor amino acid sequence. In this embodiment, respective linker amino acid sequences associate (e.g. dimerizing linkers) to join the separate amino acid sequences as hereinbefore described. A non-limiting example is schematically shown as in FIG. 1.

In an alternative embodiment, the biosensor comprises first and second sensors comprising respective sensor amino acid sequences.

By way of example, the biosensor molecule comprises: a protease amino acid sequence; first and second sensors that comprise first and second sensor amino acid sequences, the sensors responsive to the same or different target molecules; and an inhibitor of the protease activity of said protease amino acid sequence; wherein the biosensor is switchable between a protease active and a protease inactive state, or from a protease inactive to a protease active state when said sensor molecule responds to said target molecule.

Preferably, the first and second amino acid sequences respectively comprise a first protease cleavage site cleavable by a first protease target molecule and a second protease cleavage site cleavable by a second protease target molecule.

Suitably, the first and second sensors respectively comprise first and second, non-contiguous amino acid sequences. Preferably, each of the first and second non-contiguous amino acid sequences are contiguous with an amino acid sequence of the inhibitor of protease activity and with the protease amino acid sequence.

Figure 5:
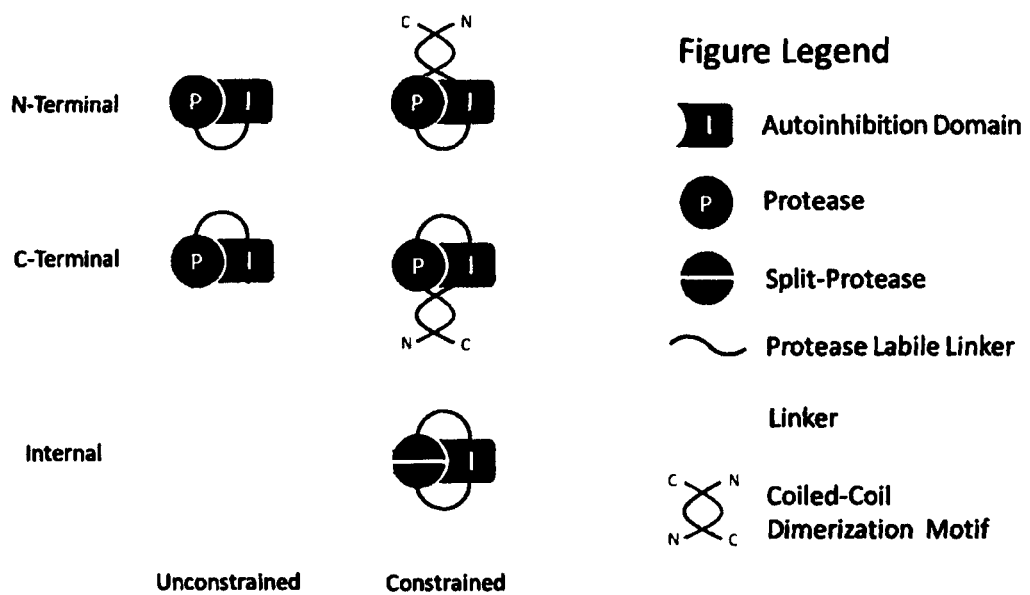
FIG. 5: Summary of autoinhibited protease biosensors. In addition to enhancing affinity interactions between the protease biosensor and the AI-domain by point mutations that introduce complementary hydrophobic and electrostatic contacts between the AI-domain and the biosensor protease, autoinhibition can also be improved by introducing beneficial steric constraints either through specific dimerization modules located at the N- and C-terminus of the protease biosensor or by circular permutation. Circularly permutated protease biosensors feature two linker sites which can incorporate recognition sites for two different target proteases.

This may be referred to as a "circularly permutated" biosensor. This embodiment may further comprise a "split protease" amino acid sequence. A non-limiting example is schematically shown in FIG. 5. The biosensor of this embodiment may comprise N- and C-terminal amino acid sequences at amino acid positions 118 and 119 of the protease. As a result, the inhibitor ("autoinhibitory domain") amino acid sequence is relocated to an internal position so that both its termini become constrained and form part of the sensor amino acid sequence that connects separate portions of the split-protease. While in the initial configuration the autoinhibitory domain is flanked with a protease cleavage site for a single target protease, this embodiment can contain the autoinhibitory domain flanked by recognition sequences for two or more different target proteases. The latter arrangement enables detection of more than one target protease (see FIG. 5 for example).

In one broad embodiment, the sensor amino acid sequence(s) responsive to the target molecule may respond to the presence of the target molecule by a change in structure, inclusive of a change in primary, secondary and/or tertiary structure.

In one form of embodiment, the sensor amino acid sequence responds to the presence of the target molecule by a change in primary structure. A preferred example of a change in primary structure is cleavage of at least one peptide bond of, or within, the sensor amino acid sequence by a target protease. Accordingly, the sensor amino acid sequence responsive to the target protease comprises a protease cleavage site that is responsive (i.e by proteolytic cleavage) to the presence of a target protease that is capable of proteolytically cleaving the amino acid sequence.

Preferably, the sensor amino acid sequence includes one or more "linker" amino acids N- and/or C-terminal of the target protease cleavage site.

Suitably, in one form of this embodiment the protease cleavage site in the sensor amino acid sequence is located intermediate the protease amino acid sequence and the inhibitor. Suitably, the protease cleavage site of the sensor amino acid sequence is not present in the protease amino acid sequence of the biosensor molecule or in an amino acid sequence of the inhibitor.

In another form of this embodiment, the protease cleacage site is in a sensor amino acid sequence that is non-contiguous with a separate protease amino acid sequence and contiguous with, or containing, the inhibitor amino acid sequence, as hereinbefore described.

The target protease may be any protease for which a protease cleavage site is known. Suitably, the target protease is different to the biosensor protease(s). In a preferred embodiment, the target protease is detectable in a biological sample obtainable from an organism, inclusive of bacteria, plants and animals. Animals may include humans and other mammals. Non-limiting examples of target proteases include proteases involved in blood coagulation such as thrombin, plasmin, factor VII, factor IX, factor X, factor Xa, factor XI, factor XII (Hageman factor) and other proteases such as kallikreins (e.g. kallikrein III, P-30 or prostate specific antigen), matrix metalloproteinases (such as involved in wounds and ulcers; e.g. MMP7 and MMP9), adamalysins, serralysins, astacins and other proteases of the metzincin superfamily, trypsin, chymotrypsin, elastase, cathepsin G, pepsin and carboxypeptidase A as well as proteases of pathogenic viruses such as HIV protease, West Nile NS3 protease and dengue virus protease although without limitation thereto.

In another form of this embodiment, the sensor amino acid sequence responds to the presence of the target molecule by a conformational change, such as a change in secondary and/or tertiary structure.

Suitably, the target molecule of this embodiment may be any molecule (such as an analyte) which is capable of binding the sensor amino acid sequence to thereby induce or promote the conformational change.

In one form of this embodiment, the conformational change comprises a change from an initial conformation that promotes or favours no or minimal biosensor protease inhibition by the inhibitor to a conformation that promotes or favours biosensor protease inhibition by the inhibitor.

In another form of this embodiment, the conformational change comprises a change from an initial conformation that promotes or favours biosensor protease inhibition by the inhibitor to a conformation that promotes or favours no or minimal biosensor protease inhibition by the inhibitor.

Suitably, the sensor amino acid sequence may comprise or be linked to an amino acid sequence of at least a fragment of any protein or protein domain that responds to a target molecule by a conformational change. In this regard, the target molecule may be a protein inclusive of antibodies and antibody fragments, antigens, phosphoproteins, glycoproteins, lipoproteins and glycoproteins, lipid, phospholipids, carbohydrates inclusive of simple sugars, disaccharides and polysaccharides, nucleic acids, nucleoprotein or any other molecule or analyte capable of binding the sensor and inducing or promoting a conformational change therein. By way of example only, the sensor amino acid sequence may comprise or be linked to: (i) an amino acid sequence of a ligand binding domain of a receptor responsive to binding of a target molecule such as a cognate growth factor, cytokine, a hormone (e.g. insulin), neurotransmitters etc; (ii) an amino acid sequence of an ion or metabolite transporter responsive to binding of a target molecule such as an ion or metabolite (e.g a $Ca^{2+}$ or glucose transporter); (iii) a zinc finger amino acid sequence responsive to zinc-dependent binding a DNA target molecule; (iv) a helix-loop-helix amino acid sequence responsive to binding a DNA target molecule; (v) a pleckstrin homology domain amino acid sequence responsive to binding of a phospoinositide target molecule; (vi) an amino acid sequence of a Src homology 2- or Src homology 3-domain responsive to a signaling protein; (vii) an amino acid sequence of an antigen responsive to binding of an antibody target molecule; or (viii) an amino acid sequence of a protein kinase or phosphatase responsive to binding of a phosphorylatable or phosphorylated target molecule; (ix) ubiquitin-binding domains and modified or engineered versions thereof, although without limitation thereto.

In one particular embodiment, the sensor amino acid sequence of the biosensor comprises, or is linked to, an amino acid sequence of an affinity clamp. The affinity clamp preferably comprises a recognition domain and, optionally, an enhancer domain. The recognition domain is typically capable of binding one or more target molecules, such as described in (i)-(ix) above. Recognition domains may include, but are not limited to, domains involved in phoshotyrosine binding (e.g. SH2, PTB), phospho-serine binding (e.g. UIM, GAT, CUE, BTB/POZ, VHS, UBA, RING, HECT, WW, 14-3-3, Polo-box), phospho-threonine binding (e.g. FHA, WW, Polo-box), proline-rich region binding (e.g. EVH1, SH3, GYF), acetylated lysine binding (e.g. Bromo), methylated lysine binding (e.g. Chromo, PHD), apoptosis (e.g. BIR, TRAF, DED, Death, CARD, BH), cytoskeleton modulation (e.g. ADF, GEL, DH, CH, FH2), ubiquitin-binding domains or modified or engineered versions thereof, or other cellular functions (e.g. EH, CC, VHL, TUDOR, PUF Repeat, PAS, MH1, LRR1, IQ, HEAT, GRIP, TUBBY, SNARE, TPR, TIR, START, SOCS Box, SAM, RGS, PDZ, PB1, F-BOX, ENTH, EF-Hand, SHADOW, ARM, ANK).

The enhancer domain typically increases or enhances the binding affinity for at least one or the target molecules. In some embodiments, the affinity may be increased by at least 10, 100 or 1000 fold compared to that of the recognition domain alone. The affinity clamp may further comprise linker connecting the recognition domain and the enhancer domain.

In one particular embodiment, the affinity clamp comprises a recognition domain that comprises at least a portion or fragment of a PDZ domain and an enhancer domain that comprises at least a portion or fragment of a fibronectin type III domain. The PDZ domain may be derived from a human Erbin protein. Erbin-PDZ binds to target molecules such as the C-termini of p120-related catenins (such as δ-catenin and Armadillo repeat gene deleted in Velo-cardio-facial syndrome (ARVCF)). Preferably, this embodiment of the affinity claim further comprises the tenth (10$^{th}$) type III (FN3) domain of human fibronectin as an enhancer domain. Non-limiting examples of this embodiment are set forth in SEQ ID NOS:21-27.

In some embodiments, the afffinity clamp may comprise one or more connector amino acid sequences. For example, a connector amino acid sequence may connect the protease amino acid sequence (such as comprising a TVMV protease sequence) to the Erbin-PDZ domain, the Erbin-PDZ domain to the FN3 domain and/or the FN3 domain to the inhibitor.

In the embodiments described with reference to SEQ ID NOS:21-27, the conformational change comprises a change from an initial affinity clamp conformation. This conformational change may promote or favour no or minimal biosensor protease inhibition by the inhibitor to an affinity clamp conformation in response to a target molecule that promotes or favours biosensor protease inhibition by the inhibitor, or promote or favour biosensor protease inhibition by the inhibitor to an affinity clamp conformation in response to a target molecule that promotes or favours biosensor protease no or minimal inhibition by the inhibitor.

Reference is also made to WO2009/062170, Zhuang & Liu, 2011, Comput. Theoret. Chem. 963 448, Huang et al, 2009, J. Mol. Biol. 392 1221 and Huang et al., 2008, PNAS (USA) 105 6578 for a more detailed explanation of affinity clamp structure and function.

In an alternative embodiment, the sensor amino acid sequence comprises one or more epitopes that can be bound by an antibody target molecule.

Suitably, the conformational change comprises a change from an initial conformation that promotes or favours biosensor protease inhibition by the inhibitor to a conformation in response to an antibody target molecule that promotes or favours release of the biosensor protease from inhibition by the inhibitor.

In use, when the antibody target molecule binds the epitopes, the epitopes are effectively spatially separated thereby allowing the biosensor to adopt an "open", activated conformation.

A particular example of this embodiment is described in FIG. 12. In the particular embodiment shown in FIG. 12, the biosensor further comprises a coiled coil dimerization motif which facilitates retaining the biosensor in a "closed", inactive conformation until antibody binding.

In some embodiments, the biosensor may further comprise a binding partner which improves, augments, assists or stabilizes a specific interaction between a target molecule and the sensor. The binding partner may be any molecule with specificity for the target molecule. The binding partner may be, or comprise a protein such as a peptide, antibody, antibody fragment or any other protein scaffold that can be suitably engineered to create or comprise a binding portion, domain or region (e.g. reviewed in Binz et al., 2005 Nature Biotechnology, 23, 1257-68.) which binds a target molecule.

In one embodiment, the binding partner may be an antibody or antibody fragment, inclusive of monoclonal and polyclonal antibodies, recombinant antibodies, Fab and Fab'2 fragments, diabodies and single chain antibody fragments (e.g. scVs), although without limitation thereto.

In one particular embodiment, the biosensor may further comprise an antibody-binding molecule, wherein the antibody has specificity for a target molecule. The antibody-binding molecule is preferably an amino acid sequence of protein A, or a fragment thereof (e.g a ZZ domain), which binds an Fc portion of the antibody. Particular examples of this embodiment are described in FIG. 10.

Suitably, the binding partner binds a protease target molecule. Accordingly, the sensor amino acid sequence comprises a cleavage site for the protease target molecule.

One potential problem foreseen by the inventors is that of possible incomplete or truncated translation of the amino acid sequence of the biosensor when produced using recombinant expression systems.

In one embodiment, the biosensor is a recombinant protein that comprises an affinity tag at a C-terminus thereof, which affinity tag facilitates isolation of biosensor molecules where protein translation has proceeded to the C-terminus of the protein product. The affinity tag suitably comprises an amino acid sequence of an epitope tag, fusion partner or other moiety that facilitates isolation of the biosensor molecule.

Well known examples of fusion partners include, but are not limited to, glutathione-S-transferase (GST), maltose binding protein (MBP) and metal-binding moieties such as polyhistidine (e.g. $HIS_6$), for which affinity purification reagents are well known and readily available. Epitope tags are usually short peptide sequences for which a specific antibody is available. Well-known examples of epitope tags for which specific monoclonal antibodies are readily available include c-myc, influenza virus haemagglutinin and FLAG tags.

Preferably, the affinity tag is a C-terminal hexahistidine ($HIS_6$) tag.

Particular embodiments of the biosensor are provided in SEQ ID NOS:1-28, wherein SEQ ID NO:1-20 are embodiments of a biosensor suitable for detecting a protease analyte and wherein SEQ ID NOS:21-27 is an embodiment of biosensor comprising an affinity clamp. SEQ ID NO:28 is an amino acid sequence of an embodiment of a biosensor that comprises an interacting domain that is capable of binding an amplifier molecule, as will be discussed in more detail hereinafter.

It will also be appreciated that the invention includes biosensor molecules that are variants of the embodiments described in SEQ ID NOS:1-28, or which comprise variants of the constituent protease, sensor and/or inhibitor amino acid sequences in SEQ ID NOS:1-28 or otherwise disclosed herein. Typically, such variants have at least 80%, at least 85%, at least 90%, 91%, 92%, 93%, 94% 95% 96%, 97%, 98% or 99% sequence identity with any of the amino acid sequences set forth in SEQ ID NOS:1-28 or otherwise disclosed herein. By way of example only, conservative amino acid variations may be made without an appreciable or substantial change in function. For example, conservative amino acid substitutions may be tolerated where charge, hydrophilicity, hydrophobicity, side chain "bulk", secondary and/or tertiary structure (e.g. helicity), target molecule binding, protease activity and/or protease inhibitory activity are substantially unaltered or are altered to a degree that does not appreciably or substantially compromise the function of the biosensor.

The term "sequence identity" is used herein in its broadest sense to include the number of exact amino acid matches having regard to an appropriate alignment using a standard algorithm, having regard to the extent that sequences are identical over a window of comparison. Sequence identity may be determined using computer algorithms such as GAP, BESTFIT, FASTA and the BLAST family of programs as for example disclosed by Altschul et al., 1997, Nucl. Acids Res. 25 3389. A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

Protein fragments may comprise up to 5%, 10%, 15%, 20%, 25%, 30%, 35%, 40%, 45%, 50%, 55%, 60%, 65%, 70%, 75%, 80%, 85%, 90% or up to 95-99% of an amino acid sequence set forth in any one of SEQ ID NOS:1-28. In some embodiments, the protein fragment may comprise up to 10, 20, 40, 50, 70, 80, 90, 100, 120, 150, 180 200, 220 or 230 amino acids an amino acid sequence set forth in any one of SEQ ID NOS:1-28.

A further aspect of the invention provides a kit or composition comprising one or more biosensors disclosed herein in combination with one or more substrates.

The biosensor disclosed herein is particularly suitable for detection of a target molecule. The target molecule may be any molecule which can be detected by the sensor amino acid sequence, such as hereinbefore described.

Suitably, the substrate is a peptide which comprises a label.

As is well understood in the art, the label may be selected from a group including an enzyme, a fluorophore, a chemiluminescent molecule, biotin, radioisotope or other label.

Examples of suitable enzyme labels useful in the present invention include alkaline phosphatase, horseradish peroxidase, luciferase, β-galactosidase, glucose oxidase, lysozyme, malate dehydrogenase and the like. The enzyme label may be used alone or in combination with a second enzyme in solution or with a suitable chromogenic or chemiluminescent substrate.

Examples of chromogens include diaminobanzidine (DAB), permanent red, 3-ethylbenzthiazoline sulfonic acid (ABTS), 5-bromo-4-chloro-3-indolyl phosphate (BCIP), nitro blue tetrazolium (NBT), 3,3',5,5'-tetramethyl benzidine (TNB) and 4-chloro-1-naphthol (4-CN), although without limitation thereto.

A non-limiting example of a chemiluminescent substrate is Luminol™, which is oxidized in the presence of horseradish peroxidase and hydrogen peroxide to form an excited state product (3-aminophthalate).

Radioisotope labels may include $^{125}$I, $^{131}$I, $^{51}$Cr and $^{99}$Tc, although without limitation thereto.

Fluorophores may be a coumarin, fluorescein isothiocyanate (FITC), tetramethylrhodamine isothiocyanate (TRITC), allophycocyanin (APC), Texas Red (TR), TAMRA, LC red, HEX, FAM, TET, ROX, Cy dyes such as Cy3 or Cy5 or R-Phycoerythrin (RPE) or derivatives thereof, although without limitation thereto.

Preferably, the label is a fluorophore. A preferred fluorophore is a coumarin such as 7-methoxycoumarin-4-acetic acid.

In a preferred embodiment where the label is a fluorophore, the substrate peptide may be quenched, whereby release of the fluorophore from quenching is detected as an increase in fluorescence signal. Non-limiting examples of quenchers include 5-amino-2-nitrobenzoic acid (ANA), Deep Dark Quenchers (DDQ), Iowa Black quenchers, Black Hole quenchers, Eclipse quenchers, Dabcyl and QSY quenchers which are commercially available from sources such as Eurogentec, Integrated DNA Technologies and Molecular Probes.

It will therefore be appreciated that in one embodiment, activation of the biosensor may be measured by the biosensor proteolytically cleaving a substrate, such as a fluorescently labeled peptide, to thereby facilitate detection of the presence of a target molecule in a sample.

According to this embodiment, the substrate peptide comprises a cleavage site specific to the protease of the biosensor. Preferably, detection of the label (e.g a fluorophore) occurs as a result of cleavage of the substrate.

In another embodiment, detection can be facilitated by one or more amplifier molecules.

According to this embodiment, activation of the biosensor may be measured by the biosensor proteolytically cleaving one or more amplifier molecules.

Accordingly, the invention provides a composition comprising one or more biosensors in combination with one or more amplifier molecules and one or more substrates for the amplifier molecule(s).

The amplifier molecule suitably comprises: (i) an amino acid sequence of at least a fragment of a protease that is different to the protease of the biosensor; (ii) an inhibitor of the protease of (i); and (iii) a linker amino acid sequence which comprises a cleavage site for the protease of the biosensor.

In this embodiment, the substrate peptide does not comprise a cleavage site for the protease of the biosensor but comprises a cleavage site cleavable by the different protease of the amplifier molecule. Accordingly, the substrate peptide is not cleaved by activation of the protease of the biosensor. Rather, activation of the protease activity of the biosensor results in cleavage of the the cleavage site in (iii) of the amplifier molecule, thereby releasing inhibition of the protease activity of the amplifier molecule.

Suitably, the substrate peptide of this embodiment comprises a cleavage site specific for the different protease of the amplifier molecule but which is not cleavable by the protease of the isolated sensor molecule.

In a particular embodiment, the biosensor may be linked or coupled to the amplifier molecule. For example, the biosensor and amplifier molecule may comprise respective interacting domains (i.e an amplifier interacting domain and a biosensor interacting domain) that facilitate releasable linking or coupling of the biosensor and amplifier molecules. Non-limiting examples of interacting domains include leucine zipper motifs, SH3:SH3 binding peptides, FRB:FKBP protein domains, etc. The interacting domain could also be created by attaching the biosensor and the amplifier molecule to proteins or organic molecules capable of undergoing polymerisation or fibre formation. Non-limiting examples of this particular embodiment are shown schematically in FIG. 9 and FIG. 13. According to these embodiments, the amplifier molecule protease is derived from HCV.

Figure 9:
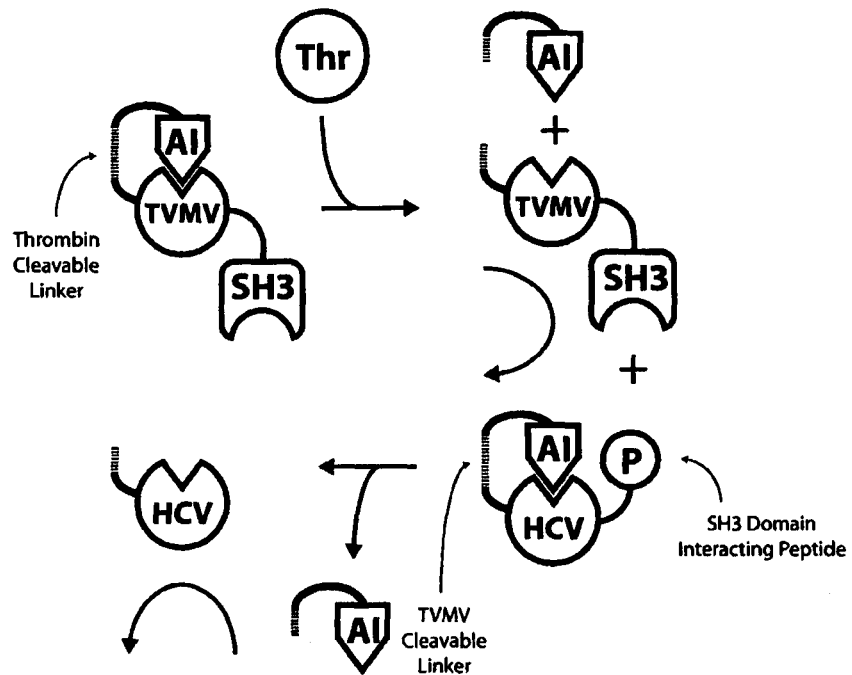
FIG. 9: Summary of direct affinity targeting with SH3-domain:SH3-peptide interactions. The sensitivity of the TVMV-inducible biosensor based on HCV can be improved by fusion TVMV- and HCV-based signal transducers with SH3-domains and an SH3-domain interacting peptides. In this way, the concentration between the TVMV- and HCV-based signal transducers is increased leading to accelerated activation of the HCV-based signal transducer.
Figure 9:
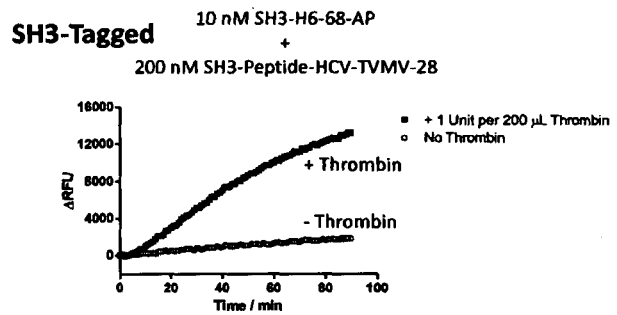
Figure 9:
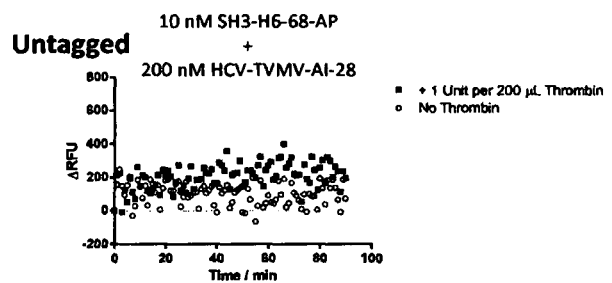

In FIG. 9, the protease activity of the biosensor is proteolytically activated by a target protease cleaving a protease cleavage site in the sensor amino acid sequence.

Figure 13:
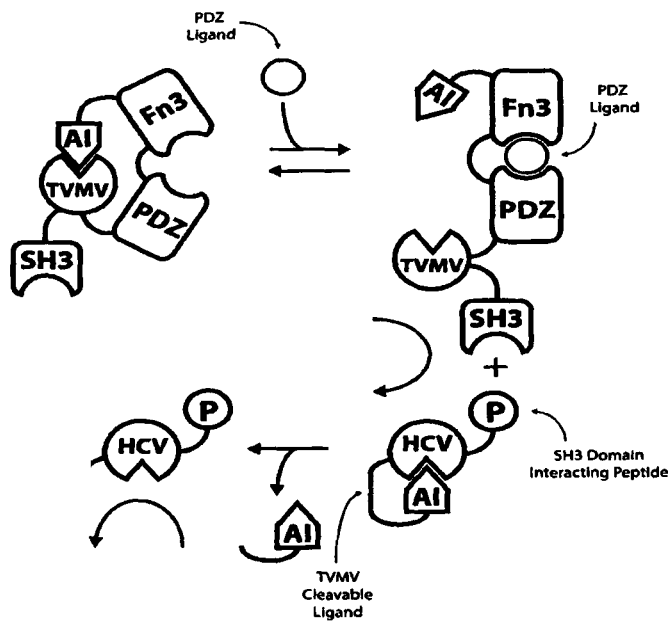
FIG. 13: An integrated signal sensing and amplification circuit. The sensitivity of the allosterically regulated protease based on TVMV can be improved by coupling it to an HCV-based signal transducer. Affinity targeting based on SH3-domain:SH3-peptide interactions is essential to ensure efficient coupling between the allosterically regulated protease and the HCV-based signal transducer.
Figure 13:
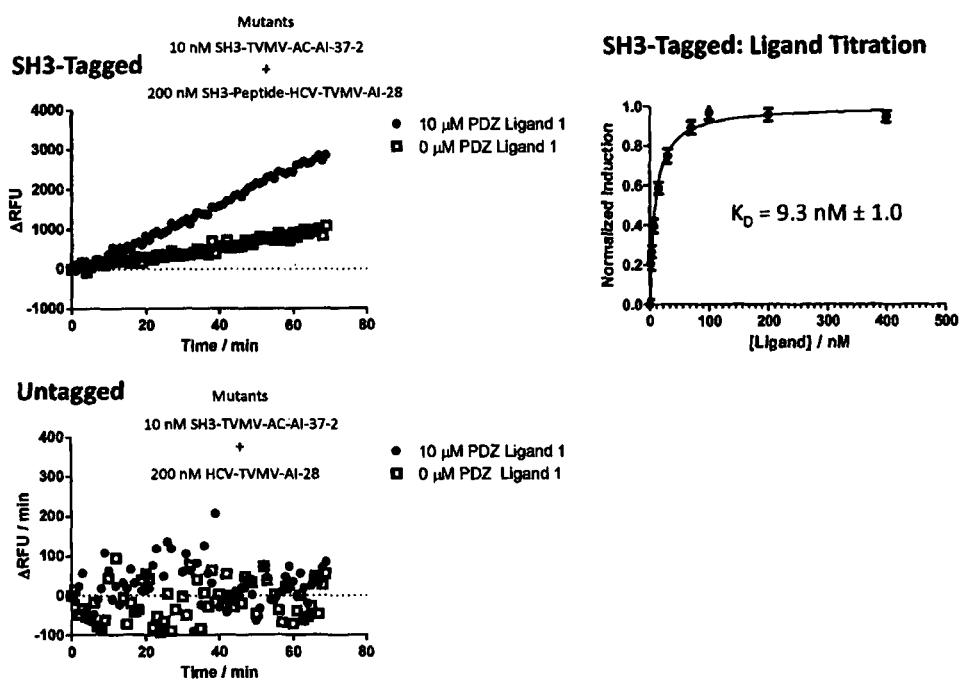

In FIG. 13, the protease activity of the biosensor is allosterically activated by way of an interaction between the target molecule and an affinity clamp.

In a further form of this embodiment, the composition may further comprise one or more deactivating molecules.

The deactivating molecule suitably comprises: (i) an amino acid sequence of a protease that is different to the protease of the biosensor and that is different to the protease of the amplifier molecule; (ii) an inhibitor of the protease of (i); and (iii) a linker amino acid sequence which comprises a cleavage site for the protease of the amplification molecule.

According to this further form, activation of the protease activity of the amplification molecule results in the cleavage of the site in (iii) of the amplifier molecule, thereby releasing inhibition of the protease activity of the deactivating molecule. Suitably, the biosensor comprises an inactivating cleavage site specific for the protease of the deactivating molecule. Accordingly, activation of the protease activity of the deactivating molecule results in cleavage of the inactivating cleavage site which thereby substantially eliminates the protease activity of the biosensor.

It will therefore be appreciated that by manipulating the respective concentrations and/or activities of (a) the biosensor; (b) the amplifier molecule; and (c) the deactivating molecule, an appropriate level of signal amplification may be achieved to facilitate detection of the target molecule.

Reference is also made to FIG. 1 which provides a schematic summary of certain embodiments of the biosensor, the amplifier molecule and the deactivating molecule described herein.

It will be appreciated that in certain aspects, the biosensor disclosed herein may have efficacy in molecular diagnostics wherein the "target molecule" is an analyte or other molecule of diagnostic value or importance.

In a further aspect, the invention provides a method of detecting a target molecule, said method including the step of contacting the composition of the aforementioned aspect with a sample to thereby determine the presence or absence of the target molecule in the sample.

Suitably, the sample is a biological sample. Biological samples may include organ samples, tissue samples, cellular samples, fluid samples or any other sample obtainable, obtained, derivable or derived from an organism or a component of the organism. The biological sample can comprise a fermentation medium, feedstock or food product such as for example, but not limited to, dairy products.

In particular embodiments, the biological sample is obtainable from a mammal, preferably a human. By way of example, the biological sample may be a fluid sample such as blood, serum, plasma, urine, saliva, cerebrospinal fluid or amniotic fluid, a tissue sample such as a tissue or organ biopsy or may be a cellular sample such as a sample comprising red blood cells, lymphocytes, tumour cells or skin cells, although without limitation thereto. A particular type of biological sample is a pathology sample.

Suitably, the protease activity of the biosensor is not substantially inhibited by components of the sample (e.g. serum proteins, metabolites, cells, cellular debris and components, naturally-occurring protease inhibitors etc). Embodiments where the protease is of Potyvirus origin such as hereinbefore described may be particularly resistant to inhibition by components of human or mammalian biological samples.

In a particular embodiment, the method is for diagnosis of a disease or condition of a human.

Accordingly, a preferred aspect of the invention provides a method of diagnosis of a disease or condition in a human, said method including the step of contacting the composition of the aforementioned aspect with a biological sample obtained from the human to thereby determine the presence or absence of a target molecule in the biological sample, determination of the presence or absence of the target molecule facilitating diagnosis of the disease or condition.

The disease or condition may be any where detection of a target molecule assists diagnosis. Non limiting examples of target molecules or analytes include blood coagulation factors such as previously described, kallikreins inclusive of PSA, matrix metalloproteinases, viral and bacterial proteases, antibodies, glucose, triglycerides, lipoproteins, cholesterol, tumour antigens, lymphocyte antigens, autoantigens and autoantibodies, drugs, salts, creatinine, blood serum or plasma proteins, pesticides, uric acid, products and intermediates of human and animal metabolism and metals.

This preferred aspect of the invention may be adapted to be performed as a "point of care" method whereby determination of the presence or absence of the target molecule may occur at a patient location which is then either analysed at that location or transmitted to a remote location for diagnosis of the disease or condition.

One particular aspect of the invention therefore provides a device for providing a disease diagnosis from a diagnostic target result obtained according to the method of the aforementioned aspect, the device comprising:

a processor; and a memory coupled to the processor, the memory including computer readable program code components that, when executed by the processor, perform a set of functions including:

analysing the diagnostic target result and providing a diagnosis of the disease or condition.

Another particular aspect of the invention therefore provides a device for communicating a diagnostic target result obtained according to the method of the aforementioned aspect, the device comprising:

a processor; and a memory coupled to the processor, the memory including computer readable program code components that, when executed by the processor, perform a set of functions including:

transmitting a diagnostic target result to a receiving device; and optionally receiving a diagnosis of the disease or condition from the or another receiving device.

The device may be in the form of a mobile or cellular phone, a computer or any other electronic device capable of analysing diagnostic target results at the "point of care" or transmitting and/or receiving information (i.e. diagnostic target results and a disease diagnosis) to or from a receiving device at a remote location.

Diagnostic aspects of the invention may also be in the form of a device comprising a cell or chamber that contains the biosensor and, optionally, an amplifier molecule. In some embodiments, the cell or chamber may be a component of, or connected or coupled to, a "point of care" device such as hereinbefore described.

Suitably, the cell or chamber is perfused with a sample and protease activity is detected.

In one embodiment, protease activity is detected electrochemically. For example, detection may be by digesting a protein or peptide clot covering the surface of the electrode, whereby protease digestion of the clot enables access of an electrolyte to the electrode. In another example, activating the enzyme changes conductivity of a solution in the cell. In yet another example, the protease activity of the biosensor digests a conducting substrate and thereby changes conductivity. In a further example, the protease activity of the biosensor induces a substrate molecule or enzyme to become electrochemically active.

In another embodiment, protease activity is detected acoustically. For example, detection may be by measuring propagation of sound waves due to changes in viscosity of gels and solutions comprising one or more substrates of the protease.

In another embodiment, protease activity is detected optically. For example, detection may be by monitoring changes in reflection or refraction of light from surfaces comprising (e.g coated or impregnated with) one or more substrates of the protease.

A further embodiment of the invention relates to imaging of biological molecules. In one embodiment of the invention the biosensor is activated by metalloproteases secreted by a tumour. The activated protease activity of the biosensor molecule cleaves a substrate peptide designed to change fluorescence and circulation time upon cleavage. This, for instance, may be brought about by the exposure of hydrophobic, or a cell-penetrating sequence and dequenching of a fluorophore.

Alternatively the substrate peptide may be modified with a contrast substance such as metal (Ba) or an isotope for whole body imaging.

An advantage of the invention over the targeting of a particular tumour protease directly is in signal amplification and standardisation of the targeting peptide. Further the specificity of the response may be increased by targeting of the biosensor to a particular cell type or surface antigen by fusing or conjugating it to a targeting domain comprising a peptide, antibody or other targeting molecule.

In a further embodiment, the biosensor comprises an affinity clamp targeted to a particular type of surface molecule such as, for example, EGF receptor enriched in certain tumours. Activation of the proteolytic activity of the isolated biosensor can be used for tumour visualisation or therapeutic targeting.

In a still further embodiment, an array of biosensors is connected or coupled to one or more electronic devices that utilise the 'point of care" diagnostic device for identification of infective species. This embodiment is based on the observation that surface and secreted proteases play a key role in invasion and propagation of metazoan, bacterial and viral parasites. Each infective species can be categorized according to the unique protease signature. In a variation of the above described embodiment, the sensor array is composed of biosensors activated by metabolites and/or proteins of a parasitic organism.

Diagnostic aspects of the invention may also be in the form of a kit comprising one or a plurality of different biosensors capable of detecting one or a plurality of different target molecules. In this regard, a kit may comprise an array of different biosensors capable of detecting a plurality of different target molecules. The kit may further comprise one or more amplifier molecules, deactivating molecules and/or labeled substrates, as hereinbefore described. The kit may also comprise additional components including reagents such as buffers and diluents, reaction vessels and instructions for use.

A further aspect of the invention provides an isolated nucleic acid which encodes an amino acid sequence of the biosensor of the invention, or a variant thereof as hereinbefore defined.

The term "nucleic acid" as used herein designates single- or double-stranded mRNA, RNA, cRNA, RNAi, siRNA and DNA inclusive of cDNA, mitochondrial DNA (mtDNA) and genomic DNA.

A "polynucleotide" is a nucleic acid having eighty (80) or more contiguous nucleotides, while an "oligonucleotide" has less than eighty (80) contiguous nucleotides. A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™. A "probe" may be a single or double-stranded oligonucleotide or polynucleotide, suitably labelled for the purpose of detecting complementary sequences in Northern or Southern blotting, for example.

In particular embodiments, the isolated nucleic acid encodes an amino acid sequence selected from the group consisting of: SEQ ID NOS:1-28 or a variant thereof.

In even more particular embodiments, the isolated nucleic acid comprises a nucleotide sequence set forth in SEQ ID NOS:29-56.

The invention also provides variants and/or fragments of the isolated nucleic acids. Variants may comprise a nucleotide sequence at least 70%, at least 75%, at least 80%, at least 85%, at least 90%, 91%, 93%, 94%, 95%, 96%, 97%, 98% or 99% nucleotide sequence identity with any one of SEQ ID NOS:29-56. In other embodiments, nucleic acid variants may hybridize with the nucleotide sequence of any one of SEQ ID NOS:29-56 under high stringency conditions.

Fragments may comprise up to 5%, 10%, 15%, 20%, 25%, 30%, 35%, 40%, 45%, 50%, 55%, 60%, 65%, 70%, 75%, 80%, 85%, 90% or 95-99% of the contiguous nucleotides present in any one of SEQ ID NOS:29-56, The invention also provides "genetic constructs" that comprise one or more isolated nucleic acids, variants or fragments thereof as disclosed herein operably linked to one or more additional nucleotide sequences.

As generally used herein, a "genetic construct" is an artificially created nucleic acid that incorporates, and/or facilitates use of, an isolated nucleic acid disclosed herein.

In particular embodiments, such constructs may be useful for recombinant manipulation, propagation, amplification, homologous recombination and/or expression of said isolated nucleic acid.

As used herein, a genetic construct used for recombinant protein expression is referred to as an "expression construct", wherein the isolated nucleic acid to be expressed is operably linked or operably connected to one or more additional nucleotide sequences in an expression vector.

An "expression vector" may be either a self-replicating extra-chromosomal vector such as a plasmid, or a vector that integrates into a host genome.

In this context, the one or more additional nucleotide sequences are regulatory nucleotide sequences.

By "operably linked" or "operably connected" is meant that said regulatory nucleotide sequence(s) is/are positioned relative to the nucleic acid to be expressed to initiate, regulate or otherwise control expression of the nucleic acid.

Regulatory nucleotide sequences will generally be appropriate for the host cell used for expression. Numerous types of appropriate expression vectors and suitable regulatory sequences are known in the art for a variety of host cells.

One or more regulatory nucleotide sequences may include, but are not limited to, promoter sequences, leader or signal sequences, ribosomal binding sites, transcriptional start and termination sequences, translational start and termination sequences, splice donor/acceptor sequences and enhancer or activator sequences.

Constitutive or inducible promoters as known in the art may be used and include, for example, nisin-inducible, tetracycline-repressible, IPTG-inducible, alcohol-inducible, acid-inducible and/or metal-inducible promoters.

In one embodiment, the expression vector comprises a selectable marker gene. Selectable markers are useful whether for the purposes of selection of transformed bacteria (such as bla, kanR, ermB and tetR) or transformed mammalian cells (such as hygromycin, G418 and puromycin resistance).

Suitable host cells for expression may be prokaryotic or eukaryotic, such as bacterial cells inclusive of *Escherichia coli* (DH5α for example), yeast cells such as *S. cerivisiae* or strates and PDZ peptide ligands were obtained commercially (Mimotopes) and dissolved in DMSO to a final concentration of 8 mM and stored at −80° C. (Table 1).

TABLE 1

List of peptide substrates and ligands used to assay the activities of different potyviral NIa proteases and the NS3 protease of HCV. ANA-denotes 5-amino-2-nitrobenzoic acid, (164) denotes L-Lysine (7-methoxycoumarin-4-acetic acid) and $NH_2$-denotes an amide at the C-terminus.

| Protease | Sequence | Comments |
|---|---|---|
| TEV | ANA-ENLYFQSDT(164)-$NH_2$ (SEQ ID NO: 59) | Contains additional Asp residues for improved water solubility. |
| TEV-DD | ANA-ENLYFQSDT(164)DD-$NH_2$ (SEQ ID NO: 60) | |
| TVMV | ANA-GETVRFQSDT(164)-$NH_2$ (SEQ ID NO: 61) | Contains additional Asp residues for improved water solubility. |
| TVMV-DD | ANA-GETVRFQSDT(164)DD-$NH_2$ (SEQ ID NO: 62) | |
| SMV | ANA-GEDVFHQSGS(164)-$NH_2$ (SEQ ID NO: 63) | Contains additional Asp residues for improved water solubility. |
| SMV-DD | ANA-GEDVFHQSGS(164)DD-$NH_2$ (SEQ ID NO: 64) | |
| HCV | ANA-DDVTPCSMS(164)-$NH_2$ (SEQ ID NO: 65) | |
| PDZ-Ligand 1 | $NH_2$-RGSIDTWV-COOH (SEQ ID NO: 66) | Higher Affinity Ligand $K_D$ ~0.625 nM for ePDZ-b1 |
| PDZ-Ligand 2 | $NH_2$-PQPVDSWV-COOH (SEQ ID NO: 67) | Lower Affinity Ligand $K_D$ ~5 nM for ePDZ-b1 |

*Pichia pastoris*, insect cells such as SF9 cells utilized with a baculovirus expression system, or any of various mammalian or other animal host cells such as CHO, BHK or 293 cells, although without limitation thereto.

Introduction of expression constructs into suitable host cells may be by way of techniques including but not limited to electroporation, heat shock, calcium phosphate precipitation, DEAE dextran-mediated transfection, liposome-based transfection (e.g. lipofectin, lipofectamine), protoplast fusion, microinjection or microparticle bombardment, as are well known in the art.

Purification of the recombinant biosensor molecule may be performed by any method known in the art. In preferred embodiments, the recombinant biosensor molecule comprises a fusion partner (preferably a C-terminal His tag) which allows purification by virtue of an appropriate affinity matrix, which in the case of a His tag would be a nickel matrix or resin.

So that the invention may be readily understood and put into practical effect, embodiments of the invention will be described with reference to the following non-limiting Examples.

EXAMPLES

Materials and Methods

Materials

Synthetic oligonucleotides and gBlocks were obtained commercially (IDT DNA). RET-quenched protease sub- Cloning Procedures and Plasmids The genes coding for NIa proteases, NS3 proteases, SH3 domains, SH3 domain interacting peptides, PSA-specific VHH domains, ZZ-domains, PDZ ligand binding domains (also known as 'affinity clamps'), fibronectin scaffolds, protease recognition sites, linkers and autoinhibition domains were either prepared by PCR or overlap extension of synthetic oligonucleotides using standard procedures or derived from synthetic gene fragments. DNA fragments were assembled according to desired specifications with USER Enzyme based methods similar to previously published procedures (Stein, V., M. Kaltenbach, and F. Hollfelder, *Assembling linear DNA templates for in vitro transcription and translation*. Methods Mol Biol, 2012. 815: p. 67-78; Villiers, B. R., V. Stein, and F. Hollfelder, *USER friendly DNA recombination (USERec): a simple and flexible near homology-independent method for gene library construction*. Protein Eng Des Sel, 2010. 23(1): p. 1-8). Alternatively, DNA fragments were assembled according to desired specifications by Gibson Assembly similar to previously published procedures (Gibson, D. G. et. al. *Enzymatic assembly of DNA molecules up to several hundred kilobases*. Nature Methods, 2009, 6, p. 343-345).

The fully assembled DNA fragments constructed by USER Enzyme based methods were generally purified by agarose gel electrophoresis and inserted into the MBP fusion expression vector via NcoI and BamHI sites using T4 DNA ligase or by means of Gibson Assembly.

Figure 2:
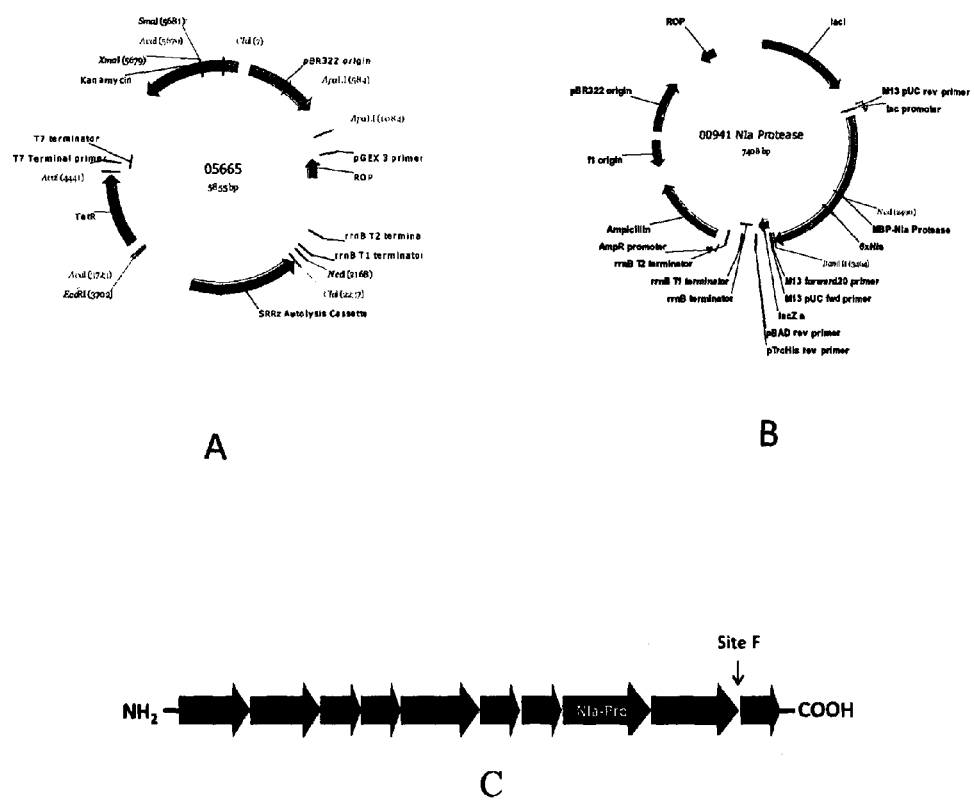
FIG. 2: Plasmid 05665 (A) carries the SRRz autolysis system derived from bacteriophage λ (Xu et al., 2006, 41 319) under the control of a tetracycline inducible promoter and was used for the high-throughput lysis of cell cultures in 96 well plates; Plasmid 00941 (B) served as the backbone for lactose dependent protein expression of different MBP-NIa protease fusion protein constructs (Kapust et al., 1999, Protein Sci. 8 1668) and their derivative biosensors; and (C) schematic representation of the viral polyprotein proteome.

Plasmids are shown in FIG. 2.

Screening for Protease Biosensors

Bacterial Growth Media and Protease Assay Buffers:

Minimal auto-induction medium consisted of 0.5% glycerol, 0.05% glucose, 0.2% lactose, 50 mM $KH_2PO_4$, 50 mM $Na_2HPO_4$, 10 mM $(NH_4)_2SO_4$, $MgSO_4$, and 1× trace metal solution (Studier, F. W. *Protein production by auto-induction in high-density shaking cultures*. Protein Expression and Purification, 2005, 41, p. 207-234). Autolysis medium consisted of auto-induction medium supplemented with 200 ng/mL anhydro-tetracycline, but no trace metals. Protease assay buffer consisted of 50 mM Tris-HCl, 1 mM DTT and 0.5 mM EDTA, pH 8.0. TVMV substrate solution was composed of protease assay buffer supplemented with 40 μM of the quenched fluorescent peptide substrate for TVMV (Table 1).

Procedure:

Libraries of autoinhibited TVMV mutants were transformed into chemically competent BL21(DE3)-RIL cells hosting the autolysis plasmid 05665 (FIG. 2A) and plated onto LB agar plates supplemented with 100 μg/mL carbenicillin, 50 μg/mL kanamycin and 34 μg/mL chloramphenicol. Following overnight incubation at 37° C., single colonies were inoculated into 96 deep-well plates filled with minimal auto-induction medium (1 mL) which was supplemented with 100 μg/mL carbenicillin, 50 μg/mL kanamycin and 34 μg/mL chloramphenicol. Cells were left to grow for 72 h at 30° C. at 320 rpm and typically reached OD values of approximately 10. To lyse cells, aliquots of cell cultures (100 μL) from half a 96-well-plate (48 samples) were diluted two-fold into autolysis medium (100 μL) and left to incubate for 90 min at 30° C. at 200 rpm. Aliquots of cell lysates (10 μL) were duplicated after transferring them into separate halves of a black 96-well-plate filled with protease assay buffer (140 μL). One of the halves additionally contained 1 U thrombin in order to cleave the linker connecting TVMV to its autoinhibition domain and relieve autoinhibtion. The reaction was initiated following the addition of substrate solution (50 μL) which gave rise to 10 μM TVMV substrate peptide in the final reaction. The reaction was monitored using a fluorometer (Biotek Synergy 4) by measuring the release of a quenched fluorophore (7-Methoxycoumarinyl-4-acetyl) at 405 nm following excitation at 330 nm. The induction of TVMV-based protease activities was evaluated by comparing the time course of the reactions in the presence and absence of thrombin. The plasmids encoding for desirable mutants were subsequently isolated from single colonies and their identity confirmed by Sanger sequencing.

Screening for Protease Biosensors

Bacterial Growth Media and Protease Assay Buffers:

Minimal auto-induction medium consisted of 0.5% glycerol, 0.05% glucose, 0.2% lactose, 50 mM $KH_2PO_4$, 50 mM $Na_2HPO_4$, 10 mM $(NH_4)_2SO_4$, $MgSO_4$, and 1× trace metal solution (Studier, F. W. *Protein production by auto-induction in high-density shaking cultures*. Protein Expression and Purification, 2005, 41, p. 207-234). Autolysis medium consisted of auto-induction medium supplemented with 200 ng/mL anhydro-tetracycline, but no trace metals. Protease assay buffer consisted of 50 mM Tris-HCl, 1 mM DTT and 0.5 mM EDTA, pH 8.0. TVMV substrate solution was composed of protease assay buffer supplemented with 40 μM of the quenched fluorescent peptide substrate for TVMV (Table 1).

Procedure:

Libraries of autoinhibited TVMV mutants were transformed into chemically competent BL21(DE3)-RIL cells hosting the autolysis plasmid 05665 (FIG. 2A) and plated onto LB agar plates supplemented with 100 μg/mL carbenicillin, 50 μg/mL kanamycin and 34 μg/mL chloramphenicol. Following overnight incubation at 37° C., single colonies were inoculated into 96 deep-well plates filled with minimal auto-induction medium (1 mL) which was supplemented with 100 μg/mL carbenicillin, 50 μg/mL kanamycin and 34 μg/mL chloramphenicol. Cells were left to grow for 72 h at 30° C. at 329 rpm and typically reached OD values of approximately 10. To lyse cells, aliquots of cell cultures (100 μL) from half a 96-well-plate (48 samples) were diluted two-fold into autolysis medium (100 μL) and left to incubate for 90 min at 30° C. at 200 rpm. Aliquots of cell lysates (10 μL) were duplicated after transferring them into separate halves of a black 96-well-plate filled with protease assay buffer (140 μL). One of the halves additionally contained 1 U thrombin in order to cleave the linker connecting TVMV to its autoinhibition domain and relieve autoinhibtion. The reaction was initiated following the addition of substrate solution (50 μL) which gave rise to 10 μM TVMV substrate peptide in the final reaction. The reaction was monitored using a fluorometer (Biotek Synergy 4) by measuring the release of a quenched fluorophore (7-Methoxycoumarinyl-4-acetyl) at 405 nm following excitation at 330 nm. The induction of TVMV-based protease activities was evaluated by comparing the time course of the reactions in the presence and absence of thrombin. The plasmids encoding for desirable mutants were subsequently isolated from single colonies and their identity confirmed by Sanger sequencing.

Expression and Purification of Protease Biosensors

Bacterial Growth Media and Buffers:

Terrific Broth (TB) consisted of 1.2% tryptone, 2.4% yeast extract, 0.04% glycerol, 0.17 M $KH_2PO_4$ and 0.72 M $K_2HPO_4$. Phosphate buffered saline (PBS) consisted of 10 mM $Na_2HPO_4$, 2 mM $KH_2PO_4$, 137 mM NaCl and 2.7 mM. Washing and binding buffer consisted of 20 mM $Na_2HPO_4$ and 20 mM imidazole, pH 8.0 which was supplemented with 300 mM NaCl for TVMV-based signal transducers, 500 mM NaCl for HCV-based signal transducers and 1 M NaCl for TVMV-based allosteric receptors based on the affinity clamp. Elution buffer was composed as washing and binding buffer except that it contained 500 mM rather than 20 mM imidazole. Protein storage buffer contained 50 mM Tris-HCl and 10% glycerol, pH 8.0 which was supplemented with 1 mM EDTA and 2 mM DTT for TVMV-based signal transducers, 1 M NaCl, 1 mM EDTA and 2 mM DTT for TVMV-based allosteric receptors and 500 mM NaCl, 2 mM β-mercaptoethanol for HCV-based signal transducers.

Protein Expression:

Plasmids were transformed into chemically competent BL21(DE3)-RIL cells and plated onto LB agar plates supplemented with 100 μg/mL carbenicillin and 34 μg/mL chloramphenicol and incubated overnight at 37° C. A single colony was used to inoculate TB medium (250 mL) supplemented with 0.2% lactose, 0.05% glucose, 2 mM $MgCl_2$, 100 μg/mL carbenicillin and 34 μg/mL chloramphenicol. Cells were grown over the course of 48 h at 30° C. at 200 rpm and the protein expressed by auto-induction with the exception of VHH-domain tagged TVMV-based signal transducer which were expressed for 72 h at 20° C. Cells usually reached OD values of approximately 14 before being harvested by centrifugation at 4,500 g and washed once with PBS (500 mL) and stored at −20° C.

Protein Purification:

To purify the different protease-based signal transducers and allosteric receptors, cells were resuspended in washing and binding buffer and lysed using a one shot cell disruptor (Constant). Samples were subsequently centrifuged at 25,000 g and the supernatant passed through a 0.25 μm filter.

The His$_6$-tagged protein was subsequently purified using an AKTA-FPLC system. Briefly, the lysate was loaded onto Ni-NTA columns (5 mL HisTrap FF Crude, GE Healthcare), the column washed with washing and binding buffer (200 mL) and the protein eluted by running an imidazole gradient from 20 mM to 500 mM over the course of 40 min at a flow rate of 5 mL/min. The protein typically eluted around 100 mM imidazole. Fractions containing protein were subsequently pooled and concentrated using centrifugal filters (Amicon Ultra) with a 10 kDa cut-off before being transferred into protein storage buffer by means of gel filtration using disposable PD-10 desalting columns according to manufacturer's instructions (GE Healthcare). Proteins were generally stored at −80° C.

Protease Activity Assays

Assaying TVMV- and HCV-Based Signal Transducers:

To measure induction ratios under saturating reaction conditions, TVMV- and HCV-based signal transducers (5 μg) were pre-incubated for 10 min in 150 μL protease assay buffer (50 mM Tris-HCl, 1 mM DTT and 0.5 mM EDTA, pH 8.0 for TVMV, and 50 mM Tris-HCl, 50 mM NaCl and 1 mM DTT, pH 8.0 for HCV) in the presence and absence of the inducing protease: i.e. 1 U thrombin, 1 U Factor Xa, 5 μg PSA, 1 μg MMP-7 and 1 μg for MMP-9 for TVMV-based signal transducers as indicated, and 5 μg TVMV for HCV-based signal transducers. The reaction was initiated following the addition of 50 μL substrate solution that contained 40 μM peptide substrate and gave rise to 10 μM peptide substrate in a final reaction volume of 200 μL. The reaction was monitored using a fluorometer (Biotek Synergy 4) by measuring the release of 7-Methoxycoumarinyl-4-acetyl from the quenched substrate peptide at 405 nm following excitation at 330 nm. The induction ratio of TVMV-based protease activities in the inhibited and uninhibited state was evaluated by comparing the reaction in the presence and absence of the activating protease. Activity traces labelled as 'Background' generally denote control samples that contain peptide substrate, but no enzyme.

Assaying the Effects of Direct and Indirect Affinity Targeting:

The effect of direct affinity targeting through PSA-specific VHH-domains was evaluated with PSA-inducible TVMV-based signal transducer (500 nM) that have been suitably tagged with PSA-specific VHH domains in either N- or C-terminal orientations in protease reaction buffer consisting of 50 mM Tris-HCl, 0.5 mM EDTA and 1 mM DTT, pH 8.0. The reaction was strictly initiated following the simultaneous addition of TVMV substrate peptide (Table 1) to a final concentration of 10 μM and varying concentrations of catalytically active PSA to a final concentration of 1.6-200 ng/mL as indicated in FIG. 8B.

The effect of direct affinity targeting through SH3-domain:SH3-peptide interactions was measured with suitably tagged thrombin-inducible TVMV-based signal transducers (10 nM) and TVMV-inducible HCV-based signal transducers (200 nM) in the presence or absence of thrombin (1 U per 200 μL) in 50 mM Tris-HCl, 200 mM NaCl, 0.5 mM EDTA and 1 mM DTT, pH 8.0. The reaction was strictly initiated following the simultaneous addition of the HCV-based signal transducer and TVMV substrate peptide (Table 1) to a final concentration of 10 μM.

The effect of indirect affinity targeting through IgG and ZZ-domain fusions was evaluated with TVMV-AI-ZZ (300 nM) or TVMV-AI (300 nM) in the presence or absence of a human thrombin specific IgG (150 nM, 5020 Thermoscientific, Catalogue #MAI-43019) and varying concentrations of human thrombin (between 1-15 mU per 200 μL) in 50 mM Tris-HCl and 0.5 mM EDTA, pH 8.0. The reaction was strictly initiated following the simultaneous addition of TVMV peptide substrate (Table 1) and thrombin.

Assaying TVMV-Based Allosteric Receptors:

The maximum induction ratio of TVMV-based allosteric receptors (500 nM) was measured in a similar fashion in the presence or absence of the PDZ ligand peptide-1 (RGSIDTWV) at a final concentration of 10 μM in protease assay buffer consisting of 50 mM Tris-HCl, 1 M NaCl, 1 mM DTT and 0.5 mM EDTA, pH 8.0. The reaction was generally initiated following the addition of TVMV substrate peptide (Table 1) to a final concentration of 10 μM.

Protease Signalling Cascades:

Signalling cascades consisting of SH3-domain-tagged TVMV-based allosteric receptors (10 nM) and SH3-peptide-tagged TVMV-inducible HCV-based signal transducers (200 nM) were measured in protease assay buffer consisting of 50 mM Tris-HCl, 200 mM NaCl and 1 mM DTT, pH 8.0. The reaction was strictly initiated by simultaneously adding the TVMV-based allosteric receptor and HCV substrate peptide to a final concentration of 10 μM along with the PDZ ligand peptide-1 (RGSIDTWV) at a final concentration of 10 μM. To determine the $K_D$ of TVMV-based allosteric receptors, the PDZ ligand peptide-1 (RGSIDTWV) was suitably diluted over a concentration range from 2 nM to 400 nM as indicated in FIG. 13B. To determine the $K_D$, initial rates were plotted against ligand concentrations and the fitted values analysed by non-linear regression assuming a one-site specific binding model (GraphPad Prism 5).

Enzyme Kinetics of TVMV-Based Signal Transducers:

The kinetics of different protease biosensors in their autoinhibited and activated states were measured in protease assay buffer over different substrate concentrations ranging from 1 μM to 80 μM. The enzyme was included at either 5 μg or 1 μg per 100 μL reaction depending whether the autoinhibited and activated state were assayed, respectively. Measurements were performed in duplicates for each concentration. Initial rates were plotted against substrate concentration and kinetic parameters obtained by a non-linear regression curve fit assuming Michaelis-Menten kinetics (GraphPad Prism 5).

Choosing a Protease to Create Artificially Inhibited Proteases

General Considerations

Proteases with substrate specificities of more than X amino acids that are sufficiently specific not to cross-react or interfere with proteins (i.e. neither cleave nor bind) in a particular biological sample that is being analyzed.

Proteases can be derived from natural repertoires, especially from pathogens including viruses and bacteria that are interacting with a high degree of specificity with their host organism: e.g. during invasion, maturation etc.

Substrate sequences that serve as starting points for generating autoinhibition domains can be readily identified from autoproteolytic processing sites and cleavage sites in host proteins.

In some cases, specific protein based binders based on artificial, protein based binding scaffolds have been generated.

Alternatively, proteases can be artificially engineered for better substrate specificity.

Examples of Highly Specific Proteases from Natural Repertoires

Proteases that are derived from viral genomes that are dependent on expression and proteolytic processing of a polyprotein and other events required as part of the viral life cycle: e.g. Picornavirales, Nidovirales, Herpesvirales, Retroviruses and Adenoviruses etc Specifically, within the family of Potyviridae the NIa protease of TEV, TVMV, SMV etc Specifically, within the family of Picornaviridae the 3C protease of EV71, Norovirus etc Specifically, within the family of Picornaviridae the 2A protease of human rhinovirus, coxsackievirus B4 etc Specifically, within the family of Picornaviridae the leader protease of FMDV etc Specifically, within the family of Coronaviridae the 3C-like protease of SARS-CoV, such as IBV-CoV etc Specifically, within the family of Herpesviridiae HSV-1, HSV-2, HCMV and MCMV proteases etc.

Defining Common Feature of Viral Proteinases which May be Relevant

Viral proteases predominantly include cysteine proteases while serine proteases are rare.

Metallo- and other types of proteases are not typical in viral proteomes. NIa, 3C, 3C-like and 2A proteases are considered chymotrypsin-like cysteine proteases.

Leader protease of FMDV is considered a papain-like cysteine protease.

HCMV, MCMV, HSV-1, HSV-2 etc are serine proteases with a common, but unique fold.

NS3 proteases HCV, WNV and DVV are serine proteases with a common fold.

Adenovirus protease is cysteine protease with a unique fold which so far could not be identified in other viruses.
Other proteases of interest include:
- Botulinum neurotoxin (i.e. BoNT/A and BoNT B protease) specifically cleaves SNARE proteins. Camelid based binders that may be used for construction of the autoinhibition domain are readily available.
- Proteases of bacterial species that invade cells and interact in highly specific manners.

Some examples of well characterized candidate viral proteases are shown in Tables 2-8.

TABLE 2

| Leader Protease | Structures | Distance | Expression | Comments |
|---|---|---|---|---|
| FMDV | Many solved (e.g. 1QOL) | C-terminus observed in the active site of neighbouring molecules | Soluble in E. coli at 15° C.; Untagged | |

TABLE 3

| 3C Proteases | Structures | Distance | Expression | Comments |
|---|---|---|---|---|
| EV71 | 3OSY, 3SJK, 3SJO | N-Protease to C-Substrate < 22 A Favourable | Soluble in E. coli at 18° C.; His-tag sufficient | Fluorogenic substrate assay available |
| Norovirus | 2IPH, 1WQS | N-Protease to C-Substrate < 22 A Favourable | Soluble in E. coli at 37° C.; His-tag sufficient | Fluorogenic substrate assay available |
| HRV2 | 2XYA, 1CQQ | N-Protease to C-Substrate < 22 A Favourable | | |

TABLE 4

| 2A Proteases | Structures | Distance | Expression | Comments |
|---|---|---|---|---|
| HRV2 | 2HRV | N-Protease to C-Substrate < 17 A Very Favourable | Soluble in E. coli at 34° C. | |
| CVB4 | 1Z8R | N-Protease to C-Substrate < 17 A Very Favourable | Soluble in E. coli at 25° C. | Susceptible to cold denaturation |

TABLE 5

| 3C-like Proteases | Structures | Distance | Expression | Comments |
|---|---|---|---|---|
| SARS-CoV | Many Solved (e.g. 2Q6G, 1UJI) | N-Protease to C-Substrate ~42 A Unfavourable | Soluble in E. coli with GST-tag; Concentrate to 10 mg/mL for crystalisation | Possibly truncate around 190 unless expression of the C-terminal domain is important for folding? |
| IBV-CoV | Many Solved (e.g. 2Q6F) | Similar to SARS-CoV | | |

TABLE 6

| Considered New | Structures | Distance | Expression | Comments |
|---|---|---|---|---|
| HCMV | Many solved (e.g. 1CMV, 1NKM) | Generally unfavourable, but maybe possible across dimers | Soluble in E. coli | Susceptible to autocalytic inactivation which can be improved by engineering. |
| HSV-2 | 1AT3 | Generally unfavourable, but maybe possible across dimers | Soluble in E. coli | Expression includes autocatalytic maturation. |

TABLE 7

| NS3/Serine Protease | Structures | Distance | Expression | Comments |
|---|---|---|---|---|
| West Nile Fever | 2FP7 | Very favourable | Generally soluble in E. coli, | |
| Dengue Virus 2 | 2FOM | | | |
| Yellow Fever | | | | |
| Hepatitis C Virus | Many Solved (e.g. 1DXW, 3P8N, 2A4Q) | Very favourable | Generally soluble in E. coli, but very sensitive to oxidizing conditions | Different protein based inhibitors are available: e.g. minibodies, camelised VH domain, eglin c etc |

TABLE 8

| Other/Unique | Structures | Distance | Expression | Comments |
|---|---|---|---|---|
| Adenovirus | 1NLN | Unfavourable | 5-20% soluble in E. coli, but protocols mainly depend on inclusion body purification | |

Rationale of Autoinhibiting Potyvirus NIA Proteases

Description of Basic Elements

The native function of NIa proteases from Potyviridae is to process the viral polyprotein proteome. A schematic representation of the viral polyprotein proteome is shown in FIG. 2C.

Peptides that bind the active site of NIa proteases and inhibit their activity are generally derived from Site F which refers to a peptide sequence which separates the NIb RNA polymerase from the viral coat protein, and is considered the most efficient substrate for NIa proteases.

Substrate Sequences of Site F for three different NIa proteases derived from TVMV, TEV and SMV:

|  | P7 | P6 | P5 | P4 | P3 | P2 | P1 | P1' | P10 | P2' | P3' |  |
|---|---|---|---|---|---|---|---|---|---|---|---|---|
| TVMV |  |  |  | R | E | T | V | R | F | Q | S | D | T | (SEQ ID NO: 68) |
| TEV |  |  | T | E | N | L | Y | F | Q | S | G | T | (SEQ ID NO: 69) |
| SMV |  | N | E | D | V | F | H | Q | S | G | S | (SEQ ID NO: 70) |

Engineering Autoinhibited NIa Proteases

Create an autoinhibited NIa protease by appending up to seven amino acids of the N-terminal cleavage product derived from Site F to the C-terminus of the NIa protease. In this way, an autoinhibition domain (AI-domain) is created which efficiently competes with the NIa protease substrate due to its high effective concentration at the C-terminus of the NIa protease (c.f. production inhibition).

Figure 3:
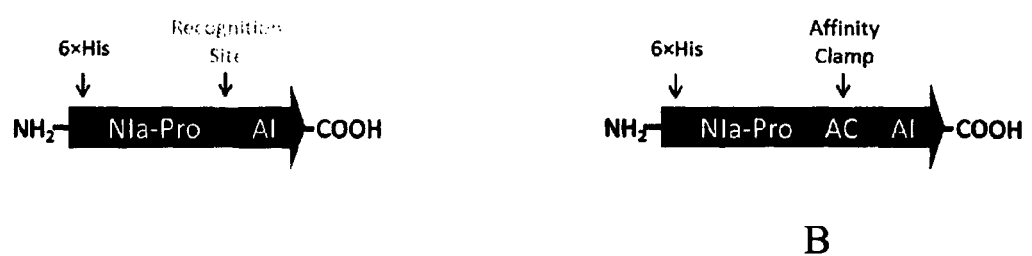
FIG. 3: Schematic depiction of a biosensor comprising (A) a target protease cleavage (recognition) site in the sensor amino acid sequence; and (B) an affinity clamp in the sensor amino acid sequence.

To create a protease-activated biosensor, a recognition site for a target protease can be inserted between the NIa protease and the AI-domain. Autoinhibition is relieved as the target protease cleaves the recognition site and separates the AI-domain from the NIa protease. A schematic representation of such a biosensor construct is shown in FIG. 3A.

To create an allosteric biosensor, a protein based binder known to undergo conformational changes upon ligand binding (e.g. an affinity clamp) can be inserted between the NIa protease and the AI-domain. Autoinhibition is induced upon ligand binding as the affinity clamp contracts bringing the NIa protease into closer proximity with its AI-domain. A schematic representation of such a biosensor construct is shown in FIG. 3B.

Problem: Since the AI-domain is located at the very C-terminus, efficient autoinhibition depends on accurately translated, full-length protein. In practice however, premature termination of translation leads to a significant fraction of proteases which lack an AI-domain. This results in a significant fraction of constitutively active proteases in any given protein preparation and unacceptable levels of background activity (up to 10% limiting overall induction ratios to approximately 10-fold).

Solution: Create AI-domains which can either be fused to the N-terminus of a NIa protease (FIG. 4A, C) which prevent the formation of constitutively active proteases lacking an AI-domain as a result of premature termination of translation, or allow an affinity purification tag to be placed at the C-terminus of the AI-domain (FIG. 4B,D) which enables the purification of full-length protein. Both types of solutions require an AI-domain which can efficiently bind the active site, but is not cleaved. Alternatively, the NIa protease can be circularly permutated and the inhibitor sequence used to fuse the original N- and C-termini while creating a new set of termini elsewhere. In this configuration the partially translated sequences will be inactive (see the detailed description below).

Engineering Non-Cleavable AI-Domains

Substrate mapping data for TEV suggests that proline in the P1' position prevents cleavage (Kapust, R. B., J. Tozser, T. D. Copeland, and D. S. Waugh. "*The P1' Specificity of Tobacco Etch Virus Protease.*" Biochem Biophys Res Commun 294, no. 5 (2002): 949-55). It is however unclear whether sequences with a proline in the P1' position cannot bind or bind, but cannot be cleaved by TEV protease, and to what extents this holds true for other members of the NIa potyvirus protease family including TVMV.

Screening a library of 20 amino acids in the P1 position and proline in the P1' position, we identified di-peptide motifs covering the P1-P1' junction that bind the active site of TVMV, but are not cleaved. Binding affinity measured indirectly through the ability to autoinhibit is sequence dependent: AP>GP>PP>QP.

|  | P7 | P6 | P5 | P4 | P3 | P2 | P1 | P1' | P2' | P3' |  |
|---|---|---|---|---|---|---|---|---|---|---|---|
| TVMV-WT |  |  | R | E | T | V | R | F | Q | S | D | T | (SEQ ID NO: 71) |
| AI-1 |  |  | R | E | T | V | R | F | <u>A</u> | <u>P</u> | G | S | (SEQ ID NO: 72) |
| AI-2 |  |  | R | E | T | V | R | F | <u>G</u> | <u>P</u> | G | S | (SEQ ID NO: 73) |
| AI-3 |  |  | R | E | T | V | R | F | <u>P</u> | <u>P</u> | G | S | (SEQ ID NO: 74) |
| AI-4 |  |  | R | E | T | V | R | F | <u>Q</u> | <u>P</u> | G | S | (SEQ ID NO: 75) |

Alternatively, non-cleavable active site binders may already be known as in case of the serine NS3 protease from Hepatitis C-virus (HCV) for which the cysteine-proline di-peptide motif constitutes one such non-cleavable binding peptide which is capable of bridging the P1-P1' junction without being cleaved by the NS3 protease of HCV. As part of the peptide DELIL<u>CP</u>LDL (SEQ ID NO:58), a non-cleavable AI-domain can be engineered which binds and blocks the active site of the NS3 protease of HCV.

Optimizing Autoinhibition

To improve binding of the AI-domain to the NIa protease, and thus achieve better autoinhibition, additional affinity features can be introduced by mutating the AI-domain and/or the NIa protease to form a more tightly inhibited AI-domain-NIa-protease complex.

P8, P7 and P5 are particularly amenable to mutation which according to kinetic, structural and substrate mapping data do not significantly contribute to substrate recognition by NIa proteases (unlike P6, P4, P3, P2 and P1).

Complementing mutations may also be introduced into the NIa protease to enhance interactions with P8, P7 and P5—e.g. in case of TVMV, by optimizing electrostatic interactions between P8 and P7 and loop M134-F139 or by introducing additional hydrophobic contacts between P5 and the beta-sheet formed by F213-V216 interactions.

Binding of the AI-domain can also be improved by simultaneously constraining the N- and the C-terminal ends of the AI-domain. This creates fixed anchor points in space limiting diffusion of the AI-domain while also reducing backbone flexibility of the AI-domain. In combination, this enhances the affinity of the AI-domain to the protease biosensor by reducing the loss in entropy upon binding. Constraints can be created in several ways: (a) Additional affinity features located outside of the AI-domain can be introduced artificially: e.g. dimerization motives based on coiled-coils (e.g. see Thompson, K. E., C. J. Bashor, W. A. Lim, and A. E. Keating. "*Synzip Protein Interaction Toolbox: In Vitro and in Vivo Specifications of Heterospecific Coiled-Coil Interaction Domains*." ACS Synth Biol 1, 118-129) located at the N- and C-terminus of the protease biosensor can constrain one of the free ends of the peptide motif. (b) The topology of the NIa protease can be rearranged by circular permutation so that the AI-domain is relocated internally while a set of new N- and C-termini is created. (c) The protease can be fused N- or C-terminally to an established protein scaffold (including but not limited to the tenth domain of fibronectin, thioredoxin or the camelid VHH domain) or a peptide that target the biosensor to a particular enzyme, cellular organelle or an organ. These scaffolds can be engineered for features that promote binding to the active site resulting in inhibition of protease activity. To this end, a range of established protein engineering strategies are available including rational protein design, combinatorial library screening or by means of directed evolution. The creation of active site directed protein binders can be facilitated when the AI-domain is grafted into the loop region of the above protein scaffold in this way providing one binding feature which blocks the active site.

Binding of the AI-domain can also be improved by improving the linker region connecting the AI-domain to the NIa protease—e.g. by truncating the C-terminus of TVMV and increasing the effective concentration of the AI-domain near the active site.

Summary of Thrombin Specific Biosensors Based on Autoinhibited TVMV

All thrombin specific biosensors have been identified in limited, semi-rational screens while selecting for high-induction ratios in the presence and absence of thrombin.

Figure 4:
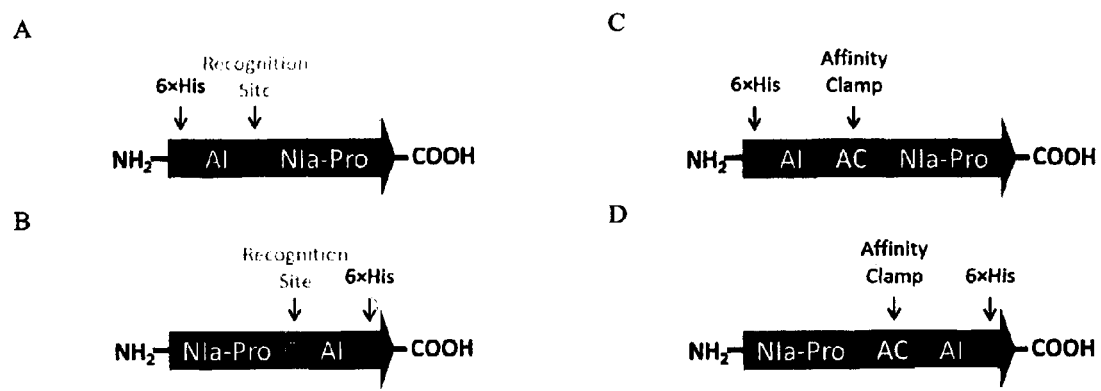
FIG. 4: Schematic depiction of a biosensor comprising (A) a target protease cleavage (recognition) site in the sensor amino acid sequence and an N-terminal His tag; (B) a target protease cleavage (recognition) site in the sensor amino acid sequence and a C-terminal His tag; (C) an affinity clamp in the sensor amino acid sequence with an N-terminal His tag; and (D) an affinity clamp in the sensor amino acid sequence with a C-terminal His tag.

The biosensors generally feature an uncleavable AI-domain along with a C-terminal His-purification tag which allows for homogenous preparations of full-length, autoinhibited TVMV protease mutants (see FIG. 4B).

In addition, individual clones include the following key features summarized in Table 8:

Clone H6 (unmodified TVMV).

Clone 2B4 (electrostatic interactions between P8, P7 and loop M134-F139).

Clone 68 (hydrophobic interactions between P5 and the beta-sheet formed by 213-V216+electrostatic interactions between P8, P7 and loop M134-F139).

Clone H6-68 is a combination of H6 and 68 (hydrophobic interactions between P5 and the beta-sheet formed by 213-V216).

Clone H6-143 is a combination of clone H6 and 143 (hydrophobic interactions between P5 and the beta-sheet formed by 213-V216).

The biosensor (1 µM) was incubated together with 10 µM protease substrate in 50 mM Tris-HCl, 1 mM DTT and 0.5 mM EDTA. Relief of autoinhibition was achieved upon addition of bovine thrombin (1 U per 200 µL).

TABLE 8

| Mutant ID | TVMV C-Term, Pos 210+ | Thrombin-Linker | AI-Domain | Additional Mutations | Fold Induction |
|---|---|---|---|---|---|
| H6-AP | ...WGSFTLVEDAPE DDFM (SEQ ID NO: 76) | SGLVPRGV (SEQ ID NO: 77) | GRETVRF<u>AP</u>GSTHHH HHH* (SEQ ID NO: 78) | | ~50 |
| 2B4-GP | ...WGSFTLVEDAP (SEQ ID NO: 79) | SGLVPRGV SG (SEQ ID NO: 80) | EGETVRF<u>GP</u>GSTHHH HHH* (SEQ ID NO: 81) | M134K, E135R | ~17 |
| 2B4-AP | ...WGSFTLVEDAP (SEQ ID NO: 79) | SGLVPRGV SG (SEQ ID NO: 80) | EGETVRF<u>AP</u>GSTHHH HHH* (SEQ ID NO: 82) | M134K, E135R | ~25 |
| 68-GP | ...WGSFILWED (SEQ ID NO: 83) | SGLVPRGV SG (SEQ ID NO: 80) | EGEYVRF<u>GP</u>GSTHHH HHH* (SEQ ID NO: 81) | M134K, E135K | ~60 |
| 68-AP | ...WGSFILWED (SEQ ID NO: 83) | SGLVPRGV SG (SEQ ID NO: 80) | EGEYVRF<u>AP</u>GSTHHH HHH* (SEQ ID NO: 82) | M134K, E135K | ~100 |

TABLE 8-continued

| Mutant ID | TVMV C-Term, Pos 210+ | Thrombin-Linker | AI-Domain | Additional Mutations | Fold Induction |
|---|---|---|---|---|---|
| H6-143 | ...WGSFYLYEDAPE DDFM (SEQ ID NO: 76) | SGLVPRGV (SEQ ID NO: 77) | GRETYRFAPGSTHHH HHH* (SEQ ID NO: 78) | | ~60 |
| H6-68 | ...WGSFILWEDAPE DDFM (SEQ ID NO: 76) | SGLVPRGV (SEQ ID NO: 77) | GRETYRFAPGSTHHH HHH* (SEQ ID NO: 78) | | ~150-200 |

The complete amino acid sequences of the protein constructs summarized in Table 8 are as follows.

The protease amino acid sequence is underlined, the amino acid sequence of the protease cleavage site is bolded and the amino acid sequence of the autoinhibitor peptide is double-underlined. The His tag is at the C-terminus. Linker sequences are in plain font.

H6-AP:

(SEQ ID NO: 1)
SSGSKALLKGVRDFNPISACVCLLENSSDGHSERLFGIGFGPYIIANQHL

FRRNNGELTIKTMHGEFKVKNSTQLQMKPVEGRDIIVIKMAKDFPPFPQK

LKFRQPTIKDRVCMVSTNFQQKSVSSLvsesshivhkedtsfwqhwittk dgqcgsplvsiidgnilgihslthttngsnyfvefpekfvatyldaadgw cknwkfnadkiswqsftlvedapedfmsglvprgvgretvrfapgsthhh hhh.

The encoding nucleotide sequence is:

(SEQ ID NO: 29)
Tctagtggttctaaagetttgctgaagggcgtgcgcgattttaatccgat ctctgcttgcgtatgcctgctggaaaactcctcggatggtcatagtgaac gtctgtttggcattggttttggcccgtatatcattgccaaccagcatctg tttcgtcgtaacaatggcgaactgaccatcaaaaccatgcatggtgaatt caaagtcaaaaactctacccagctgcagatgaaaccggttgaaggccgtg acattatcgttatcaaaatggctaaagacttcccgccgttcccgcagaaa ctgaaattccgtcagccgaccatcaaagatcgtgtgtgcatggtgtccac caactttcagcagaaaagcgtctcgagcctggtgtctgaatcctctcaca ttgtgcataaagaagacacttcttctggcagcactggatcaccactaaa gatggccagtgtggcagccactagtttccatcattgatggcaacattct gggcatccacagcctgactcataccaccaacggtagcaactacttcgtgg aatttccggaaaaattcgtggcgacttatctagatgccgcggatggttgg tgcaaaaactggaaattcaacgcggataaaatcagctggggttcctttac cctggttgaagatgcgccgaagacttcatgagtggtctggtgccgcgcg gtgtaggtcgcgaaaccgtgcgctttgccccgggaagcacccaccaccat catcatcac

2B4-GP:

(SEQ ID NO: 2)
Ssgskallkgvrdfnpisacvcllenssdghserlfgigfgpyiianqhl frrnngeltiktmhgefkvknstqlqmkpvegrdiivikmakdfppfpqk -continued lkfrqptikdrvcmvstnfqqksvsslvsesshivhmrdtsfwqhwittk dgqcagplvsiidgnilgihslthttngsnyfvefpekfvatyldaadgw cknwkfnadkiswqsftlvedapsglvprgvsgegetvrfgpgsthhh hhh The encoding nucleotide sequence is:

(SEQ ID NO: 30)
Tctagtggttctaaagctttgctgaagggcgtgcgcgattttaatccgat ctctgcttgcgtatgcctgctggaaaactcctcggatggtcatagtgaac gtctgtttggcattggttttggcccgtatatcattgccaaccagcatctg tttcgtcgtaacaatggcgaactgaccatcaaaaccatgcatggtgaatt caaagtcaaaaactctacccagctgcagatgaaaccggttgaaggccgtg acattatcgttatcaaaatggctaaagacttcccgccgttcccgcagaaa ctgaaattccgtcagccgaccatcaaagatcgtgtgtgcatggtgtccac caactttcagcagaaaagcgtctcgagcctggtgtctgaatcctctcaca ttgtgcatatgagagatacttctttctggcagcactggatcaccactaaa gatggccagtgtggcagccactagtttccatcattgatggcaacattct gggcatccacagcctgactcataccaccaacggtagcaactacttcgtgg aatttccggaaaaattcgtggcgacttatctagatgccgcggatggttgg tgcaaaaactggaaattcaacgcggataaaatcagctggggttcctttac cctggttgaagatgcgccgagtggtctggtgccgcgcggtaagtggtg aaggtgaaaccgtgcgctttggcccgggaagcacccaccaccatcatcat cac

2B4-AP:

(SEQ ID NO: 3)
Ssgskallkgvrdfnpisacvcllenssdghserlfgigfgpyiianqhl frrnngeltiktmhgefkvknstqlqmkpvegrdiivikmakdfppfpqk lkfrqptikdrvcmvstnfqqksvsslvsesshivhmrdtsfwqhwittk dgqcgsplvsiidgnilgihslthttngsnyfvefpekfvatyldaadgw cknwkfnadkiswqsftlvedapsglvprgvsgegetvrfapgsthhh hhh The encoding nucleotide sequence is:

(SEQ ID NO: 31)
Tctagtggttctaaagctttgctgaagggcgtgcgcgattttaatccgat ctctgcttgcgtatgcctgctggaaaactcctcggatggtcatagtgaac -continued

```
gtctgtttggcattggttttggcccgtatatcattgccaaccagcatctg
tttcgtcgtaacaatggcgaactgaccatcaaaaccatgcatggtgaatt
caaagtcaaaaactctacccagctgcagatgaaaccggttgaaggccgtg
acattatcgttatcaaaatggctaaagactycccgccgttccgcagaaa
ctgaaattccgtcagccgaccatcaaagatcgtgtgtgcatggtgtccac
caactttcagcagaaagcgtctcgagcctggtgtctgaatcctctcaca
ttgtgcatatgagagatacttctttctggcagcactggatcaccactaaa
gatggccagtgtggcagcccactagtttccatcattgatggcaacattct
gggcatccacagcctgactcataccaccaacggtagcaactacttcgtgg
aatttccggaaaaattcgtggcgacttatctagatgccgcggatggttgg
tgcaaaaactggaaattcaacgcggataaaatcagctggggttcctttac
cctggttgaagatgcgccgagtggtctggtgccgcgcggtgtaagtggtg
aaggtgaaaccgtgcgctttgccccgggaagcacccaccaccatcatcat
cac
```

68-GP:

(SEQ ID NO: 4)
<u>Ssgskallkgvrdfnpisacvcllenssdghserlfgigfgpyiianqhl</u>
<u>frrnnngeltiktmhgefkvknstqlqmkpvegrdiivikmakdfppfpqk</u>
<u>lkfrqptikdrvcmvstnfqqksvsslvsesshivhmrdtsfwqhwittk</u>
<u>dgqcgsplvsiidqnilgihslthttngsnyfvefpekfvatyldaadqw</u>
<u>cknwkfnadkiswqsfilweds</u>glvprgvsg<u>eqeyvrfqp</u>gsthhhhhh The encoding nucleotide sequence is:

(SEQ ID NO: 32)
```
Tctagtggttctaaagctttgctgaagggcgtgcgcgattttaatccgat
ctctgcttgcgtatgcctgctggaaaactcctcggatggtcatagtgaac
gtctgtttggcattggttttggcccgtatatcattgccaaccagcatctg
tttcgtcgtaacaatggcgaactgaccatcaaaaccatgcatggtgaatt
caaagtcaaaaactctacccagctgcagatgaaaccggttgaaggccgtg
acattatcgttatcaaaatggctaaagactcccgccgttccgcagaaa
ctgaaattccgtcagccgaccatcaaagatcgtgtgtgcatggtgtccac
caactttcagcagaaagcgtctcgagcctggtgtctgaatcctctcaca
ttgtgcatatgagagatacttctttctggcagcactggatcaccactaaa
gatggccagtgtggcagcccactagtttccatcattgatggcaacattct
gggcatccacagcctgactcataccaccaacggtagcaactacttcgtgg
aatttccggaaaaattcgtggcgacttatctagatgccgcggatggttgg
tgcaaaaactggaaattcaacgcggataaaatcagctggggatcgtttat
cctgtgggaagatagtggtctggtgccgcgcggtgtaagtggtgaaggtg
aaatatgtgcgctttgccccgggaagcacccaccaccatcatcatcac
```

68-AP:

(SEQ ID NO: 5)
<u>Ssgskallkgvrdfnpisacvcllenssdghserlfgigfgpviianqhl</u>
<u>frrnnngeltiktmhgefkvknstqlqmkpvegrdiivikmakdfppfpq</u>
<u>klkfrqptikdrvcmvstnfqqksvsslvsesshivhmrdtsfwqhwitt</u>
<u>kdgqcgsplvsiidqnilgihslthttngsnyfvefpekfvatyldaadq</u>
<u>wcknwkfnadkiswqsfilweds</u>glvprgvsg<u>eqeyvrfap</u>gsthhhhhh The encoding nucleotide sequence is:

(SEQ ID NO: 33)
```
tctagtggttctaaagcttgctgaagggcgtgcgcgattttaatccgatc
tctgcttgcgtatgcctgctggaaaactcctcggatggtcatagtgaacg
tctgtttggcattggttttggcccgtatatcattgccaaccagcatctgt
ttcgtcgtaacaatggcgaactgaccatcaaaaccatgcatggtgaattc
aaagtcaaaaactctacccagctgcagatgaaaccggttgaaggccgtga
cattatcgttatcaaaatggctaaagactcccgccgttccgcagaaac
tgaaattccgtcagccgaccatcaaagatcgtgtgtgcatggtgtccacc
aactttcagcagaaagcgtctcgagcctggtgtctgaatcctctcacat
tgtgcatatgagagatacttctttctggcagcactggatcaccactaaag
atggccagtgtggcagcccactagtttccatcattgatggcaacattctg
ggcatccacagcctgactcataccaccaacggtagcaactacttcgtgga
atttccggaaaaattcgtggcgacttatctagatgccgcggatggttggt
gcaaaaactggaaattcaacgcggataaaatcagctggggatcgtttatc
ctgtgggaagatagtggtctggtgccgcgcggtgtaagtggtgaaggtga
atatgtgcgctttgccccgggaagcacccaccaccatcatcatcac
```

H6-143-AP:

(SEQ ID NO: 6)
<u>SSGSKALLKGVRDFNPISACVCLLENSSDGHSERLFGIGFGPYIIANQHL</u>
<u>FRRNNGELTIKTMHGEFKVKNSTQLQMKPVEGRDIIVIKMAKDFPPFPQK</u>
<u>LKFRQPTIKDRVCMVSTNFQQKSVSSLvsesshivhkedtsfwqhwittk</u>
<u>dgqcgsplvsiidqnilgihslthttngsnyfyefpekfvatyldaadqw</u>
<u>cknwkfnadkiswqsfylyedapedfms</u>glvprgvg<u>reyvrfap</u>gsthhh
hhh The encoding nucleotide sequence is:

(SEQ ID NO: 34)
```
tctagtggttctaaagctttgctgaagggcgtgcgcgattttaatccgat
ctctgcttgcgtatgcctgctggaaaactcctcggatggtcatagtgaac
gtctgtttggcattggttttggcccgtatatcattgccaaccagcatctg
tttcgtcgtaacaatggcgaactgaccatcaaaaccatgcatggtgaatt
caaagtcaaaaactctacccagctgcagatgaaaccggttgaaggccgtg
acattatcgttatcaaaatggctaaagactycccgccgttccgcagaaa
ctgaaattccgtcagccgaccatcaaagatcgtgtgtgcatggtgtccac
caactttcagcagaaagcgtctcgagcctggtgtctgaatcctctcaca
ttgtgcataaagaagacttctttctggcagcactggatcaccactaaa
gatggccagtgtggcagcccactagtttccatcattgatggcaacattct
gggcatccacagcctgactcataccaccaacggtagcaactacttcgtgg
```

-continued aatttccggaaaaattcgtggcgacttatctagatgccgcggatggttgg tgcaaaaactggaaattcaacgcggataaaatcagctggggttccttta tctgtatgaagatgcgccggaagacttcatgagtggtctggtgccgcgcg gtgtaggtcgcgaatatgtgcgctttgccccgggaagcacccaccaccat catcatcac

H6-68-AP:
(SEQ ID NO: 7)
SSGSKALLKGVRDFNPISACVCLLENSSDGHSERLFGIGFGPYIIANQHL

FRRNNGELTIKTMHGEFKVKNSTQLQMKPVEGRDIIVIKMAKDFPPFPQK

LKFRQPTIKDRVCMVSTNFQQKSVSSLvsesshivhkedtsfwqhwittk dqqcqsplvsiidgnilgihslthttngsnyfyefpekfvatyldaadqw cknwkfnadkiswqsfilwedapedfmsglvprgvgreyvrfapgsthhh hhh The encoding nucleotide sequence is:

(SEQ ID NO: 35)
tctagtggttctaaagctttgctgaagggcgtgcgcgattttaatccgat ctctgcttgcgtatgcctgctggaaaactcctcggatggtcatagtgaac gtctgtttggcattggttttggcccgtatatcattgccaaccagcatctg tttcgtcgtaacaatggcgaactgaccatcaaaaccatgcatggtgaatt caaagtcaaaaactctaccagctgcagatgaaaccggttgaaggccgtg acattatcgttatcaaaatggctaaagacttcccgccgttcccgcagaaa ctgaaattccgtcagccgaccatcaaagatcgtgtgtgcatggtgtccac caactttcagcagaaagcgtctcgagcctggtgtctgaatcctctcaca ttgtgcataaagaagacacttctttctggcagcactggatcaccactaaa gatggccagtgtggcagcccactagtttccatcattgatggcaacattct gggcatccacagcctgactcataccaccaacggtagcaactacttcgtgg aatttccggaaaaattcgtggcgacttatctagatgccgcggatggttgg tgcaaaaactggaaattcaacgcggataaaatcagctggggttcctttat cctgtgggaagatgcgccggaagacttcatgagtggtctggtgccgcgcg gtgtaggtcgcgaatatgtgcgctttgccccgggaagcacccaccaccat catcatcac

Summary of Creating Factor XA, MMP-7, MMP-9, TEV and PSA-Specific Biosensors Based on Autoinhibited TVMV To illustrate the general applicability of the biosensor design, we readily reconfigured the originally developed thrombin biosensor towards new cleavage specificities to detect target proteases other than thrombin. Taking advantage of the modular design, we constructed a panel of biosensor proteases based on the thrombin inducible mutant H6-68-AP. To this end, the cleavage site for thrombin in the thrombin-inducible biosensor was replaced with the cleavage sites for Factor Xa, MMP-7, MMP-9 and PSA. Cleavage sites were either based on naturally occurring cleavage sites of the target protease as in case of Factor Xa and MMP-7. In case of MMP-9, an artificial cleavage site that has been optimized for improved reactivity by means of substrate phage displays was employed. In case of PSA, both natural and phage display optimized cleavage sites have been employed.

Figure 6:
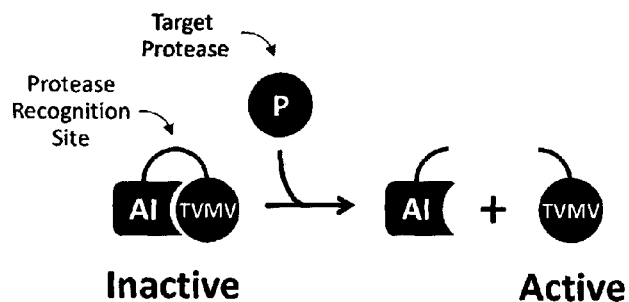
FIG. 6: Summary of elementary biosensor data. To illustrate the general applicability of the biosensor platform, a panel of TVMV-based biosensors were generated simply by exchanging the cleavage sites connecting the AI-domain to the protease biosensor for different target proteases. Both naturally occurring (e.g. Thrombin, Factor Xa and MMP-7 and PSA) and artificially-engineered cleavage sites were tested (e.g. MMP-9 and PSA).
Figure 6:
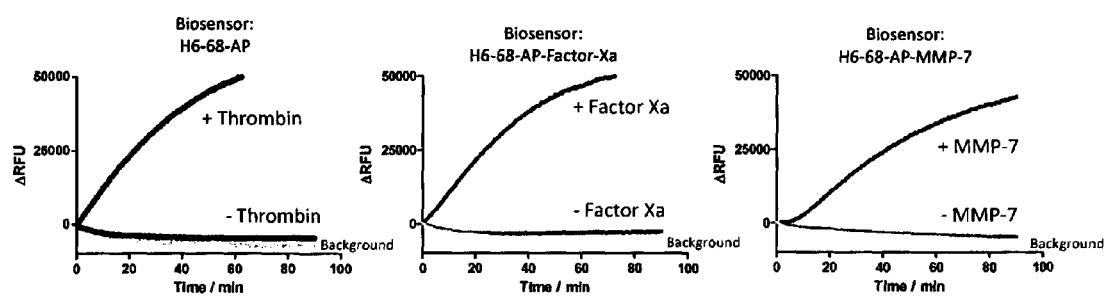
Figure 6:
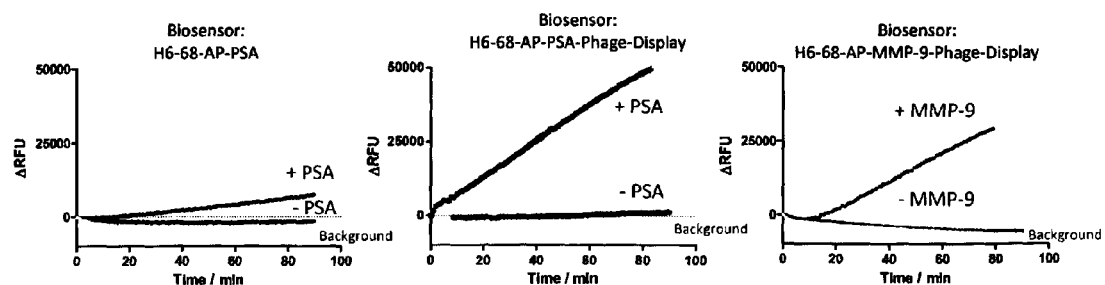

The constructs were expressed, purified and tested and found to be functional showing induction ratios ranging from approximately 2- to 150-fold following cleavage by the respective target protease under saturating reaction conditions. (FIG. 6). Some variability in the maximum induction ratio was observed depending on the nature of the connecting linker with Factor Xa, MMP-7 and MMP-9 showing significantly greater induction ratios compared to the natural PSA cleavage site. This can be due to a number of reasons. For instance, limited induction ratios in the uncleaved state can arise due to subtle variations in the linker that constrain it in a conformation that make it unfavourable for the AI-domain to bind to the active site of TVMV in the uncleaved state and thus reduce autoinhibtion. Alternatively, limited induction in the cleaved state can arise if the cleaved C-terminus retains affinity for the TVMV active site and continues to act as a competitive inhibitor. For instance, the optimal substrate sequence for TVMV and the natural substrate sequence for PSA share significant sequence features in the P1-P3 region ('KLQ' for PSA compared to 'RFQ' for TVMV) resulting in closely resembling cleavage products which may result in continuing autoinhibtion in the cleaved state.

Induction ratios can be optimized in a number of ways. For instance, limited inhibition in the uncleaved state can be improved by introducing additional glycine residues in the linker connecting the biosensor protease with its AI-domain in order to reduce conformational strain in the uncleaved state caused by the cleavage sites for different target protease. Alternatively, limited induction of activity in the cleaved state can be overcome by engineering the cleavage site for the target protease in such a way that any inhibitory effects of the cleaved C-terminal product are abolished while still retaining a natural cleavage propensity for the cleaved site for the target protease. This should be perfectly possible for different types of proteases given that in case of PSA the natural and phage display optimized cleavage sites (EHSSKLQ'SGA compared to LRLSSYY' respectively) differ substantially, and should be equally applicable to other proteases.

H6-68-AP-Factor-Xa:
(SEQ ID NO: 8)
Ssgskallkgvrdfnpisacvcllenssdghserlfgigfgpyiianqhl frrnngeltiktmhgefkvknstqlqmkpvegrdiivikmakdfppfpqk lkfrqptikdrvcmvstnfqqksvsslvsesshivhkedtsfwqhwittk dqqcqsplvsiidgnilgihslthttngsnyfyefpekfvatyldaadqw cknwkfnadkiswqsfilwedapedfmggiegrsggreyvrfapgsthhh hhh The encoding nucleotide sequence is:

(SEQ ID NO: 36)
Tctagtggttctaaagctttgctgaagggcgtgcgcgattttaatccgat ctctgcttgcgtatgcctgctggaaaactcctcggatggtcatagtgaac gtctgtttggcattggttttggcccgtatatcattgccaaccagcatctg -continued

```
tttcgtcgtaacaatggcgaactgaccatcaaaaccatgcatggtgaatt caaagtcaaaaactctacccagctgcagatgaaaccggttgaaggccgtg acattatcgttatcaaaatggctaaagacttcccgccgttcccgcagaaa ctgaaattccgtcagccgaccatcaaagatcgtgtgtgcatggtgtccac caactttcagcagaaaagcgtctcgagcctggtgtctgaatcctctcaca ttgtgcataaagaagacacttctttctggcagcactggatcaccactaaa gatggccagtgtggcagcccactagtttccatcattgatggcaacattct gggcatccacagcctgactcataccaccaacggtagcaactacttcgtgg aatttccggaaaaattcgtggcgacttatctagatgccgcggatggttgg tgcaaaaactggaaattcaacgcggataaaatcagctggggttccttat cctgtgggaagatgctccggaagacttcatgggtggtattgaaggtcgca gcggtggtcgcgaatatgtgcgctttgccccgggaagcacccaccaccat catcatcac
```

H6-68-AP-MMP-7:

(SEQ ID NO: 9)

<u>Ssgskallkqvrdfnpisacvcllenssdghserlfgigfgpyiianqhl</u>
<u>frrnngeltiktmhgefkvknstqlqmkpvegrdiivikmakdfppfpqk</u>
<u>lkfrqptikdrvcmvstnfqqksvsslvsesshivhkedtsfwqhwittk</u>
<u>dqqcqsplvsiidqnilqihslthttnqsnyfyefpekfvatyldaadqw</u>
<u>cknwkfnadkiswqsfilwedapedgg</u>rplalwrs<u>greyvrfap</u>gsthhh
hhh The encoding nucleotide sequence is:

(SEQ ID NO: 37)

```
Tctagtggttctaaagctttgctgaagggcgtgcgcgatttaatccgat actgcttgcgtatgcctgctggaaaactcctcggatggtcatagtgaacg tctgtttggcattggttttggcccgtatatcattgccaaccagcatctgt ttcgtcgtaacaatggcgaactgaccatcaaaaccatgcatggtgaattc aaagtcaaaaactctacccagctgcagatgaaaccggttgaaggccgtga cattatcgttatcaaaatggctaaagacttcccgccgttcccgcagaaac tgaaattccgtcagccgaccatcaaagatcgtgtgtgcatggtgtccacc aactttcagcagaaaagcgtctcgagcctggtgtctgaatcctdcacatt gtgcataaagaagacacttctttctggcagcactggatcaccactaaaga tggccagtgtggcagcccactagtttccatcattgatggcaacattctgg gcatccacagcctgactcataccaccaacggtagcaactacttcgtggaa tttccggaaaaattcgtggcgacttatctagatgccgcggatggttggtg caaaaactggaaattcaacgcggataaaatcagctggggttcctttatcc tgtgggaagatgctcctgaaggtggtcgcccactggctctgtggcgcagc ggtggtcgcgaatatgtgcgctttgccccgggaagcacccaccaccatca tcatcac
```

H6-68-AP-MMP-9-Phage-Display:

(SEQ ID NO: 10)

<u>Ssgskallkqvrdfnpisacvcllenssdghserlfgigfgpyiianqhl</u>
<u>frrnngeltiktmhgefkvknstqlqmkpvegrdiivikmakdfppfpqk</u>
<u>lkfrqptikdrvcmvstnfqqksvsslvsesshivhkedtsfwqhwittk</u>
<u>dqqcqsplvsiidqnilqihslthttnqsnyfyefpekfvatyldaadqw</u>
<u>cknwkfnadkiswqsfilwedapgg</u>lrlssyysga<u>greyvrfap</u>gsthhh
hhh The encoding nucleotide sequence is:

(SEQ ID NO: 38)

```
Tctagtggttctaaagattgctgaagggcgtgcgcgattttaatccgatc tctgcttgcgtatgcctgctggaaaactcctcggatggtcatagtgaacg tctgtttggcattggttttggcccgtatatcattgccaaccagcatctgt ttcgtcgtaacaatggcgaactgaccatcaaaaccatgcatggtgaattc aaagtcaaaaactctacccagctgcagatgaaaccggttgaaggccgtga cattatcgttatcaaaatggctaaagacttcccgccgttcccgcagaaac tgaaattccgtcagccgaccatcaaagatcgtgtgtgcatggtgtccacc aactttcagcagaaaagcgtctcgagcctggtgtctgaatcctctcacat tgtgcataaagaagacacttctttctggcagcactggatcaccactaaag atggccagtgtggcagcccactagtttccatcattgatggcaacattctg ggcatccacagcctgactcataccaccaacggtagcaactacttcgtgga atttccggaaaaattcgtggcgacttatctagatgccgcggatggttggt gcaaaaactggaaattcaacgcggataaaatcagctggggttcctttatc ctgtgggaagatgctcctggtggtagcggcaaaggtcctcgccagattac cgcgggtcgcgaatatgtgcgctttgccccgggaagcacccaccaccatc atcatcac
```

H6-68-AP-PSA:

(SEQ ID NO: 11)

<u>Ssgskallkqvrdfnpisacvcllenssdghserlfgigfgpyiianqhl</u>
<u>frrnngeltiktmhgefkvknstqlqmkpvegrdiivikmakdfppfpqk</u>
<u>lkfrqptikdrvcmvstnfqqksvsslvsesshivhkedtsfwqhwittk</u>
<u>dqqcqsplvsiidqnilqihslthttnqsnyfvefpekfvatyldaadqw</u>
<u>cknwkfnadkiswqsfilwedapgg</u>ehssklqsga<u>greyvrfap</u>gsthhh
hhh The encoding nucleotide sequence is:

(SEQ ID NO: 39)

```
Tctagtggttctaaagctttgctgaagggcgtgcgcgattttaatccgat ctctgcttgcgtatgcctgctggaaaactcctcggatggtcatagtgaac gtctgtttggcattggttttggcccgtatatcattgccaaccagcatctg tttcgtcgtaacaatggcgaactgaccatcaaaaccatgcatggtgaatt caaagtcaaaaactctacccagctgcagatgaaaccggttgaaggccgtg acattatcgttatcaaaatggctaaagacttcccgccgttccgcagaaa ctgaaattccgtcagccgaccatcaaagatcgtgtgtgcatggtgtccac caactttcagcagaaaagcgtctcgagcctggtgtctgaatcctctcaca ttgtgcataaagaagacacttctttctggcagcactggatcaccactaaa
```

-continued

```
gatggccagtgtggcagcccactagtttccatcattgatggcaacattct gggcatccacagcctgactcataccaccaacggtagcaactacttcgtgg aatttccggaaaaattcgtggcgacttatctagatgccgcggatggttgg tgcaaaaactggaaattcaacgcggataaaatcagctggggttcctttat cctgtgggaagatgctccgggtggtgaacatagcagcaaactgcagagcg gtgcgggtcgcgaatatgtgcgctttgccccgggaagcacccaccaccat catcatcac
```

H6-68-AP-PSA-Phage-Display:
(SEQ ID NO: 12)

<u>Ssqskallkqvrdfnpisacvcllenssdqhserlfqiqfqpyiianqhl</u>

<u>frrnngeltiktmhqefkvknstqlqmkpveqrdiivikmakdfppfpqk</u>

<u>lkfrqptikdrvcmvstnfqqksvsslvsesshivhkedtsfwqhwittk</u>

<u>dgqcgsplvsiidgnilgihslthttngsnyfvefpekfvatyldaadgw</u>

<u>cknwkfnadkiswqsfilwedapgg</u>lrlssyysgag<u>reyvrfap</u>gsthhh hhh

The encoding nucleotide sequence is:

(SEQ ID NO: 40)
```
Tctagtggttctaaagctttgctgaagggcgtgcgcgatttttaatccgat ctctgcttgcgtatgcctgctggaaaactcctcggatggtcatagtgaac gtctgtttggcattggttttggcccgtatatcattgccaaccagcatctg tttcgtcgtaacaatggcgaactgaccatcaaaaccatgcatggtgaatt caaagtcaaaaactctaccagctgcagatgaaaccggttgaaggccgtg acattatcgttatcaaaatggctaaagacttcccgccgttcccgcagaaa ctgaaattccgtcagccgaccatcaaagatcgtgtgtgcatggtgtccac caactttcagcagaaaagcgtctcgagcctggtgtctgaatcctctcaca ttgtgcataaagaagacacttctttctggcagcactggatcaccactaaa gatggccagtgtggcagcccactagtttccatcattgatggcaacattct gggcatccacagcctgactcataccaccaacggtagcaactacttcgtgg aatttccggaaaaattcgtggcgacttatctagatgccgcggatggttgg tgcaaaaactggaaattcaacgcggataaaatcagctggggttcctttat cctgtgggaagatgctccgggtggtctgcgcctgagcagctattatagcg gtgcgggtcgcgaatatgtgcgctttgccccgggaagcacccaccaccat catcatcac
```

Summary of TVMV-Specific Biosensors Based on HCV

To extent the concept of engineering artificially autoinhibited proteases to classes beyond cysteine proteases, we have created an autoinhibited protease based on the serine NS3 protease from Hepatitis C-virus. Analogous to NIa proteases, the native function of HCV protease is to process the viral polyprotein. Crucially, its substrate specificity does not cross-react with TVMV which means artificially autoinhibited signal transducers based on TVMV and HCV can potentially be applied in series to form linear cascades, relaying and amplification stage.

Applying the design principles used for the development of TVMV-based signal transducers, we engineered an autoinhibited version of the serine NS3 protease from Hepatitis C-virus (HCV) (FIG. 7A). Non-cleavable binding peptides capable of bridging the P1-P1' junction of the HCV's active site have previously been developed (see Ingallinella P. et al. *Optimization of the P'-region of peptide inhibitors of hepatitis C virus NS3/4A protease*, Biochemistry, 2000, 39, 12898-906). Hence, a TVMV-inducible autoinhibited signal transducer based on HCV was constructed by appending the peptide-based active site binder DELILCPLDL to its C-terminus via a linker containing a TVMV cleavage site. The resulting protein displayed essentially no background activity while exposure to TVMV resulted in greater than 100-fold increase of HCV activity (FIG. 7B).

HCV-TVMV-AI:
(SEQ ID NO: 13)
smstsgsgsgs<u>sakqsvvivqrinlsqdtaysqqtrqaaqiaatsatqrdk</u>

<u>nqvdgevqvlstatqsflatcvngvcwtvyhgagsktlagpkgpitqmyt</u>

<u>nvdqdlvqwpappqarsmtpctcqssdlylvtrhadvipvrrrqdsrqsl</u>

<u>lspvsylkqssggpllcpsghvvqifraavctrgvakavdfipvesmett</u> mrggggsggetvrfqsggsgg<u>delilcpldl</u>ggsggtghhhhhh

The encoding nucleotide sequence is:

(SEQ ID NO: 41)
```
agcatgagcactagtggcagcggcagtggcagcgctaaaggcagcgtcgt catcgtggggcgtatcaacctgtctggggacactgcatattctcagcaga cccgtggcgcagcgggtatcgcggcaacttccgctaccggccgggacaaa aaccaggtggatggcgaggtgcaggtgctttcaaccgcaacacagtctttt tctggctacatgcgtcaatggggtttgttggaccgtctatcacggggccg gatccaagacacttgcgggtccaaaaggccctattcccagatgtacaca aacgtggatcaagacctggttgggtggccggcaccaccgggagctcgtag tatgacaccttgcacttgtggtagctccgatctgtatctggtgacccgtc acgcagacgtcattccagtgcgccgtcggggagattcacgtggaagcctg ctgtccccacgtccagtctcttacctgaagggcagtagtggcggtccact gctgtgtccatcaggacatgttgtcggtatcttccgtgcagcagtgtgca cccgtggcgttgccaaggcggttgattttatccccgtggagtccatggaa actacaatgcgggtggtggtgggtctggcggtgaaactgtgcgctttca atctggcggttctggtggggatgaactgattctgtgcccgctggatctgg gtgggtctggtgggactgggcatcatcatcatcaccac
```

Summary of Improving the Sensitivity of PSA-Specific Biosensors Based on TVMV and TVMV-Specific Biosensors Based on HCV Through Direct Affinity Targeting The sensitivity of protease biosensor can be further improved by operably linking the protease biosensor with a domain displaying affinity to the target protease. This can either be achieved directly by forming a fusion or conjugate of the protease with the targeting domain such as single chain antibody, affibody, peptide, DNA, RNA or PNA aptamer or a small molecule. In this way, additional molecular recognition features can be introduced into the protease biosensor which provide better molecular recognition features compared to just a peptide substrate.

Figure 8:
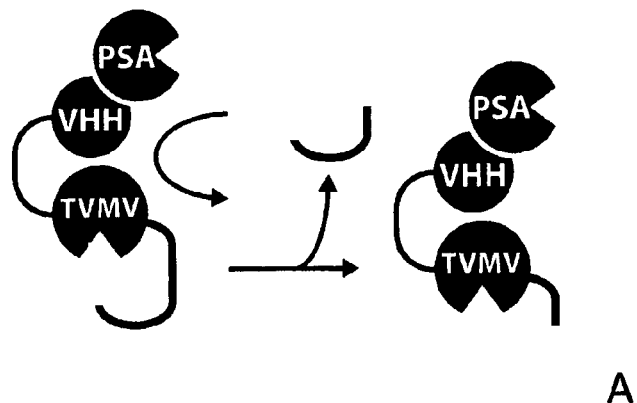
FIG. 8: Summary of direct affinity targeting with VHH domains. The sensitivity of the PSA-inducible biosensor based on TVMV can be improved by attaching a PSA-specific high affinity binder based on VHH domains either to the N- or C-terminus of the biosensor protease. In this way, the concentration between the PSA and PSA cleavage sites is increased leading to accelerated activation of the biosensor protease by the target protease and improved sensitivity.
Figure 8:
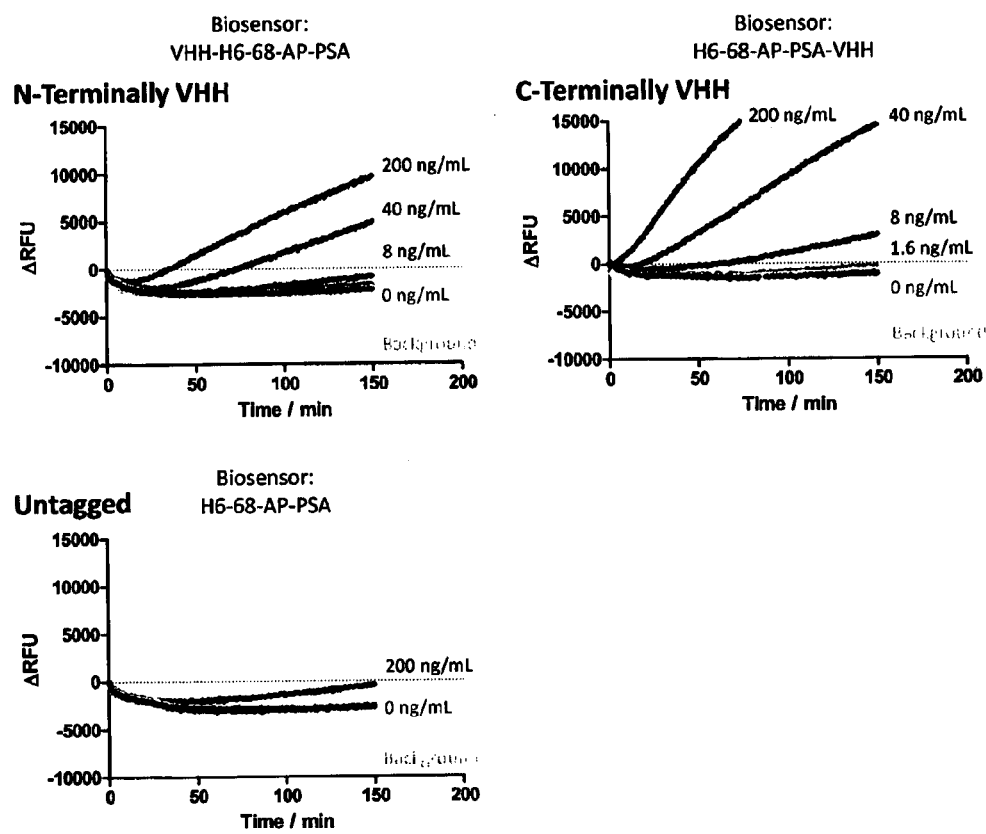

To this end, we created a fusion protein between the PSA-specific biosensor based on mutant H6-68-AP-PSA and a PSA-specific high affinity binder derived from VHH antibody domains (FIG. 8; Saerens, D. et al. *Single domain antibodies derived from dromedary lymph node and peripheral blood lymphocytes sensing conformational variants of prostate-specific antigen*, Journal of Biological Chemistry, 2004, 279, p. 51965-72). In this way, binding of the high affinity binder effects a higher effective concentration between the target and the biosensor proteases resulting in accelerated cleavage and activation of the protease biosensor. Activation can either occur through co-cleavage or rapid association and dissociation of the high affinity binder to PSA if simultaneous binding and activation of the PSA-inducible TVMV-based biosensor protease is prohibited for steric reasons. Which specific type of activation mechanism prevails will depend on the nature of the connecting linkers and the spatial orientation of the N- and C-termini of the TVMV-based biosensor and the high affinity binders as well as the orientation of the active site of PSA and the location of the binding epitope.

PSA-specific biosensors with VHH domains in both N- and C-terminal positions have been explored in association with a long and short linker providing suitable separation between the antigen binding site on PSA and the active site on PSA (FIG. 8B). Both types of configurations showed marked increases in the sensitivity of the assay with the C-terminal domain functioning slightly better by a factor of 2. Overall, this resulted in ca. 20-fold sensitivity gain of the sensor compared to untagged PSA-specific biosensors (FIG. 8).

H6-68-AP-PSA-VHH:
(SEQ ID NO: 14)
ssgskallkgvrdfnpisacvcllenssdghserlfgigfgpyiianqhl frrnngeltiktmhgefkvknstqlqmkpvegrdiivikmakdfppfpqk lkfrqptikdrvcmvstnfqqksvsslvsesshivhkedtsfwqhwittk dgqcgsplvsiidgnilgihslthttngsnyfvefpekfvatyldaadgw cknwkfnadkiswqsfilwedapggehssklqsgag*reyvrfap*ggsggs ggsggsggsggdvqlqesgggsvqaggslrlscvasgwiyippcmawfrq apgkerervatinpsgrtyyadstkgrfrisqdnvkrtlylymnslkped tatyycaaddgtcprmefddwqggtqvtvssggshhhhhh The encoding nucleotide sequence is:

(SEQ ID NO: 42)
tctagtggttctaaagctttgctgaagggcgtgcgcgattttaatccgat ctctgcttgcgtatgcctgctggaaaactcctcggatggtcatagtgaac gtctgtttggcattggttttggcccgtatatcattgccaaccagcatctg tttcgtcgtaacaatggcgaactgaccatcaaaaccatgcatggtgaatt caaagtcaaaaactctacccagctgcagatgaaaccggttgaaggccgtg acattatcgttatcaaaatggctaaagactttccgccgttcccgcagaaa ctgaaattccgtcagccgaccatcaaagatcgtgtgtgcatggtgtccac caactttcagcagaaaagcgtctcgagcctggtgtctgaatcctctcaca ttgtgcataaagaagacacttctttctggcagcactggatcaccactaaa gatggccagtgtggcagcccactagtttccatcattgatggcaacattct gggcatccacagcctgactcataccaccaacggtagcaactacttcgtgg aatttccggaaaaattcgtggcgacttatctagatgccgcggatggttgg tgcaaaaactggaaattcaacgcggataaaatcagctggggttcctttat cctgtgggaagatgctccgggtggtgaacatagcagcaaactgcagageg gtgcgggtcgcgaatatgtgcgctttgccccgggtggttctggcggtagt ggggggttctggtggctcgggcggttctgggggtgatgttcaactgcaaga aagcggtggtggtagcgttcaagcgggtggttccctgcgcctgtcgtgcg tcgcgtctggctggatttatattccgccgtgcatggcatggtttcgtcag gctccgggcaaggaacgtgaacgcgtcgcgaccattaacccgagtggccg cacctattacgccgattccacgaaaggtcgtttccgcatcagccaagaca acgttaagcgtaccctgtatctgtacatgaatagcctgaaaccggaagat accgcgacgtattactgcgcagcagatgatggtacgtgcccgcgcatgga atttgatgactggggccagggcacccaagtgacggttagctctggcggta gccatcatcatcatcatcat VHH-H6-68-AP-PSA:
(SEQ ID NO: 15)
sggdvqlqesgggsvqaggslrlscvasgwiyippcmawfrqapgkerer vatinpsgrtyyadstkgrfrisqdnvkrtlylymnslkpedtatyycaa ddgtcprmefddwqggtqvtvssggsggsggsggsggsggskallkgvrd fnpisacvcllenssdghserlfgigfgpyiianqhlfrrnngeltiktm hgefkvknstqlqmkpvegrdiivikmakdfppfpqklkfrqptikdrvc mvstnfqqksvsslvsesshivhkedtsfwqhwittkdgqcgsplvsiid gnilgihslthttngsnyfvefpekfvatyldaadgwcknwkfnadkisw gsfilwedapggehssklqsgag*reyvrfap*gsthhhhhh The encoding nucleotide sequence is:

(SEQ ID NO: 43)
agcggcggtgatgttcaactgcaagaaagcggtggtggtagcgttcaagc gggtggttccctgcgcctgtcgtgcgtcgcgtctggctggatttatattc cgccgtgcatggcatggtttcgtcaggctccgggcaaggaacgtgaacgc gtcgcgaccattaacccgagtggccgcacctattacgccgattccacgaa aggtcgtttccgcatcagccaagacaacgttaagcgtaccctgtatctgt acatgaatagcctgaaaccggaagataccgcgacgtattactgcgcagca gatgatggtacgtgcccgcgcatggaatttgatgactggggccagggcac ccaagtgacggttagctctggtggtagcggcggtagcggcggtagcggtg gctcgggcggttcgggcggttctaaagattgctgaagggcgtgcgcgatt -continued
```
ttaatccgatctctgcttgcgtatgcctgctggaaaactcctcggatggt catagtgaacgtctgtaggcattggttttggcccgtatatcattgccaac cagcatctgtttcgtcgtaacaatggcgaactgaccatcaaaaccatgca tggtgaattcaaagtcaaaaactctacccagctgcagatgaaaccggttg aaggccgtgacattatcgttatcaaaatggctaaagacttcccgccgttc ccgcagaaactgaaattccgtcagccgaccatcaaagatcgtgtgtgcat ggtgtccaccaactttcagcagaaaagcgtctcgagcctggtgtctgaat cctctcacattgtgcataaagaagacacttctttctggcagcactggatc accactaaagatggccagtgtggcagcccactagtttccatcattgatgg caacattctgggcatccacagcctgactcataccaccaacggtagcaact acttcgtggaatttccggaaaaattcgtggcgacttatctagatgccgcg gatggttggtgcaaaaactggaaattcaacgcggataaaatcagctgggg ttcctttatcctgtgggaagatgctccgggtggtgaacatagcagcaaac tgcagagcggtgcgggtcgcgaatatgtgcgctttgccccgggaagcacc caccaccatcatcatcac
```

Similarly, the sensitivity of signal transmission between thrombin-inducible biosensors based on TVMV and TVMV-inducible biosensors based on HCV could be improved by direct affinity targeting based on artificially protein-peptide interactions. In the absence of affinity targeting interactions, µM concentrations of TVMV are required to efficiently activate the TVMV-inducible HCV-based signal transducer. This is because of the relatively high $K_m$ of TVMV for its substrate peptide. This results in low turnover of the substrate and inefficient signal relay between the TVMV- and HCV-based signal transducers. The problem could be overcome by increasing the local concentration of the TVMV- and HCV-based signal transducers by means of affinity targeting based on artificial protein-protein interactions. We chose the SH3 domain with their proline-rich ligand peptides that have been extensively used by nature and synthetic biologists to scaffold cellular signaling pathways (see Whitaker, W. R. *Metabolic pathway flux enhancement by synthetic protein scaffolding*, Methods in Enzymology, 2011, 497, p. 497-68). Hence, an SH3 domain derived from the first SH3 domain of Crk was fused to the N-terminus of the TVMV-based signal transducer. Affinity targeting demonstrated a marked increase in sensitivity with as little as 10 nM of the TVMV-based signal transducer eliciting robust signal transmission and amplification between TVMV- and HCV-based signal transducers (FIG. 9B). In the absence of the SH3-domain, no detectable response was observed at these low concentrations (FIG. 9B). At the same time, the induction ratio was reduced from 200-fold to 20-fold indicating a trade-off between sensitivity and specificity. Arguably, this is due to the relatively high effective concentration between the HCV-based and TVMV-based signal transducers and their mutual cleavage sites when they are artificially co-localized through high affinity binding interactions leading to a higher rate of non-specific activation of HCV by TVMV.

SH3-H6-68-AP:

(SEQ ID NO: 16)

sggsgaeyvralfdfngndeedlpfkkgdilrirdkpeeqwwnaedsegk rgmipvpyvekyrpasasvsaliggrggsggsggsggsggsggsskallk -continued gvrdfnpisacvellenssdghserlfgigfgpyiianqhlfrrnngelt iktmhgefkvknstqlqmkpvegrdiivikmakdfppfpqklkfrqptik drvcmvstnfqqksvsslvsesshivhkedtsfwqhwittkdgqcgsplv siidgnilgihslthttngsnyfvefpekfvatyldaadgwcknwkfnad kiswgsfilwedapedfmsglvprgvgreyvrfapgsthhhhhh The encoding nucleotide sequence is:

(SEQ ID NO: 44)

tctggtggttctggggcagagtatgtgcgggccctctttgactttaatgg gaatgatgaagaagatcttccatttaagaaaggagacatcctgcgtatcc gggataagcctgaagagcagtggtggaatgcagaggacagcgaaggaaag cgtgggatgattcctgtcccttacgtggagaagtatcgccctgcctccgc ctcagtatcggctctgattggaggtcggggcggtagcggtggtagcggcg gtagcggcggtagcggtggctcgggcggttcgtctaaagctttgctgaag ggcgtgcgcgattttaatccgatctctgcttgcgtatgcctgctggaaaa ctcctcggatggtcatagtgaacgtctgtttggcattggttttggcccgt atatcattgccaaccagcatctgtttcgtcgtaacaatggcgaactgacc atcaaaaccatgcatggtgaattcaaagtcaaaaactctacccagctgca gatgaaaccggttgaaggccgtgacattatcgttatcaaaatggctaaag acttcccgccgttcccgcagaaactgaaattccgtcagccgaccatcaaa gatcgtgtgtgcatggtgtccaccaactttcagcagaaaagcgtctcgag cctggtgtctgaatcctctcacattgtgcataaagaagacacttctttct ggcagcactggatcaccactaaagatggccagtgtggcagcccactagtt tccatcattgatggcaacattctgggcatccacagcctgactcataccac caacggtagcaactacttcgtggaatttccggaaaaattcgtggcgactt atctagatgccgcggatggttggtgcaaaaactggaaattcaacgcggat aaaatcagctggggttcctttatcctgtgggaagatgcgccggaagactt catgagtggtctggtgccgcgcggtgtaggtcgcgaatatgtgcgctttg ccccgggaagcacccaccaccatcatcatcac SH3-Peptide-HCV-TVMV-AI-28:

(SEQ ID NO: 17)

smstsgppppl ppkrrrggsggsggsakgsvvivgrinlsgdtaysqqtr gaagiaatsatgrdknqvdgevqvlstatqsflatcvngvcwtvyhgags ktlagpkgpitqmytnvdqdlvgwpappgarsmtpctcgssdlylvtrha dvipvrrrgdsrgsllsprpvsylkgssggpllcpsghvvgifraayctr gvakavdfipvesmettmrggggsggetvrfqsggsggdelilcpldlgg sggtghhhhhh The encoding nucleotide sequence is:

(SEQ ID NO: 45)

agcatgagcactagtggtcctccgcctcctcttccgcctaagcgtcgccg tggcggtagcggtggtagcggtggcagcgctaaaggcagcgtcgtcatcg tggggcgtatcaacctgtctggggacactgcatattctcagcagacccgt -continued
```
ggcgcagcgggtatcgcggcaacttccgctaccggccgggacaaaaacca ggtggatggcgaggtgcaggtgctttcaaccgcaacacagtcttttctgg ctacatgcgtcaatgggg tttgttggaccgtctatcacggggccggatcc aagacacttgcgggtccaaaaggccctattacccagatgtacacaaacgt ggatcaagacctggttgggtggccggcaccaccgggagctcgtagtatga caccttgcacttgtggtagctccgatctgtatctggtgaccegtcacgca gacgtcattccagtgcgccgtcggggagattcacgtggaagcctgctgtc cccacgtccagtctcttacctgaagggcagtagtggcggtccactgctgt gtccatcaggacatgttgtcggtatcttccgtgcagcagtgtgcaccegt ggcgttgccaaggcggttgattttatccccgtggagtccatggaaactac aatgcggggtggtggtgggtctggcggtgaaactgtgcgctttcaatctg gcggttctggtggggatgaactgattctgtgcccgctggatctgggtggg tctggtgggactgggcatcatcatcatcaccac SH3-Peptide-HCV-TVMV-AI-25:
                                          (SEQ ID NO: 18)
Smstsgsgsgsakqsvvivqrinlsqdtaysqqtrqaaqiaatsatqrdk nqvdqevqvlstatqsflatcvnqvcwtvyhgaqsktlaqpkqpitqmyt nvdqdlvqwpappgarsmtpctcgssdlylvtrhadvipvrrrgdsrgsl lsprpvsylkgssgqpllcpsghvvgifraavctrgvakavdfipvesme ttmrggsggsggetvrfqsggsggdelilcpldlggsggsggppplppk rrrggtghhhhhh
```

The encoding nucleotide sequence is:

```
                                          (SEQ ID NO: 46)
Agcatgagcactagtggcagcggcagtggcagcgctaaaggcagcgtcgt catcgtgggcgtatcaacctgtctggggacactgcatattctcagcaga cccgtggcgcagcgggtatcgcggcaacttccgctaccggccgggacaaa aaccaggtggatggcgaggtgcaggtgctttcaaccgcaacacagtcttt tctggctacatgcgtcaatgggg tttgttggaccgtctatcacggggccg gatccaagacacttgcgggtccaaaaggccctattacccagatgtacaca aacgtggatcaagacctggttgggtggccggcaccaccgggagctcgtag tatgacaccttgcacttgtggtagctccgatctgtatctggtgaccegtc acgcagacgtcattccagtgcgccgtcggggagattcacgtggaagcctg ctgtccccacgtccagtctcttacctgaagggcagtagtggcggtccact gctgtgtccatcaggacatgttgtcggtatcttccgtgcagcagtgtgca cccgtggcgttgccaaggcggttgattttatccccgtggagtccatggaa actacaatgcggggtggttctggtgggtctggcggtgaaactgtgcgctt tcaatctggcggttctggtggggatgaactgattctgtgcccgctggatc tgggtgggtctggtgggtctggtgggcctccgcctcctcttccgcctaag cgtcgccgtggtgggactgggcatcatcatcatcaccac
```

Summary of Improving the Sensitivity of Thrombin Specific Biosensors Through Indirect Affinity Targeting Alternatively affinity targeting can be achieved indirectly by fusing the biosensor with the domain that constitutively or inducibly associates with the domain displaying affinity to the target protease. For example, the ZZ-domain is an engineered derivative of protein A which specifically binds to the Fc portion of IgG molecules (Nilsson, B., T. Moks, B. Jansson, L. Abrahmsen, A. Elmblad, E. Holmgren, C. Henrichson, T. A. Jones, and M. Uhlen. "A Synthetic IgG-Binding Domain Based on Staphylococcal Protein A." Protein Eng 1, no. 2 (1987): 107-13). In this way, it becomes possible to co-localize thrombin and the thrombin specific biosensor on a single IgG molecule, thus increasing their effective concentration, accelerating activation of the biosensor and improving the sensitivity of the assay. An example of a biosensor comprising a ZZ domain is shown in FIG. 6.

To optimize induction ratios and improve the sensitivity, a number of factors can be optimized: (i) the length and the structure of the linker connecting the ZZ domain to the protease biosensors, (ii) the strength of affinity interactions between the monoclonal antibody and the target protease, (iii) the strength of affinity interactions between the Fc portion and the protease biosensor and (iii) the concentration of the monoclonal antibody and protease biosensor to achieve optimal formation of the ternary complex and specific induction of protease activities over background.

The thrombin specific biosensor (300 nM) was incubated together with protease substrate (10 μM) and a monoclonal antibody specific to human thrombin (150 nM, Thrombin Monoclonal Antibody 5020, Thermoscientific MAI-43019) in 50 mM Tris-HCl and 5 mM EDTA, pH 8.0. Relief of autoinhibition was achieved upon addition of human thrombin (between 1-15 mU per 200 μL).

Figure 10:
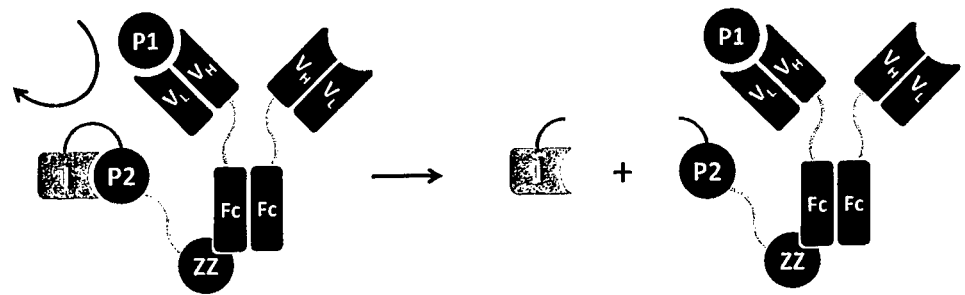
FIG. 10: The sensitivity of a protease biosensor can be enhanced by fusing it to a ZZ-domain and assaying the activity of a target protease in the presence of an IgG molecule which specifically binds to the target protease. In this way, the target and biosensor protease co-localize on a single IgG molecule thus increasing their effective concentration and accelerating activation of the biosensor. Addition of a thrombin-specific monoclonal antibody (5020) improves the sensitivity of the thrombin biosensors when it is fused to the ZZ-domain, but not in its absence.
Figure 10:
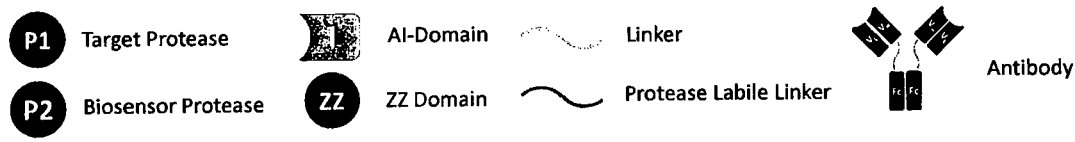
Figure 10:
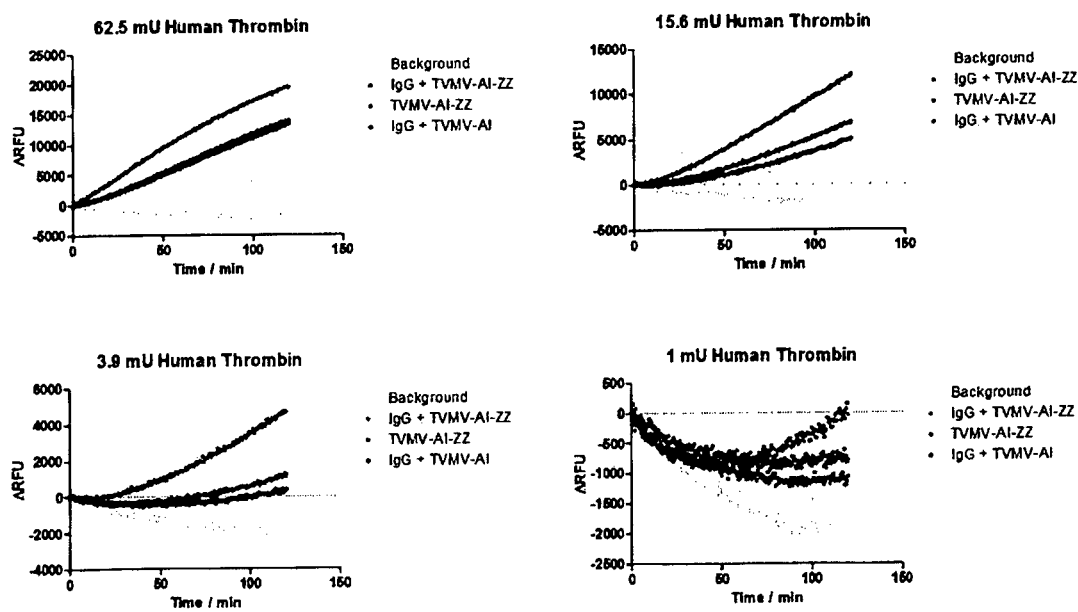

Addition of a thrombin specific monoclonal antibody (5020) improves the sensitivity of the thrombin biosensors when it is fused to the ZZ-domain, but not in its absence as shown in FIG. 10.

```
H6-68-AI-ZZ
                                          (SEQ ID NO: 19)
Ssgskallkgvrdfnpisacvcllenssdghserlfgigfgpyiianqhl frrnngeltiktmhgefkvknstqlqmkpvegrdiivikmakdfppfpqk lkfrqptikdrvcmvstnfqqksvsslvsesshivhkedtsfwqhwittk dgqcgsplvsiidgnilgihslthttngsnyfvefpekfvatyldaadgw cknwkfnadkiswgsfilwedapedfmsglvprgvgreyvrfapasssg taqhdeavdnkfnkeqqnafyeilhlpnlneeqrnafiqslkddpsqsan llaeakklndaqapkvdnkfnkeqqnafyeilhlpnlneeqrnafiqslk ddpsqsanllaeakklndaqapkgsthhhhhh
```

The encoding nucleotide sequence is:

```
                                          (SEQ ID NO: 47)
Tctagtggttctaaagctttgctgaagggcgtgcgcgatttt aatccgat ctctgcttgcgtatgcctgctggaaaactcctcggatggtcatagtgaac
```

-continued
```
gtctgtttggcattggttttggcccgtatatcattgccaaccagcatctg tttcgtcgtaacaatggcgaactgaccatcaaaaccatgcatggtgaatt caaagtcaaaaactctacccagctgcagatgaaaccggttgaaggccgtg acattatcgttatcaaaatggctaaagacttcccgccgttcccgcagaaa ctgaaattccgtcagccgaccatcaaagatcgtgtgtgcatggtgtccac caactttcagcagaaaagcgtctcgagcctggtgtctgaatcctctcaca ttgtgcataaagaagacacttctttctggcagcactggatcaccactaaa gatggccagtgtggcagcccactagtttccatcattgatggcaacattct gggcatccacagcctgactcataccaccaacggtagcaactacttcgtgg aatttccggaaaaattcgtggcgacttatctagatgccgcggatggttgg tgcaaaaactggaaattcaacgcggataaaatcagctggggttcctttat cctgtgggaagatgcgccggaagacttcatgagtggtctggtgccgcgcg gtgtaggtcgcgaatatgtgcgctttgccccggctagcagtagcagcggt accgcgcaacacgatgaagccgtagacaacaaattcaacaaagaacaaca aaacgcgttctatgagatcttacatttacctaacttaaacgaagaacaac gaaacgccttcatccaaagtttaaaagatgacccaagccaaagcgctaac cttttagcagaagctaaaaagctaaatgacgcacaagctccgaaggtaga caacaaattcaacaaagaacaacaaaacgcgttctatgagatcttacatt tacctaacttaaacgaagaacaacgaaacgccttcatccaaagtttaaaa gatgacccaagccaaagcgctaacccttttagcagaagctaaaaagctaaa tgatgctcaggcgccgaaaggaagcacccaccaccatcatcatcac
```

ZZ-AI-H6-68

(SEQ ID NO: 20)
Aqhdeavdnkfnkeqqnafyeilhlpnlneeqrnafiqslkddpsqsanl laeakklndaqapkvdnkfnkeqqnafyeilhlpnlneeqrnafiqslkd dpsqsanllaeakklndaqapkassssgtskallkgvrdfnpisacvcll enssdghserlfgigfgpyiianqhlfrrnngeltiktmhgefkvknstq lqmkpvegrdiivikmakdfppfpqklkfrqptikdrvcmvstnfqqksv sslvsesshivhkedtsfwqhwittkdgqcgsplvsiidgnilgihslth ttngsnyfvefpekfvatyldaadgwcknwkfnadkiswgsfilwedape dfmsglvprgvgreyvrfapgsthhhhhh The encoding nucleotide sequence is:

(SEQ ID NO: 48)
Gcgcaacacgatgaagccgtagacaacaaattcaacaaagaacaacaaaa cgcgttctatgagatcttacatttacctaacttaaacgaagaacaacgaa acgccttcatccaaagtttaaaagatgacccaagccaaagcgctaaccttt ttagcagaagctaaaaagctaaatgacgcacaagctccgaaggtagacaa caaattcaacaaagaacaacaaaacgcgttctatgagatcttacatttac ctaacttaaacgaagaacaacgaaacgccttcatccaaagtttaaaagat -continued
```
gacccaagccaaagcgctaaccttttagcagaagctaaaaagctaaatga tgctcaggcgccgaaagctagcagtagcagcggtacctctaaagctttgc tgaagggcgtgcgcgattttaatccgatctctgcttgcgtatgcctgctg gaaaactcctcggatggtcatagtgaacgtagtttggcattggttttggc ccgtatatcattgccaaccagcatctgtttcgtcgtaacaatggcgaact gaccatcaaaaccatgcatggtgaattcaaagtcaaaaactctacccagc tgcagatgaaaccggttgaaggccgtgacattatcgttatcaaaatggct aaagacttcccgccgttcccgcagaaactgaaattccgtcagccgaccat caaagatcgtgtgtgcatggtgtccaccaactttcagcagaaaagcgtct cgagcctggtgtctgaatcctctcacattgtgcataaagaagacacttct ttctggcagcactggatcaccactaaagatggccagtgtggcagcccact agtttccatcattgatggcaacattctgggcatccacagcctgactcata ccaccaacggtagcaactacttcgtggaatttccggaaaaattcgtggcg acttatctagatgccgcggatggttggtgcaaaaactggaaattcaacgc ggataaaatcagctggggttcctttatcctgtgggaagatgcgccggaag acttcatgagtggtctggtgccgcgcggtgtaggtcgcgaatatgtgcgc tttgccccgggaagcacccaccaccatcatcatcac
```

Summary of Allosteric Receptor Data

Figure 11:
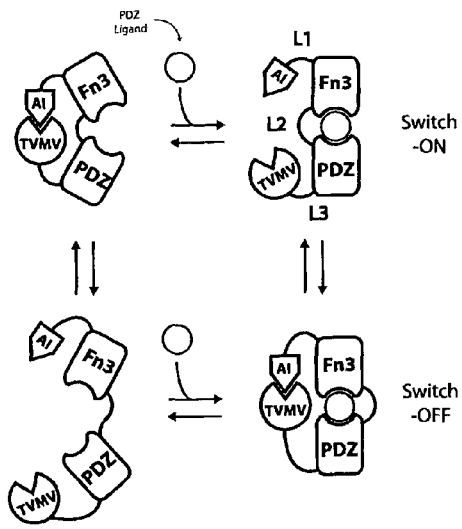
FIG. 11: An allosteric receptor can be created by fusing a biosensor protease and an AI-domain to the N- and C-terminus of an affinity clamp, respectively. Upon ligand binding, the complex is stabilized in a closed, autoinhibited conformation resulting in a reduction of protease activity. Modulation of affinity clamp "allosteric" biosensor protease activity by ligand binding to the PDZ/FN affinity clamp. Solely by changing the length and structure of the connecting linkers L1, L2 and L3, it becomes possible to modulate the induction ratio and the mode of activation covering switch-ON to switch-OFF responses following addition of the ligand.
Figure 11:
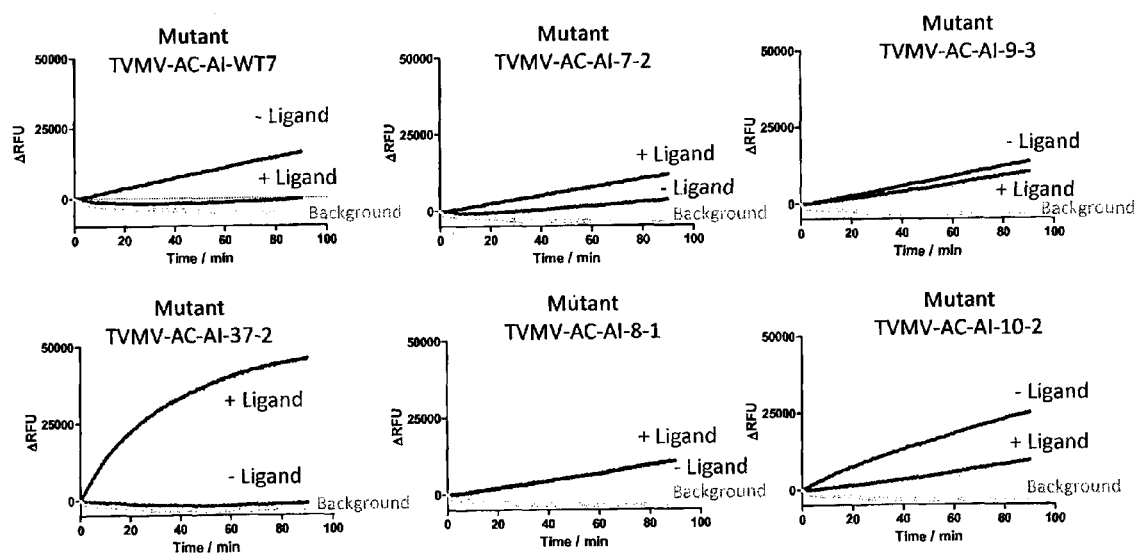
Figure 11:
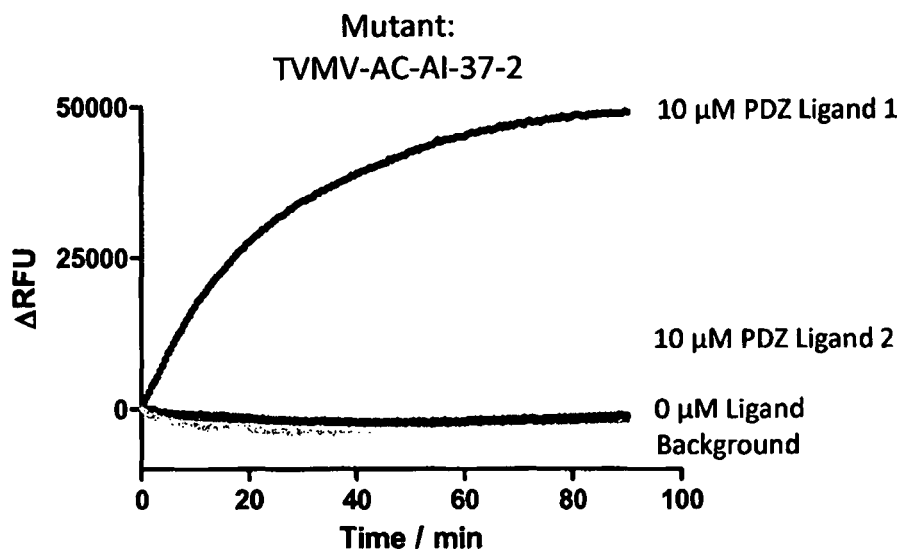

An affinity clamp "allosteric" biosensor molecule was generated by fusing TVMV with a PDZ/FN affinity clamp and an AI-domain (see FIG. 4D and FIG. 11). Optimisation of the fold induction requires consideration of both the linker length and linker structure (random coil, alpha helix) connecting the protease and the affinity clamp and the AI-domain.

The affinity clamp comprises the PDZ domain from human protein Erbin as the capture domain. Erbin-PDZ binds to the C-termini of p120-related catenins (δ-catenin and Armadillo repeat gene deleted in Velo-cardio-facial syndrome (ARVCF)) with a low-micromolar dissociation constant ($K_d$). The fibronectin type III domain of human fibronectin (FN3) was used as the enhancer domain. FN3 is a robust scaffold for producing antibody-like binding proteins with three surface loops available for creating a repertoire of binding interfaces.

A set of different allosterically regulated proteases was constructed by varying the composition of the three different linkers connecting TVMV to the Erbin-PDZ domain (Linker 1), the Erbin-PDZ domain to the FN3 domain (Linker 2) and the FN3 domain to the AI-domain (Linker 3). Notably, solely by varying the sequence and the length of the connecting linkers 1-3, it was possible to change the induction of activity as well as the mode of action from approximately 100-fold switch-ON to 6-fold switch-OFF. The largest modulation was effected by progressively shortening and lengthening linker L1. The induction of activity can also be fine-tuned with ligands of different affinity for the Erbin-PDZ-FN affinity clamp complex (FIG. 11C) with a lower affinity PDZ peptide ligand-2 achieving approximately 10-fold lower induction of activity compared to the higher affinity PDZ peptide ligand-1 (RGSIDTWV).

The allosteric receptor (0.4 µM or 0.8 µM as indicated) was incubated together with 10 µM TVMV protease substrate in 50 mM Tris-HCl, 1 M NaCl, 1 mM DTT and 0.5 mM EDTA. As shown in FIG. 11, modulation of protease activity was achieved upon addition of 10 μM PDZ ligand peptide-1 (RGSIDTWV).

The amino acid sequences of the biosensor molecules comprising the affinity clamp is as follows. The protease amino acid sequence is underlined, the amino acid sequence of the affinity clamp is bolded and the amino acid sequence of the autoinhibitor peptide is double-underlined. The His-tag is at the C-terminus. Linker sequences are in plain font.

TVMV-AC-AI-WT7:

(SEQ ID NO: 21)
Ssgskallkgvrdfnpisacvcllenssdghserlfgigfgpyiianqhl frrnngeltiktmhgefkvknstqlqmkpveqrdiivikmakdfppfpqk lkfrqptikdrvcmvstnfqqksvsslvsesshivhkedtsfwqhwittk dgqcgsplvsiidgnilgihslthttngsnyfvefpekfvatyldaadgw cknwkfnadkiswqsfilwedapedsgspelgfsisggvggrgnpfrpdd dgifvtrvqpegpaskllqpgdkiiqangysfiniehgqavsllktfqnt veliivrevgngakqeirvrvekdggsggvssvptnlevvaatptsllis wdayrelpvsyyrityqetggnspvqeftvpgskstatisglkpgvdyti tvyahynyhyysspisinyrgp<u>greyvrfap</u>gsthhhhhh The encoding nucleotide sequence is:

(SEQ ID NO: 49)
tctagtggttctaaagctttgctgaagggcgtgcgcgattttaatccgat ctctgcttgcgtatgcctgctggaaaactcctcggatggtcatagtgaac gtctgtttggcattggttttggcccgtatatcattgccaaccagcatctg tttcgtcgtaacaatggcgaactgaccatcaaaaccatgcatggtgaatt caaagtcaaaaactctacccagctgcagatgaaaccggttgaaggccgtg acattatcgttatcaaaatggctaaagacttcccgccgttcccgcagaaa ctgaaattccgtcagccgaccatcaaagatcgtgtgtgcatggtgtccac caactttcagcagaaaagcgtctcgagcctggtgtctgaatcctctcaca ttgtgcataaagaagacacttattctggcagcactggatcaccactaaag atggccagtgtggcagcccactagtttccatcattgatggcaacattctg ggcatccacagcctgactcataccaccaacggtagcaactacttcgtgga atttccggaaaaattcgtggcgacttatctagatgccgcggatggttggt gcaaaaactggaaattcaacgcggataaaatcagctgggttcctttatc ctgtgggaagatgcgccggaagatagtggtagtccggagttaggttttag tatttcaggtggtgtcggtggtcgtgggaatccttttcgtccagatgatg atggaattttcgttacgcgtgtccagccggagggcccagctagcaagctg ctgcaacctggggataaaatcattcaagctaacggttatagctttatcaa cattgaacatggccaagctgtcagcttactgaaaaccttttcagaacacag tcgaactgattatcgttcgcgaggtgggtaatggtgccaagcaggaaatc cgcgttcgcgtggaaggatggcggcagtggtggggtttcttctgtgcc gactaacctggaagttgtcgcggccactcctacaagtctgctgattagct gggatgcctatcgtgaactgccggtttcttattaccgcatcacgtacggt -continued
gagacaggcggtaatagtcctgttcaagagtttactgtacctggtagcaa aagcaccgcgactattagtgggctgaagccgggagtggattacaccatca ccgtatatgctcattataattatcactactatagctcaccgatcagcatt aactatcgtggtcctggtcgcgaatatgtgcgctttgccccgggaagcac ccaccaccatcatcatcac

TVMV-AC-AI-37-2:

(SEQ ID NO: 22)
ssgskallkgvrdfnpisacvcllenssdghserlfgigfgpyiianqhl frrnngeltiktmhgefkvknstqlqmkpveqrdiivikmakdfppfpqk lkfrqptikdrvcmvstnfqqksvsslvsesshivhkedtsfwqhwittk dgqcgsplvsiidgnilgihslthttngsnyfvefpekfvatyldaadgw cknwkfnadkiswgsfilwesgspelgfsisggvggrgnpfrpdddgifv trvqpegpaskllqpgdkiiqangysfiniehgqavsllktfqntvelii vrevgngakqeirvrvekdggsgggvssvptnlevvaatptsllliswday relpvsyyrityqetggnspvqeftvpgskstatisglkpgvdytitvya hynyhyysspisinyrgp<u>greyvrfap</u>gsthhhhhh The encoding nucleotide sequence is:

(SEQ ID NO: 50)
tctagtggttctaaagctttgctgaagggcgtgcgcgattttaatccgat ctctgcttgcgtatgcctgctggaaaactcctcggatggtcatagtgaac gtctgtttggcattggttttggcccgtatatcattgccaaccagcatctg tttcgtcgtaacaatggcgaactgaccatcaaaaccatgcatggtgaatt caaagtcaaaaactctacccagctgcagatgaaaccggttgaaggccgtg acattatcgttatcaaaatggctaaagacttcccgccgttcccgcagaaa ctgaaattccgtcagccgaccatcaaagatcgtgtgtgcatggtgtccac caactttcagcagaaaagcgtctcgagcctggtgtctgaatcctctcaca ttgtgcataaagaagacacttattctggcagcactggatcaccactaaag atggccagtgtggcagcccactagtttccatcattgatggcaacattctg ggcatccacagcctgactcataccaccaacggtagcaactacttcgtgga atttccggaaaaattcgtggcgacttatctagatgccgcggatggttggt gcaaaaactggaaattcaacgcggataaaatcagctgggttcctttatc ctgtgggaaagtggtagtccggagttaggttttagtatttcaggtggtgt cggtggtcgtgggaatcatttcgtccagatgatgatggaattttcgttac gcgtgtccagccggagggcccagctagcaagctgctgcaacctggggata aaatcattcaagctaacggttatagctttatcaacattgaacatggccaa gctgtcagcttactgaaaaccttttcagaacacagtcgaactgattatcgt tcgcgaggtgggtaatggtgccaagcaggaaatccgcgttcgcgtggaga aggatggcggcagtggtgggggtgtatcttctgtgccgactaacctggaa gttgtcgcggccactcctacaagtctgctgattagctgggatgcctatcg tgaactgccggtttcttattaccgcatcacgtacggtgagacaggcggta atagtcctgttcaagagtttactgtacctggtagcaaaagcaccgcgact -continued attagtgggctgaagccgggagtggattacaccatcaccgtatatgctca
ttataattatcactactatagctcaccgatcagcattaactatcgtggtc
ctggtcgcgaatatgtgcgctttgccccgggaagcacccaccaccatcat
catcac

TVMV-AC-AI-42-1:

(SEQ ID NO: 23)

ssgskallkgvrdfnpisacvcllenssdghserlfgigfgpyiianqhl
frrnngeltiktmhgefkvknstqlqmkpvegrdiivikmakdfppfpqk
lkfrqptikdrvcmvstnfqqksvsslvsesshivhkedtsfwqhwittk
dgqcgsplvsiidgnilgihslthttngsnyfvefpekfvatyldaadgw
cknwkfnadkiswgsfilwesgspelgfsisggvggrgnpfrpdddgifv
trvqpegpaskllqpgdkiiqangysfiniehggqavsllktfqntvelii
vrevgngakqeirvrvekdggsggggsggsvssvptnlevvaatptslli
swdayrelpvsyyritygetggnspvqeftvpgskstatisglkpgvdyt
itvyahynyhyysspisinyrgpgreyvrfapgsthhhhhh The encoding nucleotide sequence is:

(SEQ ID NO: 51)

tctagtggttctaaagctttgctgaagggcgtgcgcgattttaatccgat
ctctgcttgcgtatgcctgctggaaaactcctcggatggtcatagtgaac
gtctgtttggcattggttttggcccgtatatcattgccaaccagcatctg
tttcgtcgtaacaatggcgaactgaccatcaaaaccatgcatggtgaatt
caaagtcaaaaactctacccagctgcagatgaaaccggttgaaggccgtg
acattatcgttatcaaaatggctaaagacttcccgccgttcccgcagaaa
ctgaaattccgtcagccgaccatcaaagatcgtgtgtgcatggtgtccac
caactttcagcagaaaagcgtctcgagcctggtgtctgaatcctctcaca
ttgtgcataaagaagacacttctttctggcagcactggatcaccactaaa
gatggccagtgtggcagcccactagtttccatcattgatggcaacattct
gggcatccacagcctgactcataccaccaacggtagcaactacttcgtgg
aatttccggaaaaattcgtggcgacttatctagatgccgcggatggttgg
tgcaaaaactggaaattcaacgcggataaaatcagctggggttcctttat
cctgtgggaaagtggtagtccggagttaggttttagtatttcaggtggtg
tcggtggtcgtgggaatccttttcgtccagatgatgatggaattttcgtt
acgcgtgtccagccggagggcccagctagcaagctgctgcaacctgggga
taaaatcattcaagctaacggttatagctttatcaacattgaacatggcc
aagctgtcagcttactgaaaacctttcagaacacagtcgaactgattatc
gttcgcgaggtgggtaatggtgccaagcaggaaatccgcgttcgcgtgga
gaaggatggcggcagtggtgggggtgggtctgggggttctgtatcttctg
tgccgactaacctggaagttgtcgcggccactcctacaagtctgctgatt
agctgggatgcctatcgtgaactgccggtttcttattaccgcatcacgta
cggtgagacaggcggtaatagtcctgttcaagagtttactgtacctggta
gcaaaagcaccgcgactattagtgggctgaagccgggagtggattacacc
atcaccgtatatgctcattataattatcactactatagctcaccgatcag
cattaactatcgtggtcctggtcgcgaatatgtgcgctttgccccgggaa
gcacccaccaccatcatcatcac

TVMV-AC-AI-7-2:

(SEQ ID NO: 24)

ssgskallkgvrdfnpisacvcllenssdghserlfgigfgpyiianqhl
frrnngeltiktmhgefkvknstqlqmkpvegrdiivikmakdfppfpqk
lkfrqptikdrvcmvstnfqqksvsslvsesshivhkedtsfwqhwittk
dgqcgsplvsiidgnilgihslthttngsnyfvefpekfvatyldaadgw
cknwkfnadkiswgsfilwegsgspelgfsisggvggrgnpfrpdddgif
vtrvqpegpaskllqpgdkiiqangysfiniehggqavsllktfqntveli
ivrevgngakqeirvrvekdggsggggsggsvssvptnlevvaatptsll
iswdayrelpvsyyritygetggnspvqeftvpgskstatisglkpgvdy
titvyahynyhyysspisinyrgpgreyvrfapgsthhhhhh The encoding nucleotide sequence is:

(SEQ ID NO: 52)

tctagtggttctaaagctttgctgaagggcgtgcgcgattttaatccgat
ctctgcttgcgtatgcctgctggaaaactcctcggatggtcatagtgaac
gtctgtttggcattggttttggcccgtatatcattgccaaccagcatctg
tttcgtcgtaacaatggcgaactgaccatcaaaaccatgcatggtgaatt
caaagtcaaaaactctacccagctgcagatgaaaccggttgaaggccgtg
acattatcgttatcaaaatggctaaagacttcccgccgttcccgcagaaa
ctgaaattccgtcagccgaccatcaaagatcgtgtgtgcatggtgtccac
caactttcagcagaaaagcgtctcgagcctggtgtctgaatcctctcaca
ttgtgcataaagaagacacttctttctggcagcactggatcaccactaaa
gatggccagtgtggcagcccactagtttccatcattgatggcaacattct
gggcatccacagcctgactcataccaccaacggtagcaactacttcgtgg
aatttccggaaaaattcgtggcgacttatctagatgccgcggatggttgg
tgcaaaaactggaaattcaacgcggataaaatcagctggggttcctttat
cctgtgggaaggtagtggtagtccggagttaggttttagtatttcaggtg
gtgtcggtggtcgtgggaatccttttcgtccagatgatgatggaattttc
gttacgcgtgtccagccggagggcccagctagcaagctgctgcaacctgg
ggataaaatcattcaagctaacggttatagctttatcaacattgaacatg
gccaagctgtcagcttactgaaaacctttcagaacacagtcgaactgatt
atcgttcgcgaggtgggtaatggtgccaagcaggaaatccgcgttcgcgt
ggagaaggatggcggcagtggtgggggtgggtctgggggttctgtatctt
ctgtgccgactaacctggaagttgtcgcggccactcctacaagtctgctg
attagctgggatgcctatcgtgaactgccggtttcttattaccgcatcac
gtacggtgagacaggcggtaatagtcctgttcaagagtttactgtacctg
gtagcaaaagcaccgcgactattagtgggctgaagccgggagtggattac
accatcaccgtatatgctcattataattatcactactatagctcaccgat -continued
cagcattaactatcgtggtcctggtcgcgaatatgtgcgctttgcccgg gaagcacccaccaccatcatcatcac

TVMV-AC-AI-8-1:

(SEQ ID NO: 25)
ssgsk*allkqvrdfnpisacvcllenssdqhserlfqiqfqpyiianqhl*

*frrnnqeltiktmhqefkvknstqlqmkpveqrdiivikmakdfppfpqk*

*lkfrqptikdrvcmvstnfqqksvsslvsesshivhkedtsfwqhwittk*

*dgqcgsplvsiidgnilgihslthttngsnyfvefpekfvatyldaadqw*

*cknwkfnadkiswgsfilweggsg*spelgfsisggvggrgnpfrpdddgi fvtrvqpegpaskllqpgdkiiqangysfiniehgqavsllktfqntvel iivrevgngakqeirvrvekdggsggggsggsvssvptnlevvaatptsl liswdayrelpvsyyritygetggnspvqeftvpgskstatisglkpgvd ytitvyahynyhyysspisinyrgpg*reyvrfap*gsthhhhhh

The encoding nucleotide sequence is:

(SEQ ID NO: 53)
tctagtggttctaaagctttgctgaagggcgtgcgcgattttaatccgat ctctgcttgcgtatgcctgctggaaaactcctcggatggtcatagtgaac gtctgtttggcattggttttggcccgtatatcattgccaaccagcatctg tttcgtcgtaacaatggcgaactgaccatcaaaaccatgcatatgaattc aaagtcaaaaactctacccagctgcagatgaaaccggttgaaggccgtga cattatcgttatcaaaatggctaaagactttcccgccgttcccgcagaaac tgaaattccgtcagccgaccatcaaagatcgtgtgtgcatggtgtccacc aactttcagcagaaaagcgtctcgagcctggtgtctgaatcctctcacat tgtgcataaagaagacacttctttctggcagcactggatcaccactaaag atggccagtgtggcagcccactagtttccatcattgatggcaacattctg ggcatccacagcctgactcataccaccaacggtagcaactacttcgtgga atttccggaaaaattcgtggcgacttatctagatgccgcggatggttggt gcaaaaactggaaattcaacgcggataaaatcagctggggttcctttatc ctgtgggaaggtggtagtggtagtccggagttaggttttagtatttcagg tggtgtcggtggtcgtgggaatccttttcgtccagatgatgatggaattt tcgttacgcgtgtccagccggagggcccagctagcaagctgctgcaacct ggggataaaatcattcaagctaacggttatagctttatcaacattgaaca tggccaagctgtcagcttactgaaaacctttcagaacacagtcgaactga ttatcgttcgcgaggtgggtaatggtgccaagcaggaaatccgcgttcgc gtggagaaggatggcggcagtggtgggggtgggtctggggggttctgtatc ttctgtgccgactaacctggaagttgtcgcggccactcctacaagtctgc tgattagctgggatgcctatcgtgaactgccggtttcttattaccgcatc acgtacggtgagacaggcggtaatagtcctgttcaagagtttactgtacc tggtagcaaaagcaccgcgactattagtgggctgaagccgggagtggatt acaccatcaccgtatatgctcattataattatcactactatagctcaccg atcagcattaactatcgtggtcctggtcgcgaatatgtgcgctttgcccc gggaagcacccaccaccatcatcatcac

TVMV-AC-AI-9-3:

(SEQ ID NO: 26)
ssgsk*allkqvrdfnpisacvcllenssdqhserlfqiqfqpyiianqhl*

*frrnnqeltiktmhqefkvknstqlqmkpveqrdiivikmakdfppfpqk*

*lkfrqptikdrvcmvstnfqqksvsslvsesshivhkedtsfwqhwittk*

*dgqcgsplvsiidgnilgihslthttngsnyfvefpekfvatyldaadqw*

*cknwkfnadkiswgsfilweggg*sgspelgfsisggvggrgnpfrpdddg** ifvtrvqpegpaskllqpgdkiiqangysfiniehgqavsllktfqntve liivrevgngakqeirvrvekdggsggggsggsvssvptnlevvaatpts lliswdayrelpvsyyritygetggnspvqeftvpgskstatisglkpgv dytitvyahynyhyysspisinyrgpg*reyvrfap*gsthhhhhh

The encoding nucleotide sequence is:

(SEQ ID NO: 54)
tctagtggttctaaagctttgctgaagggcgtgcgcgattttaatccgat ctctgcttgcgtatgcctgctggaaaactcctcggatggtcatagtgaac gtctgtttggcattggttttggcccgtatatcattgccaaccagcatctg tttcgtcgtaacaatggcgaactgaccatcaaaaccatgcatggtgaatt caaagtcaaaaactctacccagctgcagatgaaaccggttgaaggccgtg acattatcgttatcaaaatggctaaagacttcccgccgttcccgcagaaa ctgaaattccgtcagccgaccatcaaagatcgtgtgtgcatggtgtccac caactttcagcagaaaagcgtctcgagcctggtgtctgaatcctctcaca ttgtgcataaagaagacacttctttctggcagcactggatcaccactaaa gatggccagtgtggcagcccactagtttccatcattgatggcaacattct gggcatccacagcctgactcataccaccaacggtagcaactacttcgtgg aatttccggaaaaattcgtggcgacttatctagatgccgcggatggttgg tgcaaaaactggaaattcaacgcggataaaatcagctggggttcctttat cctgtgggaaggtggtggtagtggtagtccggagttaggttttagtatttc aggtggtgtcggtggtcgtgggaatccttttcgtccagatgatgatgga attttcgttacgcgtgtccagccggagggcccagctagcaagctgctgca acctggggataaaatcattcaagctaacggttatagctttatcaacattg aacatggccaagctgtcagcttactgaaaacctttcagaacacagtcgaa ctgattatcgttcgcgaggtgggtaatggtgccaagcaggaaatccgcgt tcgcgtggagaaggatggcggcagtggtgggggtgggtctggggggttctg tatcttctgtgccgactaacctggaagttgtcgcggccactcctacaagt ctgctgattagctgggatgcctatcgtgaactgccggtttcttattaccg catcacgtacggtgagacaggcggtaatagtcctgttcaagagtttactg tacctggtagcaaaagcaccgcgactattagtgggctgaagccgggagtg gattacaccatcaccgtatatgctcattataattatcactactatagctc accgatcagcattaactatcgtggtcctggtcgcgaatatgtgcgctttg ccccgggaagcacccaccaccatcatcatcac

TVMV-AC-AI-10-2:

(SEQ ID NO: 27)
ssgskallkgvrdfnpisacvcllenssdghserlfgigfgpyiianghl frrnngeltiktmhgefkvknstqlqmkpvegrdiivikmakdfppfpqk lkfrqptikdrvcmvstnfqqksvsslvsesshivhkedtsfwqhwittk dgqcqsplvsiidgnilqihslthttngsnyfvefpekfvatyldaadqw cknwkfnadkiswqsfilweggsgsgspelgfsisggvggrgnpfrpddd gifvtrvqpegpaskllqpgdkiiqangysfiniehgqavsllktfqntv eliivrevgngakqeirvrvekdggsgggsggsvssvptnlevvaatpt slliswdayrelpvsyyritygetggnspvqeftvpgskstatisglkpg vdytitvyahynyhyysspisinyrgpgreyvrfapgsthhhhhh

Figure 12:
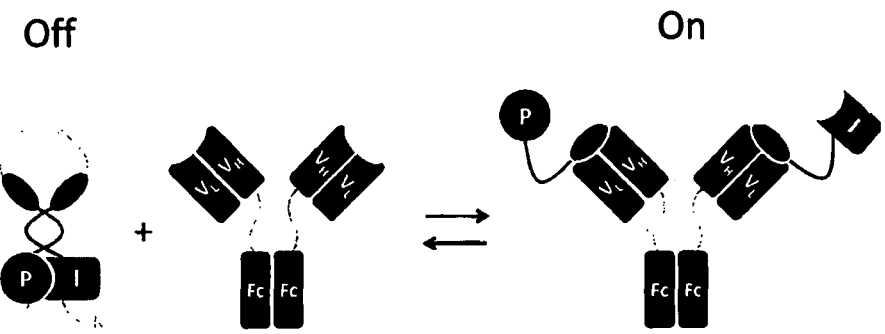
FIG. 12: An allosteric antibody detector switch. In the presence of the antibody, two epitopes that form part of the linker which connects the AI-domain to the protease biosensor bind to the antibody stabilizing the protease biosensor in an uninhibited, open conformation resulting in the generation of a proteolytic signal.
Figure 12:
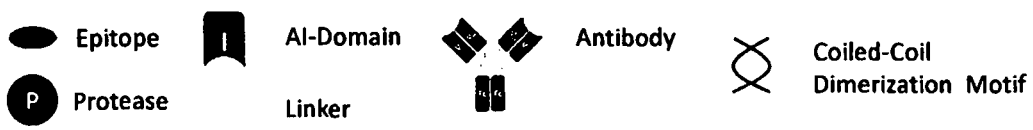

The encoding nucleotide sequence is:

(SEQ ID NO: 55)
tctagtggttctaaagctttgctgaagggcgtgcgcgatttttaatccgat ctctgcttgcgtatgcctgctggaaaactcctcggatggtcatagtgaac gtctgtttggcattggttttggcccgtatatcattgccaaccagcatctg tttcgtcgtaacaatggcgaactgaccatcaaaaccatgcatggtgaatt caaagtcaaaaactctacccagctgcagatgaaaccggttgaaggccgtg acattatcgttatcaaaatggctaaagacttcccgccgttcccgcagaaa ctgaaattccgtcagccgaccatcaaagatcgtgtgtgcatggtgtccac caactttcagcagaaaagcgtctcgagcctggtgtctgaatcctctcaca ttgtgcataaagaagacacttctttctggcagcactggatcaccactaaa gatggccagtgtggcagccactagtttccatcattgatggcaacattct gggcatccacagcctgactcataccaccaacggtagcaactacttcgtgg aatttccggaaaaattcgtggcgacttatctagatgccgcggatggttgg tgcaaaaactggaaattcaacgcggataaaatcagctggggttcctttat cctgtgggaaggtggtagtggtagtggtagtccggagttaggtatagtat ttcaggtggtgtcggtggtcgtgggaatcctttttcgtccagatgatgatg gaattttcgttacgcgtgtccagccggagggcccagctagcaagctgctg caacctggggataaaatcattcaagctaacggttatagattatcaacatt gaacatggccaagctgtcagcttactgaaaacctttcagaacacagtcga actgattatcgttcgcgaggtgggtaatggtgccaagcaggaaatccgcg ttcgcgtggagaaggatggcggcagtggtgggggtgggtctgggggttct gtatcttctgtgccgactaacctggaagttgtcgcggccactcctacaag tctgctgattagctgggatgcctatcgtgaactgccggtttcttattacc gcatcacgtacggtgagacaggcggtaatagtcctgttcaagagtttact gtacctggtagcaaaagcaccgcgactattagtgggctgaagccgggagt ggattacaccatcaccgtatatgctcattataattatcactactatagct caccgatcagcattaactatcgtggtcctggtcgcgaatatgtgcgcttt gccccgggaagcacccaccaccatcatcatcac Summary of Antibody-Specific Allosteric Receptors Allosteric receptors can be generated that are activated upon binding to a bivalent ligand such as an antibody. In the presence of the antibody, two epitopes that form part of the linker which connects the AI-domain to the protease biosensor bind to the antibody stabilizing the receptor in an uninhibited, open conformation resulting in the generation of a proteolytic signal (FIG. 12). A switch that generates a proteolytic signal can be readily engineered by recombining a suitable linker that incorporates two epitopes and a sufficiently long and rigid linker to bridge the epitope binding sites of a bi-valent antibody with a protease and an equivalent AI-domain. The induction of the proteolytic activity can subsequently be fine-tuned by modulating the length and the structure of the linker connecting AI-domain to the protease biosensor, affinity of the AI-domain for the biosensor protease, or if proving insufficient, by introducing an artificial dimerization motif that enhances the affinity of the AI-domain for the biosensor protease leading to tighter inhibition in the unbound state.

Development of Integrated Signal Sensing and Amplification Circuits Based on Autoinhibited Proteases To illustrate the ability of protease-based signal sensors and transducers to form a functional signal sensing and amplification circuit, we sought to connect the TVMV-based allosteric receptor with the HCV-based signal amplifier (FIG. 13A). This also enabled us to obtain a quantitative measure for the $K_D$ of the TVMV-based allosteric receptors for its peptide ligand. This was previously not possible considering the original ePDZ-b1 mutant binds its peptide ligand with sub-nanomolar affinity while the detection limit of TVMV-based protease activities in our assay is approximately 100 nM. To this end, the SH3-domain was inserted at the N-terminus of TVMV-AC-AI allowing the allosteric receptor to be coupled to the previously developed HCV-based signal amplifier. This improved the sensitivity of the assay 20-fold as 5 nM of the TVMV-based ligand receptor could be faithfully detected (FIG. 13B). To test the linearity of the response in the integrated signal sensing and amplification circuit, we titrated the protease receptor with increasing concentrations of the ligand peptide. Plot of the observed HCV activity against the concentration of the ligand peptide demonstrated that activity increased dose dependently and could be fitted to the value of 9.3±1.0 nM demonstrating that the circuit could faithfully detect and selectively amplify low abundant signals over a range of concentrations.

SH3-TVMV-AC-AI-37-2:

(SEQ ID NO: 28)
Sggsgaeyvralfdfngndeedlpfkkgdilrirdkpeeqwwnaedseqk rgmipypyvekyrpassasvsaliggrggsggsggsggsggsggsskall kgvrdfnpisacvcllenssdghserlfgigfgpyiianghlfrnngelt iktmhgefkvknstqlqmkpvegrdiivikmakdfppfpqklkfrqptik drvcmvstnfqqksvsslvsesshivhkedtsfwqhwittkdgqcqsplv siidgnilqihslthttngsnyfvefpekfvatyldaadqwcknwkfnad kiswqsfilwesgspelgfsisggvggrgnpfrpdddgifvtrvqpegpa

-continued skllqpgdkiiqangysfiniehgqavsllktfqntveliivrevgngak qeirvrvekdggsggggvssvptnlevvaatptsllliswdayrelpvsyy ritygetggnspvqeftvpgskstatisglkpgvdytitvyahynyhyys spisinyrgpgreyyrfapgsthhhhhh The encoding nucleotide sequence is:

(SEQ ID NO: 56)
tctggtggttctggggcagagtatgtgcgggccctctttgactttaatgg gaatgatgaagaagatcttccatttaagaaaggagacatcctgcgtatcc gggataagcctgaagagcagtggtggaatgcagaggacagcgaaggaaag cgtgggatgattcctgtcccttacgtggagaagtatcgcctgcctccgc ctcagtatcggctctgattggaggtcgggcggtagcggtggtagcggcg gtagcggcggtagcggtggctcgggcggttcgtctaaagctttgctgaag ggcgtgcgcgattttaatccgatctctgcttgcgtatgcctgctggaaaa ctcctcggatggtcatagtgaacgtctgtttggcattggttttggcccgt atatcattgccaaccagcatctgtttcgtcgtaacaatggcgaactgacc atcaaaaccatgcatggtgaattcaaagtcaaaaactctacccagctgca gatgaaaccggttgaaggccgtgacattatcgttatcaaaatggctaaag acttcccgccgttcccgcagaaactgaaattccgtcagccgaccatcaaa gatcgtgtgtgcatggtgtccaccaactttcagcagaaaagcgtctcgag cctggtgtctgaatcctctcacattgtgcataaagaagacacttattctg gcagcactggatcaccactaaagatggccagtgtggcagcccactagtac catcattgatggcaacattctgggcatccacagcctgactcataccacca acggtagcaactacttcgtggaatttccggaaaaattcgtggcgacttat ctagatgccgcggatggttggtgcaaaaactggaaattcaacgcggataa aatcagctggggttcctttatcctgtgggaaagtggtagtccggagttag gttttagtatttcaggtggtgtcggtggtcgtgggaatcatttcgtccag atgatgatggaatttttcgttacgcgtgtccagccggagggcccagctagc aagctgctgcaacctggggataaaatcattcaagctaacggttatagctt tatcaacattgaacatggccaagctgtcagcttactgaaaacctttcaga acacagtcgaactgattatcgttcgcgaggtgggtaatggtgccaagcag gaaatccgcgttcgcgtggagaaggatggcggcagtggtggggtgggt atcttctgtgccgactaacctggaagttgtcgcggccactcctacaagtc tgctgattagctgggatgcctatcgtgaactgccggtttcttattaccgc atcacgtacggtgagacaggcggtaatagtcctgttcaagagtttactgt acctggtagcaaaagcaccgcgactattagtgggctgaagccgggagtgg attacaccatcaccgtatatgctcattataattatcactactatagctca ccgatcagcattaactatcgtggtcctggtcgcgaatatgtgcgctttgc cccgggaagcacccaccaccatcatcatcac Throughout the specification, the aim has been to describe the preferred embodiments of the invention without limiting the invention to any one embodiment or specific collection of features. Various changes and modifications may be made to the embodiments, described and illustrated without departing from the present invention.

The disclosure of each patent and scientific document, computer program and algorithm referred to in this specification is incorporated by reference in its entirety.

The invention claimed is:

1. A biosensor molecule comprising a protease amino acid sequence; at least one sensor comprising at least one sensor amino acid sequence which is responsive to at least one target molecule; and an inhibitor of the protease activity of said protease; wherein the biosensor is switchable from a protease active to a protease inactive state, or from a protease inactive to a protease active state when said sensor responds to said target molecule.

2. The biosensor of claim 1, comprising (i) a single sensor comprising a single amino acid sequence responsive to a single target molecule; (ii) two sensors comprising respective amino acid sequences responsive to the same or different target molecule; (iii) a single protease amino acid sequence and a single inhibitor; and/or (iv) two different protease amino acid sequences and respective inhibitors.

3. The biosensor of claim 1, wherein the or each sensor allosterically activates or inhibits the protease activity of the biosensor upon responding to the target molecule.

4. The biosensor of claim 3, wherein the or each sensor allosterically releases inhibition of the or each protease by the inhibitor of the protease activity of said protease.

5. The biosensor of claim 1, wherein the or each sensor comprises an affinity clamp; wherein the affinity clamp comprises a recognition domain; wherein the recognition domain is capable of binding one or more target molecules.

6. The biosensor of claim 5, wherein the affinity clamp further comprises an enhancer domain.

7. The biosensor of claim 6, wherein the recognition domain is a PDZ domain.

8. The biosensor of claim 6, wherein the enhancer domain is a type III domain of fibronectin.

9. The biosensor of claim 1, wherein the or each sensor comprises one or a plurality of epitopes that can be bound by an antibody target molecule, so that said sensor responds to said antibody target molecule.

10. The biosensor of claim 1, wherein the or each sensor comprises an antibody which binds the target molecule.

11. The biosensor of claim 10, which further comprises a molecule which binds the antibody.

12. The biosensor of claim 11 the molecule is a ZZ domain of Protein A which binds the antibody.

13. The biosensor of claim 1, wherein the or each sensor amino acid sequence comprises a protease cleavage site cleavable by a protease target molecule to thereby at least partly release inhibition of the protease by the inhibitor and switch the biosensor from a protease active to a protease inactive state.

14. The biosensor of claim 1, wherein the biosensor protease is a cysteine protease, a serine protease, an aspartate protease, a metalloprotease, a threonine protease, or a glutamic acid protease.

15. The biosensor of claim 14, wherein the biosensor protease is derived or obtainable from a virus.

16. The biosensor of claim 15, wherein the virus is a Potyvirus or a Flavivirus.

17. The biosensor of claim 16, wherein the protease is an NIa protease.

18. The biosensor of claim 1, wherein the inhibitor is a peptide.

19. The biosensor of claim 1, which comprises first and second sensors responsive to the same or different target molecules.

20. The biosensor of claim 19, which is a circularly permutated biosensor.

21. The biosensor of claim 1 further comprising an amplifier interacting domain for linking or coupling the biosensor to an amplifier molecule.

22. The biosensor of claim 1 comprising an amino acid sequence set forth in any one of SEQ ID NOS: 1-10.

23. An amplifier molecule operable with the biosensor molecule of claim 1 that comprises: (i) an amino acid sequence of a protease that is different to the protease(s) of the biosensor; (ii) an inhibitor of the protease of (i); and (iii) a linker amino acid sequence which comprises a cleavage site for the protease(s) of the biosensor.

24. The amplifier molecule of claim 23 which comprises a biosensor interacting domain for linking or coupling the amplifier molecule to the biosensor.

25. A composition or kit comprising the biosensor of claim 1 and a substrate.

26. The composition or kit of claim 25, wherein the substrate comprises an amino acid sequence cleavable by the protease of the biosensor.

27. The composition or kit of claim 25, further comprising an amplifier molecule.

28. The composition or kit of claim 25, further comprising a deactivating molecule.

29. The composition or kit of claim 28, further comprising an amplifier molecule operable with the biosensor, wherein the amplifier molecule comprises: (i) an amino acid sequence of a protease that is different to the protease(s) of the biosensor, (ii) an inhibitor of the protease of (i), and (iii) a linker amino acid sequence which comprises a cleavage site for the protease(s) of the biosensor; wherein the deactivating molecule comprises: (i) an amino acid sequence of a protease that is different to the protease(s) of the biosensor and that is different to the protease of the amplifier molecule; (ii) an inhibitor of the protease of (i) and (iii) a linker amino acid sequence which comprises a cleavage site for the protease of the amplifier molecule.

30. The composition or kit of claim 25, further comprising an amplifier molecule operable with the biosensor, wherein the amplifier molecule comprises: (i) an amino acid sequence of a protease that is different to the protease(s) of the biosensor, (ii) an inhibitor of the protease of (i), and (iii) a linker amino acid sequence which comprises a cleavage site for the protease(s) of the biosensor; wherein the substrate comprises an amino acid sequence cleavable by the protease of the amplifier molecule.

31. The composition or kit of claim 25, wherein the substrate comprises a label.

32. A method of detecting a target molecule, said method including the step of contacting the composition of claim 25 with a sample to thereby determine the presence or absence of a target molecule in the sample.

* * * * *